US012178902B1

(12) United States Patent
Hong et al.

(10) Patent No.: US 12,178,902 B1
(45) Date of Patent: Dec. 31, 2024

(54) METHODS AND COMPOSITIONS FOR FLUID DRAINAGE BY PIEZO ION CHANNEL ACTIVATION

(71) Applicant: UNIVERSITY OF SOUTHERN CALIFORNIA, Los Angeles, CA (US)

(72) Inventors: Young-Kwon Hong, Los Angeles, CA (US); Dong-Won Choi, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 84 days.

(21) Appl. No.: 17/146,935

(22) Filed: Jan. 12, 2021

Related U.S. Application Data

(60) Provisional application No. 62/960,038, filed on Jan. 12, 2020.

(51) Int. Cl.
*A61K 9/00* (2006.01)
*A61K 31/497* (2006.01)
*A61K 41/00* (2020.01)
*A61P 7/00* (2006.01)

(52) U.S. Cl.
CPC .......... *A61K 9/0009* (2013.01); *A61K 9/0048* (2013.01); *A61K 31/497* (2013.01); *A61K 41/0047* (2013.01); *A61P 7/00* (2018.01)

(58) Field of Classification Search
CPC .. A61K 9/0009; A61K 9/0048; A61K 31/497; A61K 41/0047; A61P 7/00
See application file for complete search history.

(56) References Cited

U.S. PATENT DOCUMENTS

| | | | |
|---|---|---|---|
| 6,894,054 B2 * | 5/2005 | Laborde | A61P 25/00 514/342 |
| 7,514,566 B2 | 4/2009 | Zeng et al. | |
| 7,951,821 B2 | 5/2011 | Dargazanli et al. | |
| 8,084,479 B2 | 12/2011 | Zeng et al. | |
| 2003/0073726 A1 | 4/2003 | Baker et al. | |
| 2008/0305520 A9 | 12/2008 | Hamill et al. | |
| 2013/0156762 A1 | 6/2013 | Coste et al. | |

FOREIGN PATENT DOCUMENTS

| | | | | |
|---|---|---|---|---|
| WO | 99/32619 A1 | 7/1999 | | |
| WO | 00/44895 A1 | 8/2000 | | |
| WO | 01/29058 A1 | 4/2001 | | |
| WO | 01/36646 A1 | 5/2001 | | |
| WO | 2002/064135 A1 | 8/2002 | | |
| WO | WO-02064135 A1 * | 8/2002 | ............. | A61K 31/41 |
| WO | 2005/070122 A2 | 8/2005 | | |
| WO | 2007/098252 A2 | 8/2007 | | |
| WO | 2012/027389 A2 | 3/2012 | | |

OTHER PUBLICATIONS

Elizabeth L. Evans. Yoda1 analogue (Dooku1) which antagonizes Yoda1-evoked activation of Piezo1 and aortic relaxation British Journal of Pharmacology (2018) 175 1744-1759 (Year: 2018).*
Lukacs, V. et al. Impaired PIEZO1 function in patients with a novel autosomal recessive congenital lymphatic dysplasia. Nat. Commun. 6:8329 doi: 10.1038/ncomms9329 (2015). (Year: 2015).*
Martin Loynaz Prieto et al. Activation of Piezo1 but not NAv1.2 Channels by Ultrasound at 43 MHz, 2017, Ultrasound in Med. &Bio. vol. 44, No. 6, pp. 1217-1232 (Year: 2017).*
W. Morozumi, S. Inagaki, Y. Iwata, S. Nakamura, H. Hara, M. Shimazawa, Piezo channel plays a part in retinal ganglion cell damage. Exp. Eye Res., 191 (2020), Article 107900. doi.org/10.1016/j.exer.2019.107900 (Year: 2019).*
K. Nonomura, V. Lukacs, D.T. Sweet, L.M. Goddard, A. Kanie, T. Whitwam, S.S. Ranade, T. Fujimori, M.L. Kahn, A. Patapoutian Mechanically activated ion channel PIEZO1 is required for lymphatic valve formation Proc. Natl. Acad. Sci. U. S. A., 115 (2018), pp. 12817-12822 (Year: 2018).*
N. Mikhailov, J. Leskinen, I. Fagerlund, E. Poguzhelskaya, R. Giniatullina, O. Gafurov, T. Malm, T. Karjalainen, O. Gröhn, R. Giniatullin.Mechanosensitive meningeal nociception via Piezo channels: Implications for pulsatile pain in migraine? Neuropharmacology. (149) (May 1, 2019), pp. 113-123, (Year: 2019).*
Janardhan, H.P. et al., "Hdac3 regulates lymphovenous and lymphatic valve formation," The J. of Clinical Investigation (2017), v. 127, n. 11, pp. 4193-4206.
Kazenwadel, J. et al., "GATA2 is required for lymphatic vessel valve development and maintenance," The J. of Clinical Investigation (2015), v. 125, n. 8, pp. 2979-2994.
Kim, S.E. et al., "The role of *Drosophila* Piezo in mechanical nociception," Nature (2012), 483, pp. 209-212.
Kim, D.H. et al., "Shear stress and circumferential stretch by pulsatile flow direct vascular endothelial lineage commitment of mesenchymal stem cells in engineered blood vessels," J. Mater. Sci. Mater. Med. (2016), 27:60, pp. 1-11.
Li, J. et al., "Piezo1 integration of vascular architecture with physiological force," Nature (2014), 515, 27 pgs.
Lukacs, V. et al., "Impaired PIEZO1 function in patients with a novel autosomal recessive congenital lymphatic dysplasia," Nat. Commun. (2015), 7 pgs.
Moore, J.E. Jr. et al.,"A device for subjecting vascular endothelial cells to both fluid shear stress and circumferential cyclic stretch," Ann Biomed Eng. (1994), Annals of Biomedical Engineering (1994), v. 22, pp. 416-422.

(Continued)

*Primary Examiner* — Walter E Webb
*Assistant Examiner* — Amanda Michelle Petritsch
(74) *Attorney, Agent, or Firm* — Brooks Kushman P.C.

(57) ABSTRACT

A method of treating impaired lymphatic function in a subject is provided. The method includes a step of inducing activation of Piezo1 ion channels in lymphatic tissues of a subject having impaired lymphatic function. Similarly, a method of treating ocular hypertension or glaucoma in a subject includes a step of inducing activation of Piezo1 ion channels in an eye of a subject having an ocular pressure that is greater than 22 mm Hg. Finally, a method of treating ocular hypertension or glaucoma in a subject includes a step of inducing activation of Piezo1 ion channels in an eye of a subject having an ocular pressure that is greater than 22 mm Hg.

12 Claims, 15 Drawing Sheets

Specification includes a Sequence Listing.

(56) References Cited

OTHER PUBLICATIONS

Owatverot, T.B. et al., "Effect of Combined Cyclic Stretch and Fluid Shear Stress on Endothelial Cell Morphological Responses," J. Biomech. Eng. (2005), v. 127, pp. 374-382.
Ranade, S.S. et al., "Piezo1, a mechanically activated ion channel, is required for vascular development in mice," Proc. Natl Acad Sci U.S.A. (2014), v. 111, n. 28, pp. 10347-10352.
Sabine, A. et al., "Mechanotransduction, PROX1, and FOXC2 Cooperate to Control Connexin37 and Calcineurin during Lymphatic-Valve Formation," Dev Cell. (2012), 22, pp. 430-445.
Sabine, A. et al., "FOXC2 and fluid shear stress stabilize postnatal lymphatic vasculature," J. Clin Invest. (2015), v. 125, n. 10, pp. 3861-3877.
Sabine, A. et al., "Endothelial Cell Responses to Biomechanical Forces in Lymphatic Vessels," Antioxid Redox Signal (2016), v. 25, n. 7, pp. 451-465.
Schwartz, M.A. et al., "Lymphatics thrive on stress: mechanical force in lymphatic development," Embo J. (2012), v. 31, n. 4, pp. 781-782.
Sessa, W.C., "Molecular control of blood flow and antiogenesis: role of nitric oxide," J. Thromb Haemost. (2009), 7 (Suppl.1), pp. 35-37.
Syeda, R. et al., "Chemical activation of the mechanotransduction channel Piezo1," Elife (2015), pp. 1-11.
Udan, R.S. et al., "The Ebb and Flow of Lymphatic Valve Formation," Dev Cell 22 (2012), pp. 242-243.
Zhao, S. et al., "Synergistic Effects of Fluid Shear Stress and Cyclic Circumferential Stretch on Vascular Endothelial Cell Morphology and Cytoskeleton," Arterioscler Thomb Vasc Biol. (1995), v. 15, n. 10, pp. 1781-1786.
Baeyens, N. et al., "Endothelial fluid shear stress sensing in vascular health and disease," The J. of Clinical Investigation (2016), v. 126, n. 3, pp. 821-828.
Bazigou, E. et al., "Integrin-a9 Is Required for Fibronectin Matrix Assembly During Lymphatic Valve Morphogenesis," Developmental Cell (2009), 17, pp. 175-186.
Bazigou, E. et al., "Genes regulating lymphangiogenesis control venous valve formation and maintenance in mice," The J. of Clinical Investigation (2011), v. 121, n. 8, pp. 2984-2992.
Bazigou, E. et al., "Flow control in our vessels: vascular valves make sure there is No. way back," Cell. Mol. Life Sci. (2013), 70, pp. 1055-1066.
Bazigou, E. et al., "Primary and secondary lymphatic valve development: Molecular, functional and mechanical Insights," Microvascular Research (2014), 94, pp. 38-45.
Boldock, L. et al., "Microfluidic traction force microscopy to study mechanotransduction in angiogenesis," Microcirculation (2017), https://doi.org/10.1111/micc.12361, 7 pgs.
Breslin, J.W., "Mechanical forces and lymphatic transport," Microvascular Research (2014), 96, pp. 46-54.
Cahalan, S.M. et al., "Piezo 1 links mechanical forces to red blood cell volume," eLife (2015), DOI: 10.7554/eLife.07370, 12 pgs.
Cha, B. et al., "Mechanotransduction activates canonical Wnt/β-catenin signaling to promote lymphatic vascular patterning and the development of lymphatic and lymphovenous valves," Genes Dev (2016), V. 30, n. 12, pp. 1454-1469.
Chatterjee, S. et al., "Mechanosignaling in the vasculature: emerging concepts in sensing, transduction and physiological responses," Am J Physiol Heart Circ Physiol. (2015) ;308(12), pp. H1451-H1462.
Chiu, J.J. et al., "Effects of disturbed flow on vascular endothelium: pathophysiological basis and clinical perspectives," Physiol Rev. (2011), 91(1), pp. 327-387.
Choi, I. et al., "Visualization of lymphatic vessels by Prox1-promoter directed GFP reporter in a bacterial artificial chromosome-based transgenic mouse," Blood. (2011), 117(1), pp. 362-365.
Coste, B. et al., "Piezo1 and Piezo2 Are Essential Components of Distinct Mechanically Activated Cation Channels," Science (2010), v. 330, pp. 55-60.
Coste, B. et al., "Piezos are pore-forming subunits of mechanically activated channels, "Nature, (2012), 483, pp. 176-181.
Fotious, E. et al., "Novel mutations in PIEZO1 cause an autosomal recessive generalized lymphatic dysplasia with hon-immune hydrops fetalis," Nature Commun. (2015), 7 pgs.
Hong, M. et al., "Efficient Assessment of Developmental, Surgical and Pathological Lymphangiogenesis Using a Lymphatic Reporter Mouse and Its Embryonic Stem Cells," PLoS One (2016), pp. 1-14.
Baeyens, N. et al., "Biomechanics of Vascular Mechanosensation and Remodeling," Mol. Biol. Cell. (2016) v. 27, pp. 7-11.

\* cited by examiner

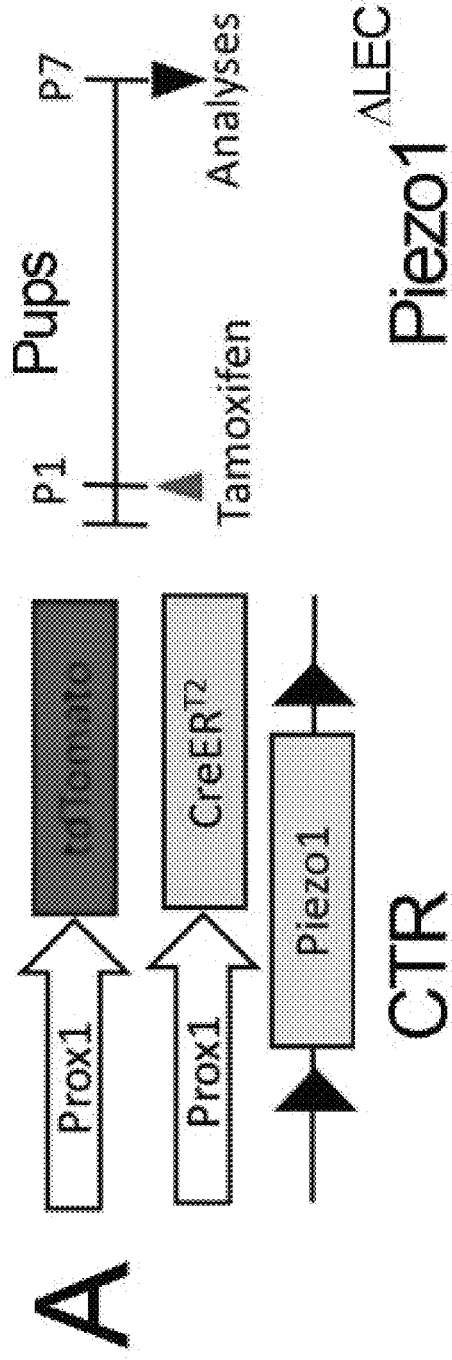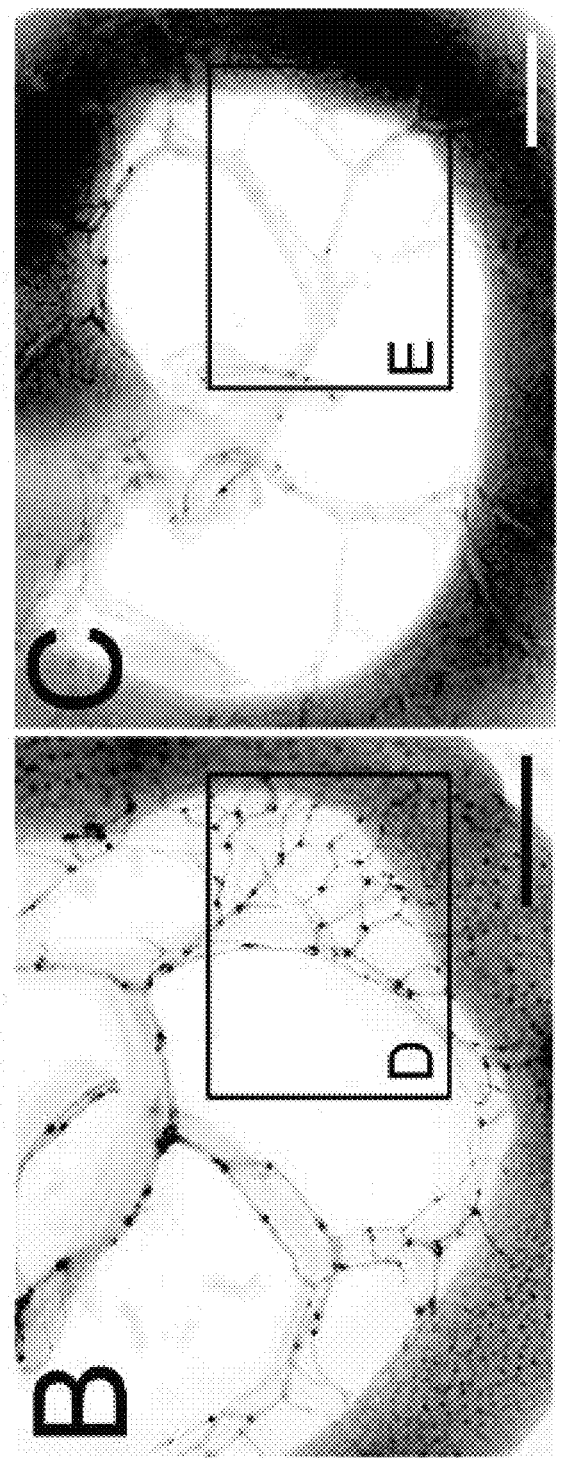
FIG. 1A
FIG. 1B
FIG. 1C

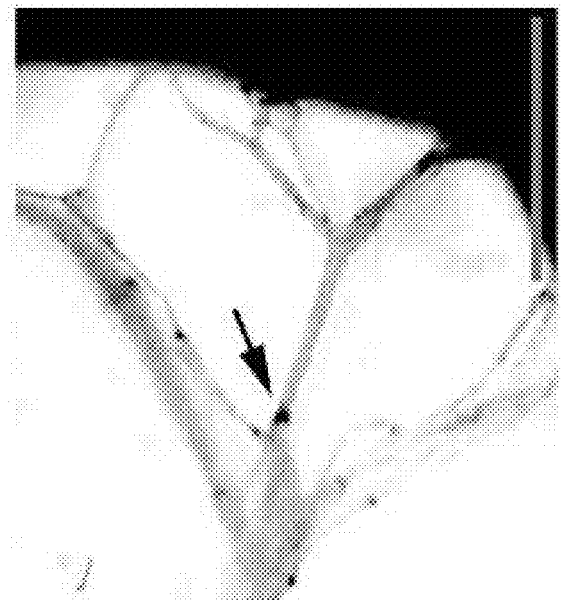
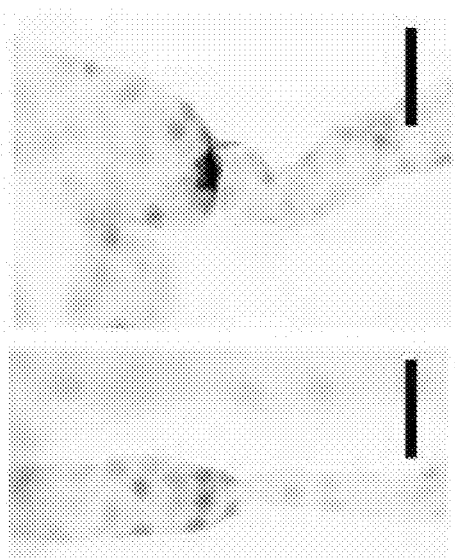
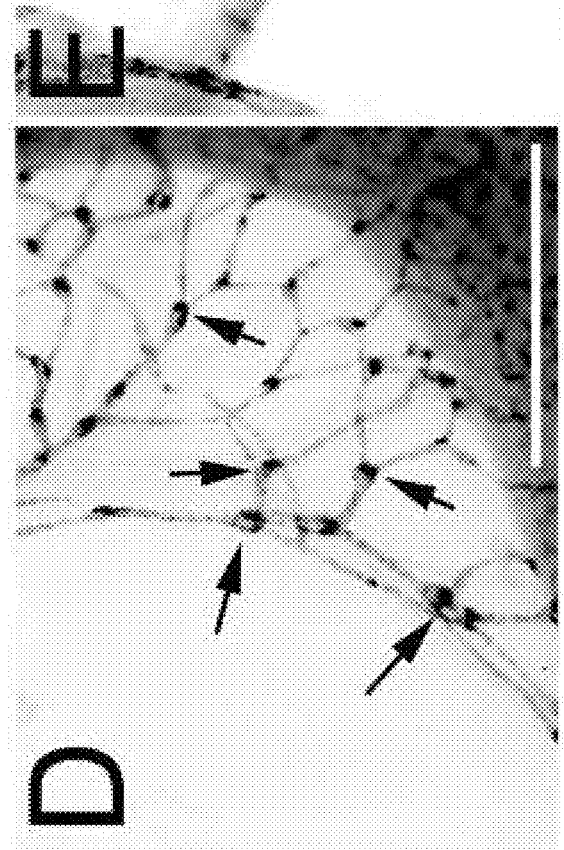
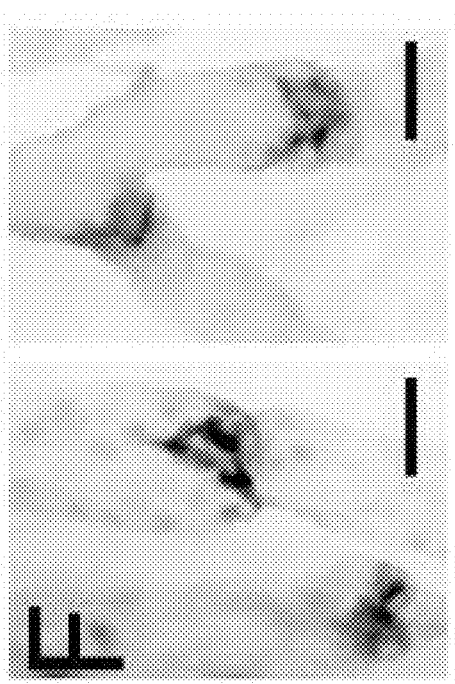

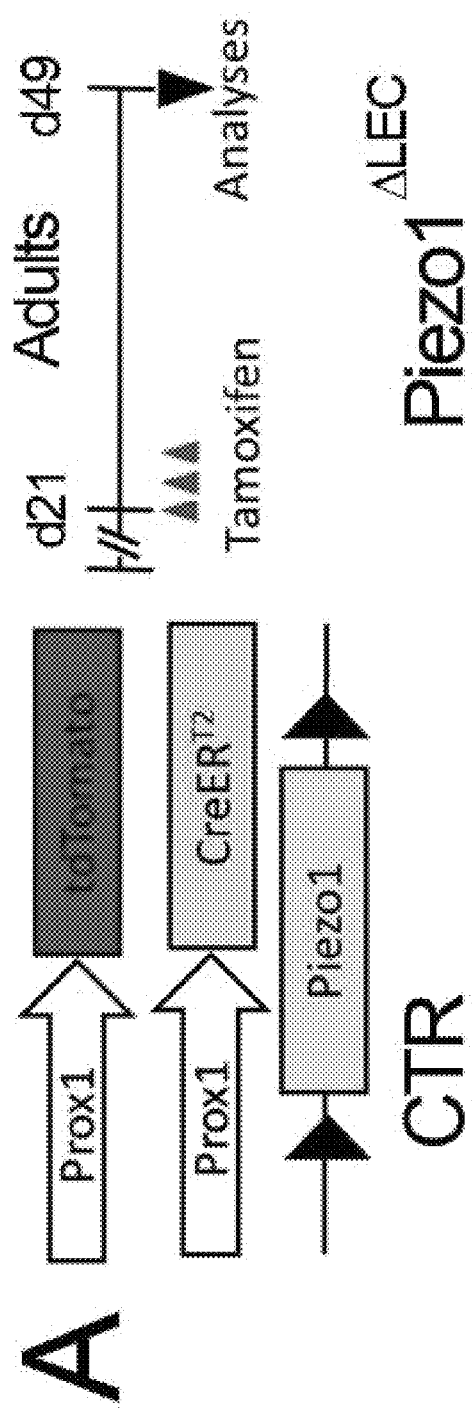
FIG. 2A
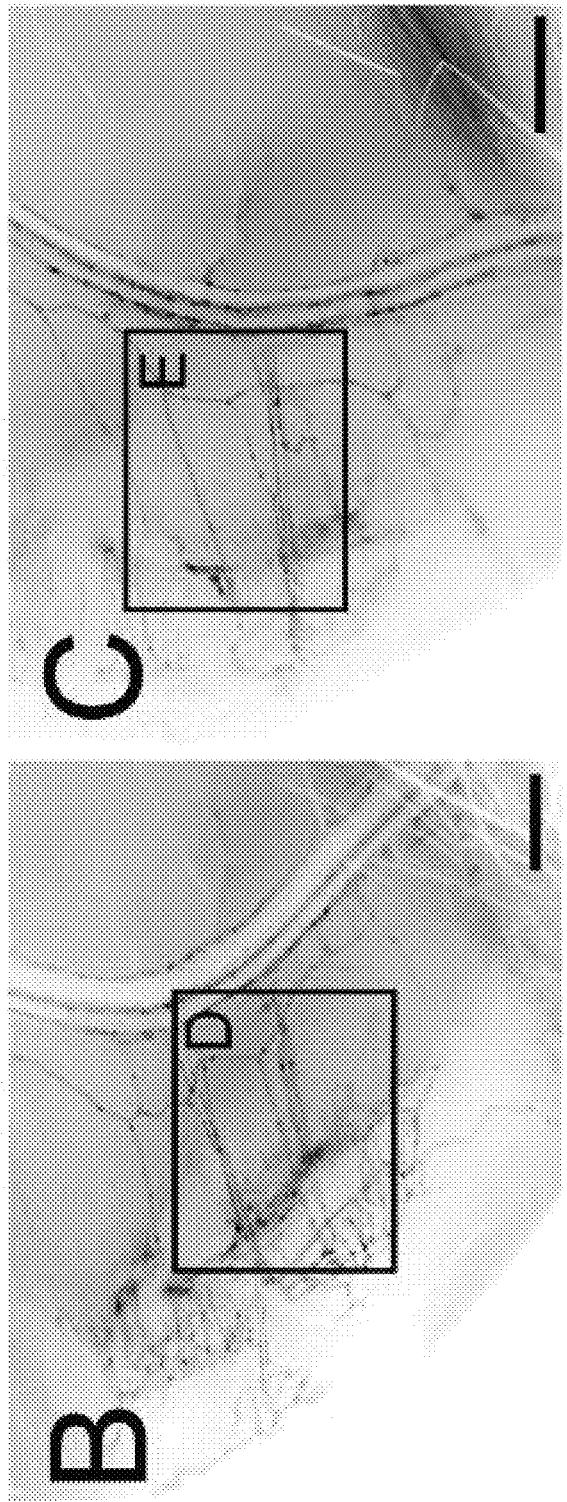
FIG. 2B
FIG. 2C

FIG. 3A
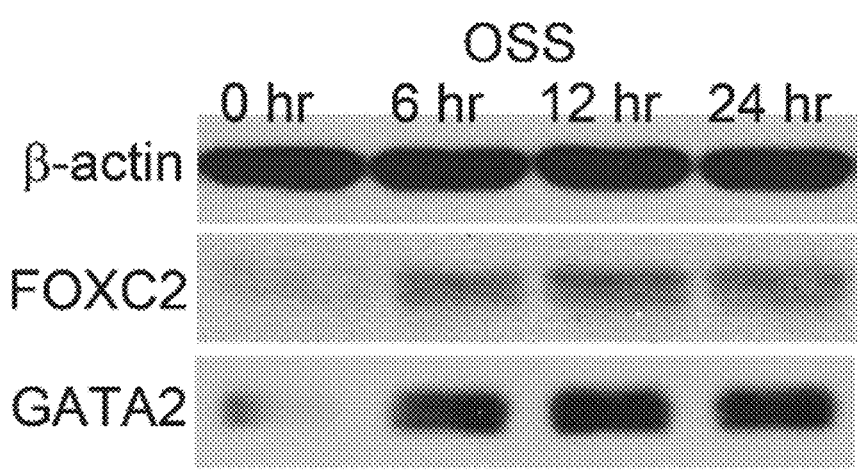
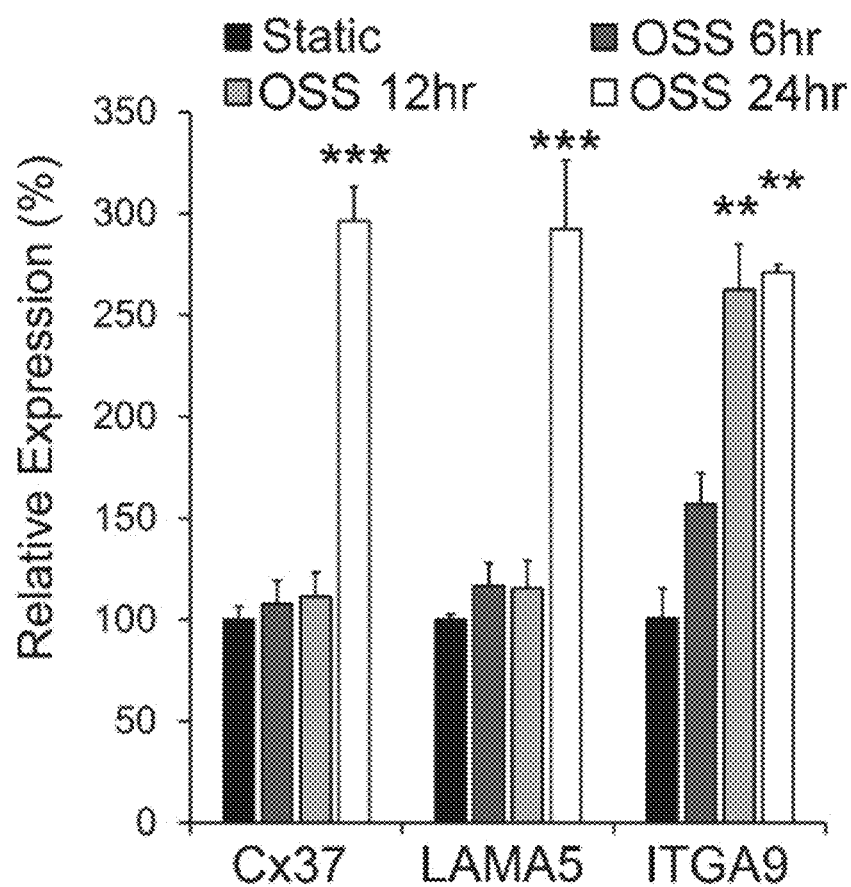
FIG. 3B

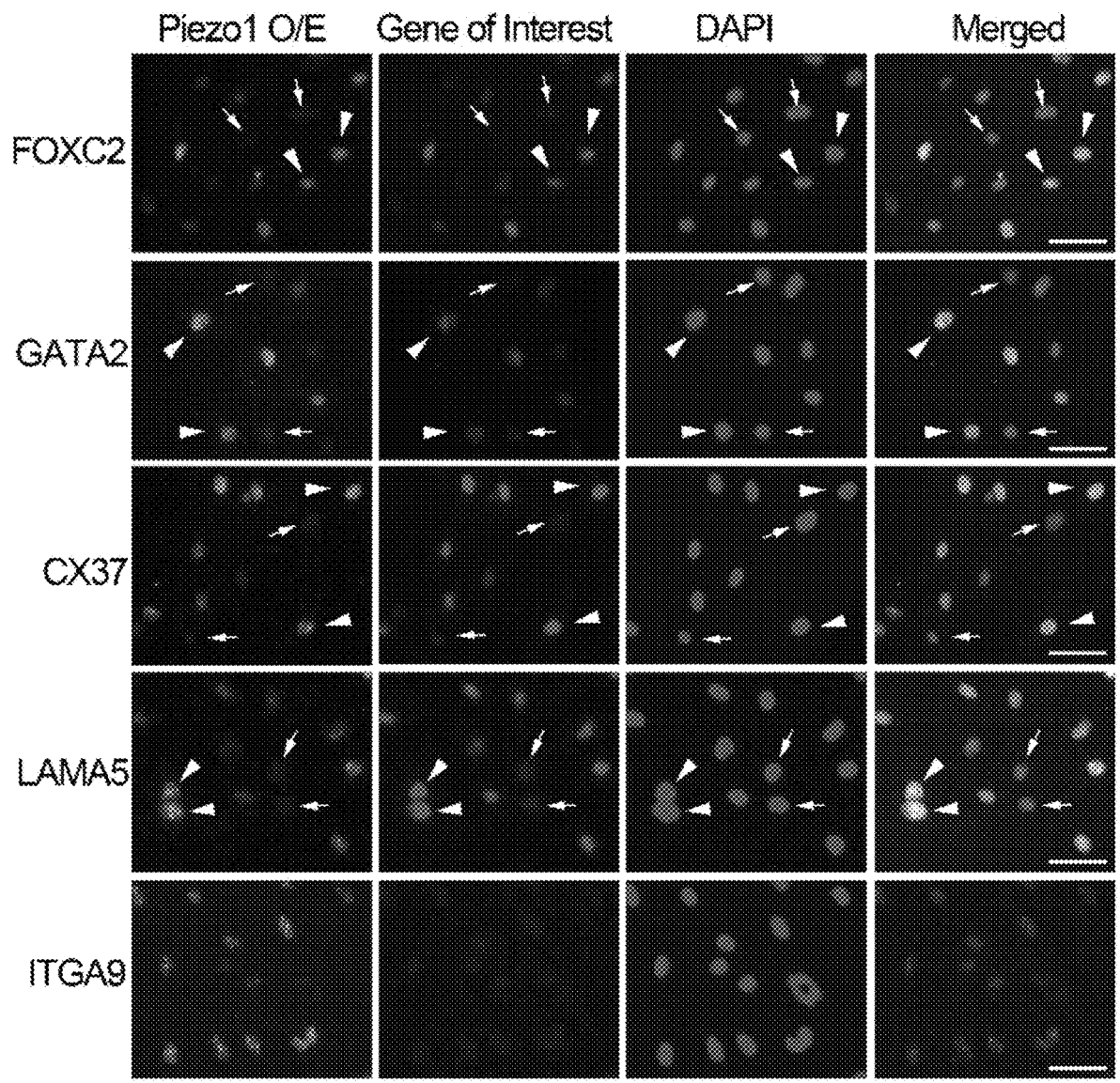

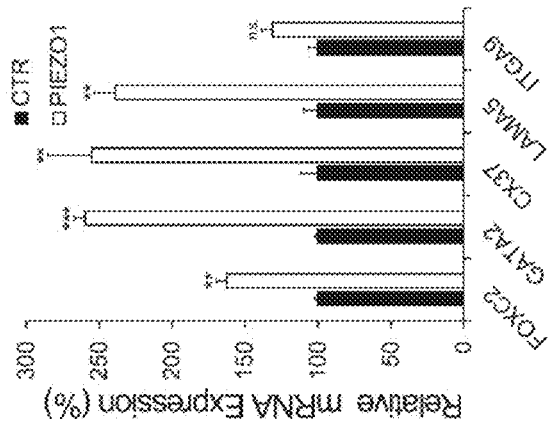
FIG. 3E
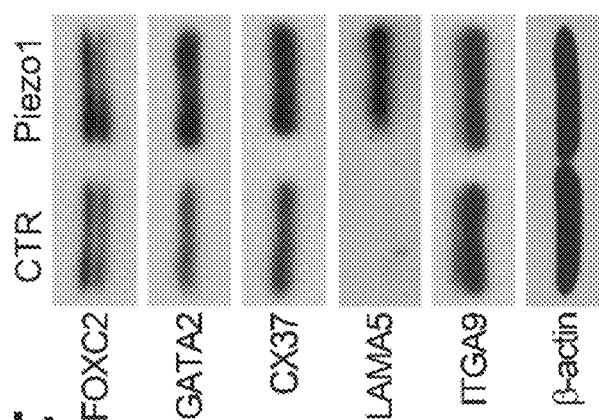
FIG. 3F
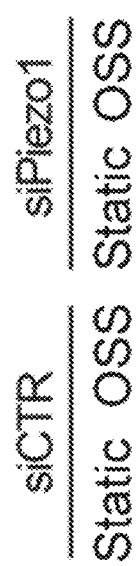
FIG. 3C
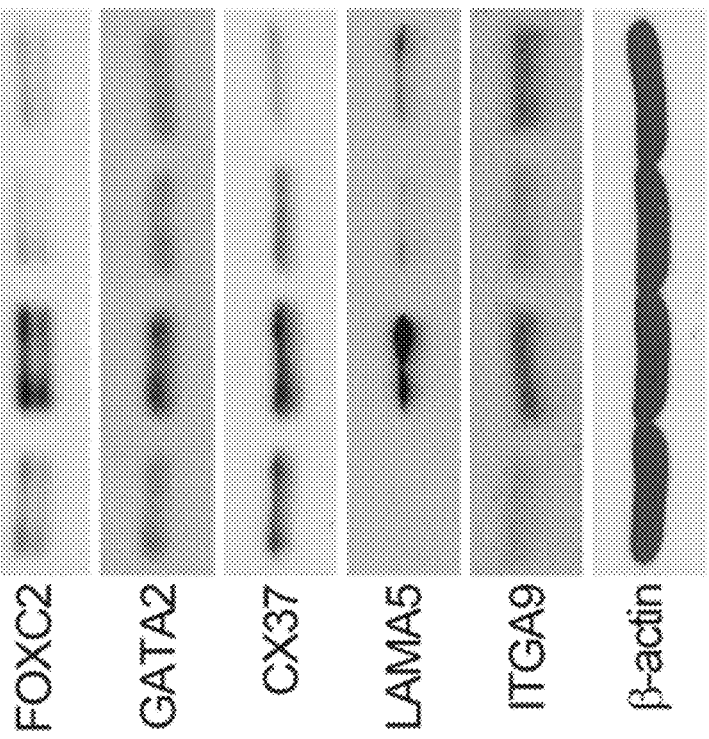

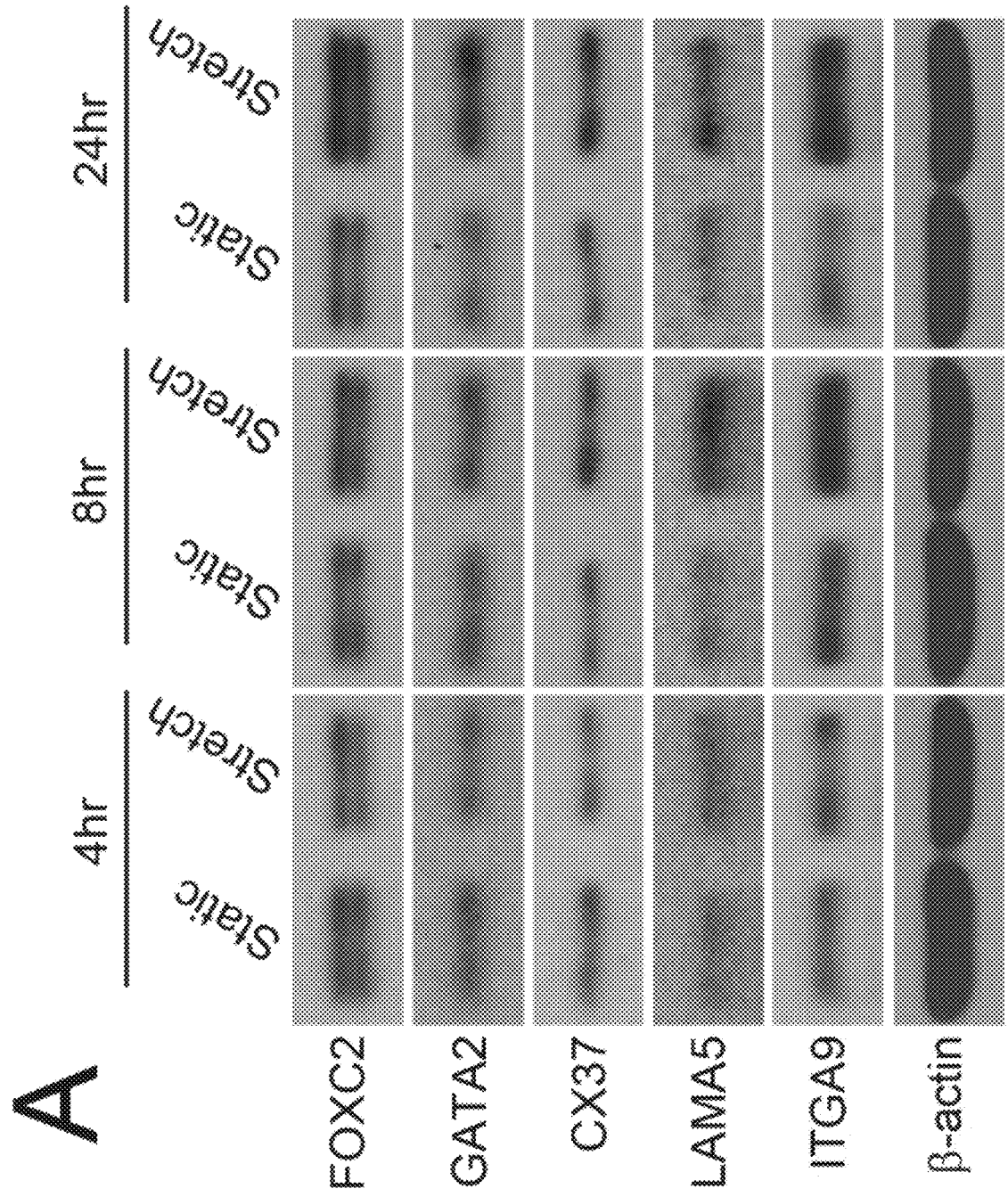

SEQUENCE LISTING

<160> NUMBER OF SEQ ID NOS: 4

<210> SEQ ID NO 1
<211> LENGTH: 7566
<212> TYPE: DNA
<213> ORGANISM: Homo sapiens

<400> SEQUENCE: 1

```
atggagccgc acgtgctcgg cgcggtcctg tactggctgc tgctgccctg cgcgctgctg      60
gctgcctgcc tgctccgctt cagcggactc tcgctggtct acctgctctt cctgctgctg     120
ctgccctggt tccccggccc cacccgatgc ggcctccaag gtcacacagg ccgcctcctg     180
cgggcattgc tgggcctcag cctgctcttc ctggtggccc atctcgccct ccagatctgc     240
ctgcatattg tgccccgcct ggaccagctc ctgggaccca gctgcagccg ctgggagacc     300
ctctcgcgac ataggggt cacaaggctg gacctgaagg acatccccaa cgccatccgg     360
ctggtggccc ctgacctggg catcttggtg gtctcctctg tctgcctcgg catctgcggg     420
cgccttgcaa ggaacacccg gcagagccca catccacggg agctggatga tgatgagagg     480
gatgtggatg ccagcccgac ggcagggctg caggaagcag caacgctggc ccctacacgg     540
aggtcacggc tggccgctcg tttccgagtc acggcccact ggctgctggt ggcggctggg     600
cgggtcctgg ccgtaacact gcttgcactg gcaggcatcg cccaccccctc ggccctctcc     660 agtgtctacc tgctgctctt cctggccctc tgcacctggt gggcctgcca cttccccatc     720
agcactcggg gcttcagcag actctgcgtc gcggtggggt gcttcggcgc cggccatctc     780
atctgcctct actgctacca gatgcccttg gcacaggctc tgctcccgcc tgccggcatc     840
tgggctaggg tgctgggtct caaggacttc gtgggtccca ccaactgctc cagcccccac     900
gcgctggtcc tcaacaccgg cctggactgg cctgtgtatg ccagcccggg cgtcctcctg     960
ctgctgtgct acgccacggc ctctctgcgc aagctccgcg cgtaccgccc ctccggccag    1020
aggaaggagg cggcaaaggg gtatgaggct cgggagctga gctagcaga gctggaccag    1080 tggccccagg aacgggagtc tgaccagcac gtggtgccca cagcacccga caccgaggct    1140
```

```
gataactgca tcgtgcacga gctgaccggc cagagctccg tcctgcggcg gcctgtgcgg    1200
cccaagcggg ctgagcccag ggaggcgtct ccgctccaca gcctgggcca cctcatcatg    1260
gaccagagct atgtgtgcgc gctcattgcc atgatggtat ggagcatcac ctaccacagc    1320
tggctgacct tcgtactgct gctctgggcc tgcctcatct ggacggtgcg cagccgccac    1380
caactggcca tgctgtgctc gccctgcatc ctgctgtatg ggatgacgct gtgctgccta    1440
cgctacgtgt gggccatgga cctgcgccct gagctgccca ccaccctggg ccccgtcagc    1500
ctgcgccagc tggggctgga gcacacccgc taccctgtc tggaccttgg tgccatgttg     1560
ctctacaccc tgaccttctg gctcctgctg cgccagtttg tgaaagagaa gctgctgaag    1620
tgggcagagt ctccagctgc gctgacggag gtcaccgtgg cagacacaga gcccacgcgg    1680
acgcagacgc tgttgcagag cctgggggag ctggtgaagg gcgtgtacgc caagtactgg    1740
atctatgtgt gtgctggcat gttcatcgtg gtcagcttcg ccggccgcct cgtggtctac    1800
aagattgtct acatgttcct cttcctgctc tgcctcaccc tcttccaggt ctactacagc    1860
ctgtggcgga agctgctcaa ggccttctgg tggctcgtgg tggcctacac catgctggtc    1920
ctcatcgccg tctacacctt ccagttccag gacttccctg cctactggcg caacctcact    1980
ggcttcaccg acgagcagct gggggacctg ggcctggagc agttcagcgt gtccgagctc    2040
ttctccagca tcctggtgcc cggcttcttc ctcctggcct gcatcctgca gctgcactac    2100
ttccacaggc ccttcatgca gctcaccgac atggagcacg tgtccctgcc tggcacgcgc    2160
ctcccgcgct gggctcacag gcaggatgca gtgagtggga ccccactgct gcgggaggag    2220
cagcaggagc atcagcagca gcagcaggag gaggaggagg aggaggagga ctccagggac    2280
gaggggctgg gcgtggccac tccccaccag gccacgcagg tgcctgaagg ggcagccaag    2340
tggggcctgg tggctgagcg gctgctggag ctggcagccg gcttctcgga cgtcctctca    2400
cgcgtgcagg tgttcctgcg gcggctgctg gagcttcacg ttttcaagct ggtggccctg    2460
tacaccgtct gggtggccct gaaggaggtg tcggtgatga acctgctgct ggtggtgctg    2520
tgggccttcg ccctgcccta cccacgcttc cggcccatgg cctcctgcct gtccaccgtg    2580
tggacctgcg tcatcatcgt gtgtaagatg ctgtaccagc tcaaggttgt caaccccccag   2640 gagtattcca gcaactgcac cgagcccttc cccaacagca ccaacttgct gcccacggag    2700
atcagccagt ccctgctgta ccgggggccc gtggaccctg ccaactggtt tggggtgcgg    2760
aaagggttcc ccaacctggg ctacatccag aaccacctgc aagtgctgct gctgctggta    2820
ttcgaggcca tcgtgtaccg gcgccaggag cactaccgcc ggcagcacca gctggcccg    2880 ctgcctgccc aggccgtgtt tgccagcggc acccgccagc agctggacca ggatctgctc    2940
ggctgcctca gtacttcat caacttcttc ttctacaaat tcgggctgga gatctgcttc    3000
ctgatggccg tgaacgtgat cgggcagcgc atgaactttc tggtgaccct gcacggttgc    3060
tggctggtgg ccatcctcac ccgcaggcac cgccaggcca ttgcccgcct ctggcccaac    3120
tactgcctct tcctggcgct gttcctgctg taccagtacc tgctgtgcct ggggatgccc    3180
ccggccctgt gcattgatta tccctggcgc tggagccggg ccgtccccat gaactccgca    3240
ctcatcaagt ggctgtacct gcctgatttc ttccggggccc ccaactccac caacctcatc    3300
agcgactttc tcctgctgct gtgcgcctcc cagcagtggc aggtgttctc agctgagcgc    3360
acagaggagt ggcagcgcat ggctggcgtc aacaccgacc gcctggagcc gctgcggggg    3420
gagcccaacc ccgtgcccaa ctttatccac tgcaggtcct accttgacat gctgaaggtg    3480
gccgtcttcc gataccttgtt ctggctggtg ctggtggtgg tgtttgtcac ggggcccacc    3540
```

```
cgcatcagca tcttcgggct gggctacctg ctggcctgct tctacctgct gctcttcggc    3600
acggccctgc tgcagaggga cacacgggcc cgcctcgtgc tgtgggactg cctcattctg    3660
tacaacgtca ccgtcatcat ctccaagaac atgctgtcgc tcctggcctg cgtcttcgtg    3720
gagcagatgc agaccggctt ctgctgggtc atccagctct tcagccttgt atgcaccgtc    3780
aagggctact atgaccccaa ggagatgatg gacagagacc aggactgcct gctgcctgtg    3840
gaggaggctg gcatcatctg ggacagcgtc tgcttcttct tcctgctgct gcagcgccgc    3900
gtcttcctta gccattacta cctgcacgtc agggccgacc tccaggccac cgccctgcta    3960
gcctccaggg gcttcgccct ctacaacgct gccaacctca gagcattga ctttcaccgc    4020 aggatagagg agaagtccct ggcccagctg aaaagacaga tggagcgtat ccgtgccaag    4080
caggagaagc acaggcaggg ccgggtggac cgcagtcgcc cccaggacac cctgggcccc    4140
aaggaccccg gcctggagcc agggcccgac agtccagggg gctcctcccc gccacggagg    4200
cagtggtggc ggccctggct ggaccacgcc acagtcatcc actccgggga ctacttcctg    4260
tttgagtccg acagtgagga agaggaggag gctgttcctg aagacccgag gccgtcggca    4320
cagagtgcct tccagctggc gtaccaggca tgggtgacca acgcccaggc ggtgctgagg    4380
cggcggcagc aggagcagga gcaggcaagg caggaacagg caggacagct acccacagga    4440
ggtggtccca gccaggaggt ggagccagca gagggcccg aggaggcagc ggcaggccgg    4500
agccatgtgg tgcagagggt gctgagcacg gcgcagttcc tgtggatgct ggggcaggcg    4560
ctagtggatg agctgacacg ctggctgcag gagttcaccc ggcaccacgg caccatgagc    4620
gacgtgctgc gggcagagcg ctacctcctc acacaggagc tcctgcaggg cggcgaagtg    4680
cacaggggcg tgctggatca gctgtacaca agccaggccg aggccacgct gccaggcccc    4740
accgaggccc ccaatgcccc aagcaccgtg tccagtgggc tgggcgcgga ggagccactc    4800
agcagcatga cagacgacat gggcagcccc ctgagcaccg gctaccacac gcgcagtggc    4860
agtgaggagg cagtcaccga ccccggggag cgtgaggctg gtgcctctct gtaccaggga    4920
ctgatgcgga cggccagcga gctgctcctg acaggcgcc tgcgcatccc agagctggag    4980
gaggcagagc tgtttgcgga ggggcagggc cgggcgctgc ggctgctgcg ggccgtgtac    5040
cagtgtgtgg ccgcccactc ggagctgctc tgctacttca tcatcatcct caaccacatg    5100
gtcacggcct ccgccggctc gctggtgctg cccgtgctcg tcttcctgtg gccatgctg    5160 tcgatcccga ggcccagcaa gcgcttctgg atgacggcca tcgtcttcac cgagatcgcg    5220
gtggtcgtca agtacctgtt ccagtttggg ttcttcccct ggaacagcca cgtggtgctg    5280
cggcgctacg agaacaagcc ctacttcccg ccccgcatcc tgggcctgga agactgac    5340 ggctacatca agtacgacct ggtgcagctc atggcccttt tcttccaccg ctcccagctg    5400
ctgtgctatg gcctctggga ccatgaggag gactcaccat ccaaggagca tgacaagagc    5460
ggcgaggagg agcagggagc cgaggagggg ccaggggtgc ctgcggccac caccgaagac    5520
cacattcagg tggaagccag ggtcggaccc acggacggga ccccagaacc ccaagtggag    5580
ctcaggcccc gtgatacgag gcgcatcagt ctacgtttta gaagaaggaa gaaggagggc    5640
ccagcacgga aaggagcggc agccatcgaa gctgaggaca gggaggaaga agaggggag    5700 gaagagaaag aggccccac ggggagagag aagaggccaa gccgctctgg aggaagagta    5760
agggcggccg gcggcggct gcagggcttc tgcctgtccc tggcccaggg cacatatcgg    5820
ccgctacggc gcttcttcca cgacatcctg cacaccaagt accgcgcagc caccgacgtc    5880
```

-continued

| | |
|---|---|
| tatgccctca tgttcctggc tgatgttgtc gacttcatca tcatcatttt tggcttctgg | 5940 |
| gcctttggga agcactcggc ggccacagac atcacgtcct ccctatcaga cgaccaggta | 6000 |
| cccgaggctt tcctggtcat gctgctgatc cagttcagta ccatggtggt tgaccgcgcc | 6060 |
| ctctacctgc gcaagaccgt gctgggcaag ctggccttcc aggtggcgct ggtgctggcc | 6120 |
| atccacctat ggatgttctt catcctgccc gccgtcactg agaggatgtt caaccagaat | 6180 |
| gtggtggccc agctctggta cttcgtgaag tgcatctact tcgccctgtc cgcctaccag | 6240 |
| atccgctgcg gctaccccac ccgcatcctc ggcaacttcc tcaccaagaa gtacaatcat | 6300 |
| ctcaacctct cctcttcca ggggttccgg ctggtgccgt tcctggtgga gctgcgggca | 6360 |
| gtgatggact gggtgtggac ggacaccacg ctgtccctgt ccagctggat gtgtgtggag | 6420 |
| gacatctatg ccaacatctt catcatcaaa tgcagccgag agacagagaa gaaatacccg | 6480 |
| cagcccaaag gcagaagaa gaagaagatc gtcaagtacg gcatgggtgg cctcatcatc | 6540 |
| ctcttcctca tcgccatcat ctggttccca ctgctcttca tgtcgctggt gcgctccgtg | 6600 |
| gttgggggttg tcaaccagcc catcgatgtc accgtcaccc tgaagctggg cggctatgag | 6660 |
| ccgctgttca ccatgagcgc ccagcagccg tccatcatcc ccttcacggc ccaggcctat | 6720 |
| gaggagctgt cccggcagtt tgaccccag ccgctggcca tgcagttcat cagccagtac | 6780 |
| agccctgagg acatcgtcac ggcgcagatt gagggcagct ccggggcgct gtggcgcatc | 6840 |
| agtcccccca gccgtgccca gatgaagcgg gagctctaca cggcacggc cgacatcacc | 6900 |
| ctgcgcttca cctggaactt ccagagggac ctggcgaagg gaggcactgt ggagtatgcc | 6960 |
| aacgagaagc acatgctggc cctggcccc aacagcactg cacggcggca gctggccagc | 7020 |
| ctgctcgagg gcacctcgga ccagtctgtg gtcatcccta atctcttccc caagtacatc | 7080 |
| cgtgccccca acgggcccga agccaaccct gtgaagcagc tgcagcccaa tgaggaggcc | 7140 |
| gactacctcg gcgtgcgtat ccagctgcgg agggagcagg gtgcggggc caccggcttc | 7200 |
| ctcgaatggt gggtcatcga gctgcaggag tgccggaccg actgcaacct gctgcccatg | 7260 |
| gtcattttca gtgacaaggt cagcccaccg agcctcggct tcctggctgg ctacggcatc | 7320 |
| atggggctgt acgtgtccat cgtgctggtc atcggcaagt tcgtgcgcgg attcttcagc | 7380 |
| gagatctcgc actccattat gttcgaggag ctgccgtgcg tggaccgcat cctcaagctc | 7440 |
| tgccaggaca tcttcctggt gcgggagact cgggagctgg agctggagga ggagttgtac | 7500 |
| gccaagctca tcttcctcta ccgctcaccg gagaccatga tcaagtggac tcgtgagaag | 7560 |
| gagtag | 7566 |

<210> SEQ ID NO 2
<211> LENGTH: 2521
<212> TYPE: PRT
<213> ORGANISM: Homo sapiens

<400> SEQUENCE: 2

Met Glu Pro His Val Leu Gly Ala Val Leu Tyr Trp Leu Leu Leu Pro
1               5                   10                  15

Cys Ala Leu Leu Ala Ala Cys Leu Leu Arg Phe Ser Gly Leu Ser Leu
            20                  25                  30

Val Tyr Leu Leu Phe Leu Leu Leu Pro Trp Phe Pro Gly Pro Thr
        35                  40                  45

Arg Cys Gly Leu Gln Gly His Thr Gly Arg Leu Leu Arg Ala Leu Leu
    50                  55                  60

```
Gly Leu Ser Leu Leu Phe Leu Val Ala His Leu Ala Leu Gln Ile Cys
 65                  70                  75                  80

Leu His Ile Val Pro Arg Leu Asp Gln Leu Leu Gly Pro Ser Cys Ser
                 85                  90                  95

Arg Trp Glu Thr Leu Ser Arg His Ile Gly Val Thr Arg Leu Asp Leu
            100                 105                 110

Lys Asp Ile Pro Asn Ala Ile Arg Leu Val Ala Pro Asp Leu Gly Ile
        115                 120                 125

Leu Val Val Ser Ser Val Cys Leu Gly Ile Cys Gly Arg Leu Ala Arg
    130                 135                 140

Asn Thr Arg Gln Ser Pro His Pro Arg Glu Leu Asp Asp Asp Glu Arg
145                 150                 155                 160

Asp Val Asp Ala Ser Pro Thr Ala Gly Leu Gln Glu Ala Ala Thr Leu
                165                 170                 175

Ala Pro Thr Arg Arg Ser Arg Leu Ala Ala Arg Phe Arg Val Thr Ala
            180                 185                 190

His Trp Leu Leu Val Ala Ala Gly Arg Val Leu Ala Val Thr Leu Leu
        195                 200                 205

Ala Leu Ala Gly Ile Ala His Pro Ser Ala Leu Ser Ser Val Tyr Leu
    210                 215                 220

Leu Leu Phe Leu Ala Leu Cys Thr Trp Trp Ala Cys His Phe Pro Ile
225                 230                 235                 240

Ser Thr Arg Gly Phe Ser Arg Leu Cys Val Ala Val Gly Cys Phe Gly
                245                 250                 255

Ala Gly His Leu Ile Cys Leu Tyr Cys Tyr Gln Met Pro Leu Ala Gln
            260                 265                 270

Ala Leu Leu Pro Pro Ala Gly Ile Trp Ala Arg Val Leu Gly Leu Lys
        275                 280                 285

Asp Phe Val Gly Pro Thr Asn Cys Ser Ser Pro His Ala Leu Val Leu
290                 295                 300

Asn Thr Gly Leu Asp Trp Pro Val Tyr Ala Ser Pro Gly Val Leu Leu
305                 310                 315                 320

Leu Leu Cys Tyr Ala Thr Ala Ser Leu Arg Lys Leu Arg Ala Tyr Arg
                325                 330                 335

Pro Ser Gly Gln Arg Lys Glu Ala Ala Lys Gly Tyr Glu Ala Arg Glu
            340                 345                 350

Leu Glu Leu Ala Glu Leu Asp Gln Trp Pro Gln Glu Arg Glu Ser Asp
        355                 360                 365

Gln His Val Val Pro Thr Ala Pro Asp Thr Glu Ala Asp Asn Cys Ile
    370                 375                 380

Val His Glu Leu Thr Gly Gln Ser Ser Val Leu Arg Arg Pro Val Arg
385                 390                 395                 400

Pro Lys Arg Ala Glu Pro Arg Glu Ala Ser Pro Leu His Ser Leu Gly
                405                 410                 415

His Leu Ile Met Asp Gln Ser Tyr Val Cys Ala Leu Ile Ala Met Met
            420                 425                 430

Val Trp Ser Ile Thr Tyr His Ser Trp Leu Thr Phe Val Leu Leu Leu
        435                 440                 445

Trp Ala Cys Leu Ile Trp Thr Val Arg Ser Arg His Gln Leu Ala Met
    450                 455                 460

Leu Cys Ser Pro Cys Ile Leu Leu Tyr Gly Met Thr Leu Cys Cys Leu
465                 470                 475                 480
```

```
Arg Tyr Val Trp Ala Met Asp Leu Arg Pro Glu Leu Pro Thr Thr Leu
                485                 490                 495

Gly Pro Val Ser Leu Arg Gln Leu Gly Leu Glu His Thr Arg Tyr Pro
            500                 505                 510

Cys Leu Asp Leu Gly Ala Met Leu Leu Tyr Thr Leu Thr Phe Trp Leu
            515                 520                 525

Leu Leu Arg Gln Phe Val Lys Glu Lys Leu Leu Lys Trp Ala Glu Ser
        530                 535                 540

Pro Ala Ala Leu Thr Glu Val Thr Val Ala Asp Thr Glu Pro Thr Arg
545                 550                 555                 560

Thr Gln Thr Leu Leu Gln Ser Leu Gly Glu Leu Val Lys Gly Val Tyr
                565                 570                 575

Ala Lys Tyr Trp Ile Tyr Val Cys Ala Gly Met Phe Ile Val Val Ser
            580                 585                 590

Phe Ala Gly Arg Leu Val Val Tyr Lys Ile Val Tyr Met Phe Leu Phe
        595                 600                 605

Leu Leu Cys Leu Thr Leu Phe Gln Val Tyr Tyr Ser Leu Trp Arg Lys
610                 615                 620

Leu Leu Lys Ala Phe Trp Trp Leu Val Val Ala Tyr Thr Met Leu Val
625                 630                 635                 640

Leu Ile Ala Val Tyr Thr Phe Gln Phe Gln Asp Phe Pro Ala Tyr Trp
                645                 650                 655

Arg Asn Leu Thr Gly Phe Thr Asp Glu Gln Leu Gly Asp Leu Gly Leu
            660                 665                 670

Glu Gln Phe Ser Val Ser Glu Leu Phe Ser Ser Ile Leu Val Pro Gly
        675                 680                 685

Phe Phe Leu Leu Ala Cys Ile Leu Gln Leu His Tyr Phe His Arg Pro
690                 695                 700

Phe Met Gln Leu Thr Asp Met Glu His Val Ser Leu Pro Gly Thr Arg
705                 710                 715                 720

Leu Pro Arg Trp Ala His Arg Gln Asp Ala Val Ser Gly Thr Pro Leu
                725                 730                 735

Leu Arg Glu Glu Gln Gln Glu His Gln Gln Gln Gln Glu Glu Glu
            740                 745                 750

Glu Glu Glu Glu Asp Ser Arg Asp Glu Gly Leu Gly Val Ala Thr Pro
        755                 760                 765

His Gln Ala Thr Gln Val Pro Glu Gly Ala Ala Lys Trp Gly Leu Val
770                 775                 780

Ala Glu Arg Leu Leu Glu Leu Ala Ala Gly Phe Ser Asp Val Leu Ser
785                 790                 795                 800

Arg Val Gln Val Phe Leu Arg Arg Leu Leu Glu Leu His Val Phe Lys
                805                 810                 815

Leu Val Ala Leu Tyr Thr Val Trp Val Ala Leu Lys Glu Val Ser Val
            820                 825                 830

Met Asn Leu Leu Leu Val Val Leu Trp Ala Phe Ala Leu Pro Tyr Pro
        835                 840                 845

Arg Phe Arg Pro Met Ala Ser Cys Leu Ser Thr Val Trp Thr Cys Val
850                 855                 860

Ile Ile Val Cys Lys Met Leu Tyr Gln Leu Lys Val Val Asn Pro Gln
865                 870                 875                 880

Glu Tyr Ser Ser Asn Cys Thr Glu Pro Phe Pro Asn Ser Thr Asn Leu
                885                 890                 895
```

-continued

```
Leu Pro Thr Glu Ile Ser Gln Ser Leu Leu Tyr Arg Gly Pro Val Asp
            900                 905                 910

Pro Ala Asn Trp Phe Gly Val Arg Lys Gly Phe Pro Asn Leu Gly Tyr
        915                 920                 925

Ile Gln Asn His Leu Gln Val Leu Leu Leu Val Phe Glu Ala Ile
930                 935                 940

Val Tyr Arg Arg Gln Glu His Tyr Arg Arg Gln His Gln Leu Ala Pro
945                 950                 955                 960

Leu Pro Ala Gln Ala Val Phe Ala Ser Gly Thr Arg Gln Leu Asp
            965                 970                 975

Gln Asp Leu Leu Gly Cys Leu Lys Tyr Phe Ile Asn Phe Phe Tyr
            980                 985                 990

Lys Phe Gly Leu Glu Ile Cys Phe Leu Met Ala Val Asn Val Ile Gly
            995                 1000                1005

Gln Arg Met Asn Phe Leu Val Thr Leu His Gly Cys Trp Leu Val
    1010                1015                1020

Ala Ile Leu Thr Arg Arg His Arg Gln Ala Ile Ala Arg Leu Trp
    1025                1030                1035

Pro Asn Tyr Cys Leu Phe Leu Ala Leu Phe Leu Leu Tyr Gln Tyr
    1040                1045                1050

Leu Leu Cys Leu Gly Met Pro Pro Ala Leu Cys Ile Asp Tyr Pro
    1055                1060                1065

Trp Arg Trp Ser Arg Ala Val Pro Met Asn Ser Ala Leu Ile Lys
    1070                1075                1080

Trp Leu Tyr Leu Pro Asp Phe Phe Arg Ala Pro Asn Ser Thr Asn
    1085                1090                1095

Leu Ile Ser Asp Phe Leu Leu Leu Cys Ala Ser Gln Gln Trp
    1100                1105                1110

Gln Val Phe Ser Ala Glu Arg Thr Glu Glu Trp Gln Arg Met Ala
    1115                1120                1125

Gly Val Asn Thr Asp Arg Leu Glu Pro Leu Arg Gly Glu Pro Asn
    1130                1135                1140

Pro Val Pro Asn Phe Ile His Cys Arg Ser Tyr Leu Asp Met Leu
    1145                1150                1155

Lys Val Ala Val Phe Arg Tyr Leu Phe Trp Leu Val Leu Val Val
    1160                1165                1170

Val Phe Val Thr Gly Ala Thr Arg Ile Ser Ile Phe Gly Leu Gly
    1175                1180                1185

Tyr Leu Leu Ala Cys Phe Tyr Leu Leu Leu Phe Gly Thr Ala Leu
    1190                1195                1200

Leu Gln Arg Asp Thr Arg Ala Arg Leu Val Leu Trp Asp Cys Leu
    1205                1210                1215

Ile Leu Tyr Asn Val Thr Val Ile Ile Ser Lys Asn Met Leu Ser
    1220                1225                1230

Leu Leu Ala Cys Val Phe Val Glu Gln Met Gln Thr Gly Phe Cys
    1235                1240                1245

Trp Val Ile Gln Leu Phe Ser Leu Val Cys Thr Val Lys Gly Tyr
    1250                1255                1260

Tyr Asp Pro Lys Glu Met Met Asp Arg Asp Gln Asp Cys Leu Leu
    1265                1270                1275

Pro Val Glu Glu Ala Gly Ile Ile Trp Asp Ser Val Cys Phe Phe
    1280                1285                1290
```

```
Phe Leu Leu Leu Gln Arg Arg Val Phe Leu Ser His Tyr Tyr Leu
1295                1300                1305

His Val Arg Ala Asp Leu Gln Ala Thr Ala Leu Leu Ala Ser Arg
1310                1315                1320

Gly Phe Ala Leu Tyr Asn Ala Ala Asn Leu Lys Ser Ile Asp Phe
1325                1330                1335

His Arg Arg Ile Glu Glu Lys Ser Leu Ala Gln Leu Lys Arg Gln
1340                1345                1350

Met Glu Arg Ile Arg Ala Lys Gln Glu Lys His Arg Gln Gly Arg
1355                1360                1365

Val Asp Arg Ser Arg Pro Gln Asp Thr Leu Gly Pro Lys Asp Pro
1370                1375                1380

Gly Leu Glu Pro Gly Pro Asp Ser Pro Gly Ser Ser Pro Pro
1385                1390                1395

Arg Arg Gln Trp Trp Arg Pro Trp Leu Asp His Ala Thr Val Ile
1400                1405                1410

His Ser Gly Asp Tyr Phe Leu Phe Glu Ser Asp Ser Glu Glu Glu
1415                1420                1425

Glu Glu Ala Val Pro Glu Asp Pro Arg Pro Ser Ala Gln Ser Ala
1430                1435                1440

Phe Gln Leu Ala Tyr Gln Ala Trp Val Thr Asn Ala Gln Ala Val
1445                1450                1455

Leu Arg Arg Arg Gln Gln Glu Gln Glu Gln Ala Arg Gln Glu Gln
1460                1465                1470

Ala Gly Gln Leu Pro Thr Gly Gly Gly Pro Ser Gln Glu Val Glu
1475                1480                1485

Pro Ala Glu Gly Pro Glu Glu Ala Ala Ala Gly Arg Ser His Val
1490                1495                1500

Val Gln Arg Val Leu Ser Thr Ala Gln Phe Leu Trp Met Leu Gly
1505                1510                1515

Gln Ala Leu Val Asp Glu Leu Thr Arg Trp Leu Gln Glu Phe Thr
1520                1525                1530

Arg His His Gly Thr Met Ser Asp Val Leu Arg Ala Glu Arg Tyr
1535                1540                1545

Leu Leu Thr Gln Glu Leu Leu Gln Gly Gly Glu Val His Arg Gly
1550                1555                1560

Val Leu Asp Gln Leu Tyr Thr Ser Gln Ala Glu Ala Thr Leu Pro
1565                1570                1575

Gly Pro Thr Glu Ala Pro Asn Ala Pro Ser Thr Val Ser Ser Gly
1580                1585                1590

Leu Gly Ala Glu Glu Pro Leu Ser Ser Met Thr Asp Asp Met Gly
1595                1600                1605

Ser Pro Leu Ser Thr Gly Tyr His Thr Arg Ser Gly Ser Glu Glu
1610                1615                1620

Ala Val Thr Asp Pro Gly Glu Arg Glu Ala Gly Ala Ser Leu Tyr
1625                1630                1635

Gln Gly Leu Met Arg Thr Ala Ser Glu Leu Leu Leu Asp Arg Arg
1640                1645                1650

Leu Arg Ile Pro Glu Leu Glu Glu Ala Glu Leu Phe Ala Glu Gly
1655                1660                1665

Gln Gly Arg Ala Leu Arg Leu Leu Arg Ala Val Tyr Gln Cys Val
1670                1675                1680
```

-continued

Ala Ala His Ser Glu Leu Leu Cys Tyr Phe Ile Ile Ile Leu Asn
1685                1690                1695

His Met Val Thr Ala Ser Ala Gly Ser Leu Val Leu Pro Val Leu
1700                1705                1710

Val Phe Leu Trp Ala Met Leu Ser Ile Pro Arg Pro Ser Lys Arg
1715                1720                1725

Phe Trp Met Thr Ala Ile Val Phe Thr Glu Ile Ala Val Val Val
1730                1735                1740

Lys Tyr Leu Phe Gln Phe Gly Phe Phe Pro Trp Asn Ser His Val
1745                1750                1755

Val Leu Arg Arg Tyr Glu Asn Lys Pro Tyr Phe Pro Pro Arg Ile
1760                1765                1770

Leu Gly Leu Glu Lys Thr Asp Gly Tyr Ile Lys Tyr Asp Leu Val
1775                1780                1785

Gln Leu Met Ala Leu Phe Phe His Arg Ser Gln Leu Leu Cys Tyr
1790                1795                1800

Gly Leu Trp Asp His Glu Glu Asp Ser Pro Ser Lys Glu His Asp
1805                1810                1815

Lys Ser Gly Glu Glu Glu Gln Gly Ala Glu Glu Gly Pro Gly Val
1820                1825                1830

Pro Ala Ala Thr Thr Glu Asp His Ile Gln Val Glu Ala Arg Val
1835                1840                1845

Gly Pro Thr Asp Gly Thr Pro Glu Pro Gln Val Glu Leu Arg Pro
1850                1855                1860

Arg Asp Thr Arg Arg Ile Ser Leu Arg Phe Arg Arg Arg Lys Lys
1865                1870                1875

Glu Gly Pro Ala Arg Lys Gly Ala Ala Ala Ile Glu Ala Glu Asp
1880                1885                1890

Arg Glu Glu Glu Gly Glu Glu Glu Lys Glu Ala Pro Thr Gly
1895                1900                1905

Arg Glu Lys Arg Pro Ser Arg Ser Gly Gly Arg Val Arg Ala Ala
1910                1915                1920

Gly Arg Arg Leu Gln Gly Phe Cys Leu Ser Leu Ala Gln Gly Thr
1925                1930                1935

Tyr Arg Pro Leu Arg Arg Phe Phe His Asp Ile Leu His Thr Lys
1940                1945                1950

Tyr Arg Ala Ala Thr Asp Val Tyr Ala Leu Met Phe Leu Ala Asp
1955                1960                1965

Val Val Asp Phe Ile Ile Ile Phe Gly Phe Trp Ala Phe Gly
1970                1975                1980

Lys His Ser Ala Ala Thr Asp Ile Thr Ser Ser Leu Ser Asp Asp
1985                1990                1995

Gln Val Pro Glu Ala Phe Leu Val Met Leu Leu Ile Gln Phe Ser
2000                2005                2010

Thr Met Val Val Asp Arg Ala Leu Tyr Leu Arg Lys Thr Val Leu
2015                2020                2025

Gly Lys Leu Ala Phe Gln Val Ala Leu Val Leu Ala Ile His Leu
2030                2035                2040

Trp Met Phe Phe Ile Leu Pro Ala Val Thr Glu Arg Met Phe Asn
2045                2050                2055

Gln Asn Val Val Ala Gln Leu Trp Tyr Phe Val Lys Cys Ile Tyr
2060                2065                2070

```
Phe Ala Leu Ser Ala Tyr Gln Ile Arg Cys Gly Tyr Pro Thr Arg
    2075            2080            2085

Ile Leu Gly Asn Phe Leu Thr Lys Lys Tyr Asn His Leu Asn Leu
    2090            2095            2100

Phe Leu Phe Gln Gly Phe Arg Leu Val Pro Phe Leu Val Glu Leu
    2105            2110            2115

Arg Ala Val Met Asp Trp Val Trp Thr Asp Thr Thr Leu Ser Leu
    2120            2125            2130

Ser Ser Trp Met Cys Val Glu Asp Ile Tyr Ala Asn Ile Phe Ile
    2135            2140            2145

Ile Lys Cys Ser Arg Glu Thr Glu Lys Lys Tyr Pro Gln Pro Lys
    2150            2155            2160

Gly Gln Lys Lys Lys Lys Ile Val Lys Tyr Gly Met Gly Gly Leu
    2165            2170            2175

Ile Ile Leu Phe Leu Ile Ala Ile Ile Trp Phe Pro Leu Leu Phe
    2180            2185            2190

Met Ser Leu Val Arg Ser Val Val Gly Val Val Asn Gln Pro Ile
    2195            2200            2205

Asp Val Thr Val Thr Leu Lys Leu Gly Gly Tyr Glu Pro Leu Phe
    2210            2215            2220

Thr Met Ser Ala Gln Gln Pro Ser Ile Ile Pro Phe Thr Ala Gln
    2225            2230            2235

Ala Tyr Glu Glu Leu Ser Arg Gln Phe Asp Pro Gln Pro Leu Ala
    2240            2245            2250

Met Gln Phe Ile Ser Gln Tyr Ser Pro Glu Asp Ile Val Thr Ala
    2255            2260            2265

Gln Ile Glu Gly Ser Ser Gly Ala Leu Trp Arg Ile Ser Pro Pro
    2270            2275            2280

Ser Arg Ala Gln Met Lys Arg Glu Leu Tyr Asn Gly Thr Ala Asp
    2285            2290            2295

Ile Thr Leu Arg Phe Thr Trp Asn Phe Gln Arg Asp Leu Ala Lys
    2300            2305            2310

Gly Gly Thr Val Glu Tyr Ala Asn Glu Lys His Met Leu Ala Leu
    2315            2320            2325

Ala Pro Asn Ser Thr Ala Arg Arg Gln Leu Ala Ser Leu Leu Glu
    2330            2335            2340

Gly Thr Ser Asp Gln Ser Val Val Ile Pro Asn Leu Phe Pro Lys
    2345            2350            2355

Tyr Ile Arg Ala Pro Asn Gly Pro Glu Ala Asn Pro Val Lys Gln
    2360            2365            2370

Leu Gln Pro Asn Glu Glu Ala Asp Tyr Leu Gly Val Arg Ile Gln
    2375            2380            2385

Leu Arg Arg Glu Gln Gly Ala Gly Ala Thr Gly Phe Leu Glu Trp
    2390            2395            2400

Trp Val Ile Glu Leu Gln Glu Cys Arg Thr Asp Cys Asn Leu Leu
    2405            2410            2415

Pro Met Val Ile Phe Ser Asp Lys Val Ser Pro Pro Ser Leu Gly
    2420            2425            2430

Phe Leu Ala Gly Tyr Gly Ile Met Gly Leu Tyr Val Ser Ile Val
    2435            2440            2445

Leu Val Ile Gly Lys Phe Val Arg Gly Phe Phe Ser Glu Ile Ser
    2450            2455            2460
```

| His | Ser | Ile | Met | Phe | Glu | Glu | Leu | Pro | Cys | Val | Asp | Arg | Ile | Leu |
|     | 2465 |     |     |     | 2470 |     |     |     | 2475 |     |     |     |     |     |

| Lys | Leu | Cys | Gln | Asp | Ile | Phe | Leu | Val | Arg | Glu | Thr | Arg | Glu | Leu |
|     | 2480 |     |     |     | 2485 |     |     |     | 2490 |     |     |     |     |     |

| Glu | Leu | Glu | Glu | Glu | Leu | Tyr | Ala | Lys | Leu | Ile | Phe | Leu | Tyr | Arg |
|     | 2495 |     |     |     | 2500 |     |     |     | 2505 |     |     |     |     |     |

| Ser | Pro | Glu | Thr | Met | Ile | Lys | Trp | Thr | Arg | Glu | Lys | Glu |
|     | 2510 |     |     |     | 2515 |     |     |     | 2520 |     |     |     |

<210> SEQ ID NO 3
<211> LENGTH: 8259
<212> TYPE: DNA
<213> ORGANISM: Homo sapiens

<400> SEQUENCE: 3

```
atggcctcag aagtggtgtg cgggctcatc ttcaggctgc tgctgcccat ctgcctggca      60
gtagcatgtg cattccgata caatgggctc tcctttgtct accttatcta cctcttgctc     120
attcctctgt tctcagaacc aacaaaaacg acgatgcaag acatacgggg acggttatta     180
aagtctctgt gcttcatcag tctttccttc ctgttgctgc atcattttt ccacatcacg      240
ttggtgagcc ttgaagctca acatcgtatt gcacctggct acaactgctc aacatgggaa     300
aagacattcc ggcagatcgg cttttgaaagc ttaaagggag ctgatgctgg caatgggatc    360
agagtgtttg tacctgacat cgggatgttc attgctagtc tgaccatctg ctcctctgt      420
agaaacattg ttcagaaacc tgtgacagac gaagcagcac agagtaaccc ggagtttgaa     480
aatgaagaat tggctgaagg agaaaaaatt gattcagaag aggcactgat ctatgaagag     540
gatttcaatg gaggagatgg tgttgaaggc gagttggaag aaagcacgaa gttaaaaatg     600
ttccgcaggc ttgcctctgt ggcctctaag ctcaaggagt tcattggcaa catgatcacc     660
actgctggga aagtcgttgt taccatctta ctgggctcct cgggcatgat gttgccgtct     720
ttgacatcat ctgtgtattt ttttgtattt ttgggtctgt gcacctggtg gtcctggtgc     780
cggacgttcg acccattgct gttcagctgt ctctgtgttc tgctggctat tttcactgct     840
ggacatttga ttggacttta tttataccag ttccaattct ttcaagaggc agttccaccc    900
aatgactact atgcaaggtt gtttggtatc aagtcagtaa ttcaaacgga ctgttcaagt     960
acttggaaga tcatagtgaa cccggacctg tcgtggtacc accacgccaa ccctatcctc   1020
ctgctggtga tgtactacac tctggccact ctgatccgca tctggctgca agagcccctt   1080
gtgcaggatg agggggaccaa agaagaggac aaagccctgg cttgtagccc catccaaata  1140
acagcgggga ggaggcggag cctgtggtac gcaaccccatt accccactga tgagagaaaa   1200
cttttatcca tgacccagga tgactacaaa ccatctgatg cctgctggt gactgtgaac    1260
ggcaaccccg tggattacca caccatccac ccaagcctgc ccatggagaa cggccctggc   1320
aaagccgacc tctactccac ccctcagtac cggtgggagc cctctgatga atcctcagaa   1380
aagcgagagg aggaagagga agagaaagaa gaatttgaag aagaaggag ccgtgaggaa    1440
aaaagaagta tcaaagttca tgccatggtc tccgtattcc aatttattat gaaacaaagt   1500
tacatctgtg ccctcatagc tatgatggcc tggagcatca cctatcacag ctggctgacc   1560
ttcgtgctgc tgatctggtc gtgcactctt tggatgattc gcaacagaag aaaatatgcc   1620
atgatcagct ctcccttcat ggtggtttat ggaaacctat tgttgatatt acagtatata   1680
tggagttttg aacttcctga aattaaaaaa gttccaggat tttagaaaaa gaaagagcca  1740
```

```
ggagaacttg cttccaaaat ccttttcacc attacttttt ggctactgct gaggcagcac    1800
ctcacagagc aaaaagctct gcaagaaaag gaagctcttt tatcggaagt caaaattggc    1860
agtcaggaaa atgaagaaaa agatgaggaa cttcaagata tacaagtgga aggagagccc    1920
aaagaggagg aagaagagga agcgaaggaa gagaagcaag agagaaagaa ggtagagcaa    1980
gaggaagctg aagaagaaga tgagcaggac atcatgaaag tcctgggcaa tctggtggtg    2040
gccatgttca tcaagtactg gatctacgtc tgcggaggca tgttcttctt cgtcagcttc    2100
gagggtaaaa tcgtaatgta caaaatcatc tacatggtgc tgttcctgtt ctgtgtggcc    2160
ctataccagg tgcactatga atggtggagg aaaattctaa atattttttg gatgtcagtg    2220
gttatttaca ctatgctggt gcttatcttt atatacacat atcagtttga gaacttccca    2280
ggcctgtggc aaaatatgac tggactgaaa aagaaaagc ttgaggatct tggcttaaag    2340
cagtttactg tggctgaact attcactcgc atattcatcc aacctccttt tctgctggtg    2400
tgcattttac acctgcacta cttccatgac cggttccttg aactcacaga cctcaagtcc    2460
attcccagca aagaagacaa caccatctac agactggccc acccggaagg aagcctcccg    2520
gacctcacca tgatgcatct gactgccagc ctggagaagc cggaggtgag gaagttggct    2580
gagcctgggg aggagaagct tgagggctac tctgaaaaag cccagaaggg tgatcttggg    2640
aaagacagcg aggagtcaga ggaggacgga gaggaagagg aggaatccga ggaggaggaa    2700
gaaacatcag acttaaggaa caaatggcac ctggtgattg accgcctcac tgtgctcttc    2760
ttaaaattcc tggagtattt tcacaagctg caggtgttca tgtggtggat tttggagttg    2820
cacatcatca aaatcgtttc ctcttacatt atctgggttt ctgtgaaaga ggtgtctctg    2880
ttcaactatg tatttttgat ttcttgggct tttgctctgc cgtacgccaa gctgcgccgt    2940
ctggcttcaa gtgtctgcac agtctggacg tgtgtgatca tcgtctgcaa aatgttgtac    3000
cagctccaaa ccattaagcc tgagaacttc tctgttaact gttccttgcc aaatgaaaat    3060
caaacaaaca tccccttaa tgagttgaac aagtctctgc tctacagcgc tcctatcgat    3120
cctacagagt gggtcggcct gcggaagtct tcgcctctgc tagtctacct gaggaataac    3180
ctcctgatgc tggctatcct ggccttgaa gtcaccattt accgccatca ggaatactat    3240
cgaggtcgaa ataacctgac ggcccctgtg tctagaacta tctttcatga cattacaaga    3300
ctacatctag atgatggact tattaattgt gccaaatatt tcattaatta cttcttttac    3360
aagtttggtc tggagacctg tttcctaatg tcagttaacg tcattggcca gcgaatggat    3420
ttctatgcca tgatccacgc ctgctggctg atcgctgtct tatatagacg cagaaggaaa    3480
gccatcgcag agatctggcc caagtactgc tgcttcctgg catgcatcat caccttccag    3540
tatttcatct gcattggcat cccacctgct ccttgccgag attacccgtg agattcaag    3600 ggtgccagct tcaatgacaa catcataaag tggctgtact tcccagattt cattgtgcgg    3660
cccaaccctg tgtttctcgt ctatgacttc atgctgcttc tgtgtgcctc cttacaacgg    3720
cagatttttg aggatgagaa caaggctgca gtgcgaatca tggcaggtga caatgtcgag    3780
atctgcatga accttgatgc ggcctccttc agccaacata accctgtgcc agattttatt    3840
cactgcagat cttacttaga catgtccaaa gtgatcatct tcagctacct cttctggttt    3900
gtgctcacca tcatcttcat cactgggacc accaggatca gcatctttg catggggtac    3960 ctggtggcct gtttctactt cctgctcttt ggggcgatt tgctgttgaa acccatcaag    4020
agcatcctgc gctactggga ctggctgatc gcatacaacg ttttgtgat tacgatgaaa    4080 aatatcctgt caataggagc atgtggatac attggaacat tggtgcacaa tagttgttgg    4140
```

```
ttgatccagg ctttcagcct ggcctgcaca gtcaaaggct atcaaatgcc tgctgctaat    4200
tcaccctgta cacttcccag tggggaagca ggaatcattt gggacagcat atgttttgcc    4260
ttcctcctgc tgcaaagaag agttttcatg agttattatt ttctacatgt tgtggctgat    4320
ataaaagctt cccagattct ggcatcaaga ggagctgaac ttttccaggc cacaattgta    4380
aaagctgtaa aggcaagaat tgaggaagag aagaagtcca tggaccagct gaagcgacag    4440
atggatcgca tcaaggccag gcaacagaaa tataaaaagg gtaaggagag gatgctgagc    4500
ttgacccagg agccagggga aggccaggac atgcaaaaac tctctgaaga ggatgatgaa    4560
agagaagcag acaaacagaa agccaagggc aaaaaaaagc agtggtggcg gccttgggtt    4620
gatcatgctt ccatggtcag gagtggagat tattatttgt ttgaaacgga tagtgaagag    4680
gaggaagagg aagaattaaa gaaggaagat gaagaacctc cacgaaggtc agcattccag    4740
tttgtttatc aagcctggat tactgatcct aaaacagcac tccgacaaag acacaaagag    4800
aaaaaaaggt ctgcaagaga agaacggaaa cgaaggcgga aaggatccaa ggagggtcct    4860
gtggaatggg aagaccggga ggatgaacca atcaaaaaga aatccgatgg accagataat    4920
atcatcaaga ggatatttaa tattttgaaa tttacctggg tcctatttct ggcaacagtg    4980
gacagtttca ctacttggct taactccatt tcaagggagc atattgatat atctacagtt    5040
ctgagaattg aacgatgcat gctgaccaga gaaattaaga agggcaatgt tccaactcgg    5100
gagagcatcc acatgtacta tcagaaccac atcatgaacc tttccagaga gtcgggactg    5160
gacaccattg acgagcatcc cggagctgct tcaggtgcac agacagccca caggatggat    5220
agtttagatt cacatgacag tatctccagc gagcccacgc agtgtaccat gctgtactca    5280
cgccagggga ccactgagac catcgaggag gtggaggctg agcaggagga ggaggcaggg    5340
agcacggcgc ctgagcccag ggaggccaag gagtacgagg ccactgggta cgatgtggga    5400
gccatgggtg ccgaggaggc cagcctcacc ccagaggaag agctgacaca gttctccacc    5460
ttggacgggg atgtggaggc cccacccctcc tacagcaagg ctgtgagctt cgagcatctg    5520
tccttcggct cgcaggacga ctctgcaggc aagaaccgta tggcagtcag cccggacgac    5580
agccgcaccg acaagctggg gtccagcatc ttacctcccc tgacccatga gctgacggcc    5640
agcgagctgc tgctgaaaaa gatgtttcac gacgatgagc ttgaagagtc agagaaattc    5700
tacgtggggc agccccgatt tctgctgctc ttctatgcca tgtacaatac cctggtggcc    5760
cgctcggaga tggtgtgcta cttcgtgatc atcctcaacc acatggtctc tgcctccatg    5820
atcacgctcc tgcttcccat cctcatcttc ctctgggcca tgttgtccgt ccccaggccc    5880
agccgccggt tctggatgat ggccatcgtc tatactgagg tggcaattgt agtcaagtat    5940
ttcttccaat ttgggttctt tccctggaat aagaatgtgg aggtgaacaa agataaaccg    6000
tatcaccccc caaacatcat aggagtggaa aagaaggaag gttatgttct ctatgacctc    6060
atccagctcc tggctctgtt ctttcatcga tcaattttga agtgccatgg cttatgggat    6120
gaagatgaca tgactgaaag tggcatggcc agggaggaat cagatgatga gctctccctc    6180
ggtcatggca ggagggactc ctccgattct ctcaagtcca tcaacctggc cgcgtctgtg    6240
gagtcagtgc atgtgacctt cccggagcag cagacagctg tccggaggaa cgctccggcc    6300
agcagctccg agccatccca gagatccagc ttttcttcaa acagatccca agaggcagc    6360 acaagcaccc gaaacagcag tcaaaaagga agcagtgttt tgagtattaa gcaaaaaggc    6420
aaaagggaac tttatatgga aaagcttcaa gaacatttaa tcaaagcaaa agcctttacc    6480
```

-continued

```
ataaagaaga cgctggagat ctatgtgccc atcaaacagt tcttttacaa cctcatccac    6540
ccggagtata gcgccgtgac tgacgtgtat gtactcatgt tcctggctga cactgtggac    6600
ttcatcatca ttgtcttcgg cttttgggcc tttgggaaac actcagcagc tgcagacatc    6660
acctcttcac tgtcagagga ccaggtcccg gggccgtttt tggtgatggt cctcattcag    6720
tttggaacca tggtggtgga ccgagccctc tacctcagga agactgtact gggaaaggtc    6780
atcttccagg tcattcttgt gttcggaatt cacttctgga tgttcttcat cttacctggt    6840
gtgactgaga ggaaattcag ccagaacctg gttgcccagc tttggtactt tgtgaaatgt    6900
gtttacttcg ggttgtctgc ttaccagatc cgttgtggct acccaacgcg agtcctgggg    6960
aacttcctca ccaagagcta caattacgtc aacctcttct tattccaagg gtttcgcctc    7020
gtgcccttt tgactgagct gagggcagtg atggactggg tgtggacgga cacaactttg    7080
agcctgtcca gctggatctg tgtggaggac atctatgctc acatattcat cctgaagtgt    7140
tggcgggagt cggagaagag ataccctcag ccacggggcc agaagaagaa gaaagtggtg    7200
aagtatggca tgggaggaat gatcatcgtc ctgctcatct gcattgtctg gtttcctctt    7260
ctcttcatgt ctttgatcaa atctgtggct ggggtcatca accagcccct ggacgtctcc    7320
gtcacaatta ccctgggagg gtatcagcct attttcacaa tgagtgccca acaaagccag    7380
ttgaaagtta tggaccagca gagctttaac aaatttatac aagcttttc tagggacacc    7440
ggtgctatgc aatttctgga aaattatgaa aagaagaca taacagtagc agaactggaa    7500
ggaaactcaa attctttgtg gaccatcagc ccacccagta agcagaaaat gatacacgaa    7560
ctcctggacc ccaatagtag cttctctgtt gttttttcat ggagtattca gagaaactta    7620
agtctgggtg caaaatcgga aatagcaaca gataagcttt cttttcctct taaaaatatt    7680
actcgaaaga atatcgctaa aatgatagca ggcaacagca cagaaagttc aaaaacacca    7740
gtgaccatag aaaagattta tccatattat gtgaaagcac tagtgattc taactcaaaa    7800
cctataaagc aactttatc tgaaaataat ttcatggata ttaccatcat tttgtccaga    7860
gacaatacaa ctaaatataa cagtgagtgg tgggttctca acctgactgg aaacagaata    7920
tacaatccga actctcaggc cctggaactg gtggtcttca atgacaaagt cagtccccca    7980
agtctggggt tcctggctgg ctatggtatt atgggattat atgcttcagt tgtccttgtg    8040
attgggaaat ttgtccgtga attcttcagt gggatttctc actccatcat gtttgaagag    8100
cttccaaatg tggatcgaat tttgaagttg tgcacagata ttttttttagt tcgagagaca    8160
ggagaactgg agctagaaga agatctctat gccaaattaa tattcctata tcgctcacca    8220
gagacaatga tcaaatggac tagagaaaaa acaaattga                            8259
```

<210> SEQ ID NO 4
<211> LENGTH: 2752
<212> TYPE: PRT
<213> ORGANISM: Homo sapiens

<400> SEQUENCE: 4

```
Met Ala Ser Glu Val Val Cys Gly Leu Ile Phe Arg Leu Leu Leu Pro
1               5                   10                  15

Ile Cys Leu Ala Val Ala Cys Ala Phe Arg Tyr Asn Gly Leu Ser Phe
            20                  25                  30

Val Tyr Leu Ile Tyr Leu Leu Leu Ile Pro Leu Phe Ser Glu Pro Thr
        35                  40                  45

Lys Thr Thr Met Gln Gly His Thr Gly Arg Leu Leu Lys Ser Leu Cys
    50                  55                  60
```

-continued

```
Phe Ile Ser Leu Ser Phe Leu Leu His Ile Ile Phe His Ile Thr
65                  70                  75                  80

Leu Val Ser Leu Glu Ala Gln His Arg Ile Ala Pro Gly Tyr Asn Cys
                85                  90                  95

Ser Thr Trp Glu Lys Thr Phe Arg Gln Ile Gly Phe Glu Ser Leu Lys
            100                 105                 110

Gly Ala Asp Ala Gly Asn Gly Ile Arg Val Phe Val Pro Asp Ile Gly
        115                 120                 125

Met Phe Ile Ala Ser Leu Thr Ile Trp Leu Leu Cys Arg Asn Ile Val
130                 135                 140

Gln Lys Pro Val Thr Asp Glu Ala Ala Gln Ser Asn Pro Glu Phe Glu
145                 150                 155                 160

Asn Glu Glu Leu Ala Glu Gly Glu Lys Ile Asp Ser Glu Glu Ala Leu
                165                 170                 175

Ile Tyr Glu Glu Asp Phe Asn Gly Gly Asp Gly Val Glu Gly Glu Leu
            180                 185                 190

Glu Glu Ser Thr Lys Leu Lys Met Phe Arg Arg Leu Ala Ser Val Ala
        195                 200                 205

Ser Lys Leu Lys Glu Phe Ile Gly Asn Met Ile Thr Thr Ala Gly Lys
210                 215                 220

Val Val Val Thr Ile Leu Leu Gly Ser Ser Gly Met Met Leu Pro Ser
225                 230                 235                 240

Leu Thr Ser Ser Val Tyr Phe Phe Val Phe Leu Gly Leu Cys Thr Trp
                245                 250                 255

Trp Ser Trp Cys Arg Thr Phe Asp Pro Leu Leu Phe Ser Cys Leu Cys
            260                 265                 270

Val Leu Leu Ala Ile Phe Thr Ala Gly His Leu Ile Gly Leu Tyr Leu
        275                 280                 285

Tyr Gln Phe Gln Phe Phe Gln Glu Ala Val Pro Pro Asn Asp Tyr Tyr
290                 295                 300

Ala Arg Leu Phe Gly Ile Lys Ser Val Ile Gln Thr Asp Cys Ser Ser
305                 310                 315                 320

Thr Trp Lys Ile Ile Val Asn Pro Asp Leu Ser Trp Tyr His His Ala
                325                 330                 335

Asn Pro Ile Leu Leu Leu Val Met Tyr Tyr Thr Leu Ala Thr Leu Ile
            340                 345                 350

Arg Ile Trp Leu Gln Glu Pro Leu Val Gln Asp Glu Gly Thr Lys Glu
        355                 360                 365

Glu Asp Lys Ala Leu Ala Cys Ser Pro Ile Gln Ile Thr Ala Gly Arg
370                 375                 380

Arg Arg Ser Leu Trp Tyr Ala Thr His Tyr Pro Thr Asp Glu Arg Lys
385                 390                 395                 400

Leu Leu Ser Met Thr Gln Asp Asp Tyr Lys Pro Ser Asp Gly Leu Leu
                405                 410                 415

Val Thr Val Asn Gly Asn Pro Val Asp Tyr His Thr Ile His Pro Ser
            420                 425                 430

Leu Pro Met Glu Asn Gly Pro Gly Lys Ala Asp Leu Tyr Ser Thr Pro
        435                 440                 445

Gln Tyr Arg Trp Glu Pro Ser Asp Glu Ser Ser Glu Lys Arg Glu Glu
450                 455                 460

Glu Glu Glu Glu Lys Glu Glu Phe Glu Glu Arg Ser Arg Glu Glu
465                 470                 475                 480
```

```
Lys Arg Ser Ile Lys Val His Ala Met Val Ser Val Phe Gln Phe Ile
                485                 490                 495
Met Lys Gln Ser Tyr Ile Cys Ala Leu Ile Ala Met Met Ala Trp Ser
            500                 505                 510
Ile Thr Tyr His Ser Trp Leu Thr Phe Val Leu Leu Ile Trp Ser Cys
        515                 520                 525
Thr Leu Trp Met Ile Arg Asn Arg Arg Lys Tyr Ala Met Ile Ser Ser
530                 535                 540
Pro Phe Met Val Val Tyr Gly Asn Leu Leu Leu Ile Leu Gln Tyr Ile
545                 550                 555                 560
Trp Ser Phe Glu Leu Pro Glu Ile Lys Lys Val Pro Gly Phe Leu Glu
                565                 570                 575
Lys Lys Glu Pro Gly Glu Leu Ala Ser Lys Ile Leu Phe Thr Ile Thr
            580                 585                 590
Phe Trp Leu Leu Leu Arg Gln His Leu Thr Glu Gln Lys Ala Leu Gln
        595                 600                 605
Glu Lys Glu Ala Leu Leu Ser Glu Val Lys Ile Gly Ser Gln Glu Asn
610                 615                 620
Glu Glu Lys Asp Glu Glu Leu Gln Asp Ile Gln Val Glu Gly Glu Pro
625                 630                 635                 640
Lys Glu Glu Glu Glu Glu Ala Lys Glu Glu Lys Gln Glu Arg Lys
                645                 650                 655
Lys Val Glu Gln Glu Glu Ala Glu Glu Asp Glu Gln Asp Ile Met
            660                 665                 670
Lys Val Leu Gly Asn Leu Val Val Ala Met Phe Ile Lys Tyr Trp Ile
        675                 680                 685
Tyr Val Cys Gly Gly Met Phe Phe Val Ser Phe Glu Gly Lys Ile
            690                 695                 700
Val Met Tyr Lys Ile Ile Tyr Met Val Leu Phe Leu Phe Cys Val Ala
705                 710                 715                 720
Leu Tyr Gln Val His Tyr Glu Trp Trp Arg Lys Ile Leu Lys Tyr Phe
                725                 730                 735
Trp Met Ser Val Val Ile Tyr Thr Met Leu Val Leu Ile Phe Ile Tyr
            740                 745                 750
Thr Tyr Gln Phe Glu Asn Phe Pro Gly Leu Trp Gln Asn Met Thr Gly
        755                 760                 765
Leu Lys Lys Glu Lys Leu Glu Asp Leu Gly Leu Lys Gln Phe Thr Val
770                 775                 780
Ala Glu Leu Phe Thr Arg Ile Phe Ile Pro Thr Ser Phe Leu Leu Val
785                 790                 795                 800
Cys Ile Leu His Leu His Tyr Phe His Asp Arg Phe Leu Glu Leu Thr
                805                 810                 815
Asp Leu Lys Ser Ile Pro Ser Lys Glu Asp Asn Thr Ile Tyr Arg Leu
            820                 825                 830
Ala His Pro Glu Gly Ser Leu Pro Asp Leu Thr Met Met His Leu Thr
        835                 840                 845
Ala Ser Leu Glu Lys Pro Glu Val Arg Lys Leu Ala Glu Pro Gly Glu
850                 855                 860
Glu Lys Leu Glu Gly Tyr Ser Glu Lys Ala Gln Lys Gly Asp Leu Gly
865                 870                 875                 880
Lys Asp Ser Glu Glu Ser Glu Glu Asp Gly Glu Glu Glu Glu Ser
                885                 890                 895
```

```
Glu Glu Glu Glu Glu Thr Ser Asp Leu Arg Asn Lys Trp His Leu Val
            900                 905                 910

Ile Asp Arg Leu Thr Val Leu Phe Leu Lys Phe Leu Glu Tyr Phe His
        915                 920                 925

Lys Leu Gln Val Phe Met Trp Trp Ile Leu Gly Leu His Ile Ile Lys
        930                 935                 940

Ile Val Ser Ser Tyr Ile Ile Trp Val Ser Val Lys Glu Val Ser Leu
945                 950                 955                 960

Phe Asn Tyr Val Phe Leu Ile Ser Trp Ala Phe Ala Leu Pro Tyr Ala
                965                 970                 975

Lys Leu Arg Arg Leu Ala Ser Ser Val Cys Thr Val Trp Thr Cys Val
            980                 985                 990

Ile Ile Val Cys Lys Met Leu Tyr Gln Leu Gln Thr Ile Lys Pro Glu
            995                 1000                1005

Asn Phe Ser Val Asn Cys Ser Leu Pro Asn Glu Asn Gln Thr Asn
        1010                1015                1020

Ile Pro Phe Asn Glu Leu Asn Lys Ser Leu Leu Tyr Ser Ala Pro
        1025                1030                1035

Ile Asp Pro Thr Glu Trp Val Gly Leu Arg Lys Ser Ser Pro Leu
        1040                1045                1050

Leu Val Tyr Leu Arg Asn Asn Leu Leu Met Leu Ala Ile Leu Ala
        1055                1060                1065

Phe Glu Val Thr Ile Tyr Arg His Gln Glu Tyr Tyr Arg Gly Arg
        1070                1075                1080

Asn Asn Leu Thr Ala Pro Val Ser Arg Thr Ile Phe His Asp Ile
        1085                1090                1095

Thr Arg Leu His Leu Asp Asp Gly Leu Ile Asn Cys Ala Lys Tyr
        1100                1105                1110

Phe Ile Asn Tyr Phe Phe Tyr Lys Phe Gly Leu Glu Thr Cys Phe
        1115                1120                1125

Leu Met Ser Val Asn Val Ile Gly Gln Arg Met Asp Phe Tyr Ala
        1130                1135                1140

Met Ile His Ala Cys Trp Leu Ile Ala Val Leu Tyr Arg Arg Arg
        1145                1150                1155

Arg Lys Ala Ile Ala Glu Ile Trp Pro Lys Tyr Cys Cys Phe Leu
        1160                1165                1170

Ala Cys Ile Ile Thr Phe Gln Tyr Phe Ile Cys Ile Gly Ile Pro
        1175                1180                1185

Pro Ala Pro Cys Arg Asp Tyr Pro Trp Arg Phe Lys Gly Ala Ser
        1190                1195                1200

Phe Asn Asp Asn Ile Ile Lys Trp Leu Tyr Phe Pro Asp Phe Ile
        1205                1210                1215

Val Arg Pro Asn Pro Val Phe Leu Val Tyr Asp Phe Met Leu Leu
        1220                1225                1230

Leu Cys Ala Ser Leu Gln Arg Gln Ile Phe Glu Asp Glu Asn Lys
        1235                1240                1245

Ala Ala Val Arg Ile Met Ala Gly Asp Asn Val Glu Ile Cys Met
        1250                1255                1260

Asn Leu Asp Ala Ala Ser Phe Ser Gln His Asn Pro Val Pro Asp
        1265                1270                1275

Phe Ile His Cys Arg Ser Tyr Leu Asp Met Ser Lys Val Ile Ile
        1280                1285                1290
```

-continued

Phe Ser Tyr Leu Phe Trp Phe Val Leu Thr Ile Ile Phe Ile Thr
1295                 1300                1305

Gly Thr Thr Arg Ile Ser Ile Phe Cys Met Gly Tyr Leu Val Ala
1310                 1315                1320

Cys Phe Tyr Phe Leu Leu Phe Gly Gly Asp Leu Leu Leu Lys Pro
1325                 1330                1335

Ile Lys Ser Ile Leu Arg Tyr Trp Asp Trp Leu Ile Ala Tyr Asn
1340                 1345                1350

Val Phe Val Ile Thr Met Lys Asn Ile Leu Ser Ile Gly Ala Cys
1355                 1360                1365

Gly Tyr Ile Gly Thr Leu Val His Asn Ser Cys Trp Leu Ile Gln
1370                 1375                1380

Ala Phe Ser Leu Ala Cys Thr Val Lys Gly Tyr Gln Met Pro Ala
1385                 1390                1395

Ala Asn Ser Pro Cys Thr Leu Pro Ser Gly Glu Ala Gly Ile Ile
1400                 1405                1410

Trp Asp Ser Ile Cys Phe Ala Phe Leu Leu Leu Gln Arg Arg Val
1415                 1420                1425

Phe Met Ser Tyr Tyr Phe Leu His Val Val Ala Asp Ile Lys Ala
1430                 1435                1440

Ser Gln Ile Leu Ala Ser Arg Gly Ala Glu Leu Phe Gln Ala Thr
1445                 1450                1455

Ile Val Lys Ala Val Lys Ala Arg Ile Glu Glu Lys Lys Ser
1460                 1465                1470

Met Asp Gln Leu Lys Arg Gln Met Asp Arg Ile Lys Ala Arg Gln
1475                 1480                1485

Gln Lys Tyr Lys Lys Gly Lys Glu Arg Met Leu Ser Leu Thr Gln
1490                 1495                1500

Glu Pro Gly Glu Gly Gln Asp Met Gln Lys Leu Ser Glu Glu Asp
1505                 1510                1515

Asp Glu Arg Glu Ala Asp Lys Gln Lys Ala Lys Gly Lys Lys Lys
1520                 1525                1530

Gln Trp Trp Arg Pro Trp Val Asp His Ala Ser Met Val Arg Ser
1535                 1540                1545

Gly Asp Tyr Tyr Leu Phe Glu Thr Asp Ser Glu Glu Glu Glu Glu
1550                 1555                1560

Glu Glu Leu Lys Lys Glu Asp Glu Glu Pro Pro Arg Arg Ser Ala
1565                 1570                1575

Phe Gln Phe Val Tyr Gln Ala Trp Ile Thr Asp Pro Lys Thr Ala
1580                 1585                1590

Leu Arg Gln Arg His Lys Glu Lys Lys Arg Ser Ala Arg Glu Glu
1595                 1600                1605

Arg Lys Arg Arg Arg Lys Gly Ser Lys Glu Gly Pro Val Glu Trp
1610                 1615                1620

Glu Asp Arg Glu Asp Glu Pro Ile Lys Lys Lys Ser Asp Gly Pro
1625                 1630                1635

Asp Asn Ile Ile Lys Arg Ile Phe Asn Ile Leu Lys Phe Thr Trp
1640                 1645                1650

Val Leu Phe Leu Ala Thr Val Asp Ser Phe Thr Thr Trp Leu Asn
1655                 1660                1665

Ser Ile Ser Arg Glu His Ile Asp Ile Ser Thr Val Leu Arg Ile
1670                 1675                1680

```
Glu Arg Cys Met Leu Thr Arg Glu Ile Lys Lys Gly Asn Val Pro
    1685                1690                1695

Thr Arg Glu Ser Ile His Met Tyr Tyr Gln Asn His Ile Met Asn
    1700                1705                1710

Leu Ser Arg Glu Ser Gly Leu Asp Thr Ile Asp Glu His Pro Gly
    1715                1720                1725

Ala Ala Ser Gly Ala Gln Thr Ala His Arg Met Asp Ser Leu Asp
    1730                1735                1740

Ser His Asp Ser Ile Ser Ser Glu Pro Thr Gln Cys Thr Met Leu
    1745                1750                1755

Tyr Ser Arg Gln Gly Thr Thr Glu Thr Ile Glu Glu Val Glu Ala
    1760                1765                1770

Glu Gln Glu Glu Glu Ala Gly Ser Thr Ala Pro Glu Pro Arg Glu
    1775                1780                1785

Ala Lys Glu Tyr Glu Ala Thr Gly Tyr Asp Val Gly Ala Met Gly
    1790                1795                1800

Ala Glu Glu Ala Ser Leu Thr Pro Glu Glu Glu Leu Thr Gln Phe
    1805                1810                1815

Ser Thr Leu Asp Gly Asp Val Glu Ala Pro Pro Ser Tyr Ser Lys
    1820                1825                1830

Ala Val Ser Phe Glu His Leu Ser Phe Gly Ser Gln Asp Asp Ser
    1835                1840                1845

Ala Gly Lys Asn Arg Met Ala Val Ser Pro Asp Asp Ser Arg Thr
    1850                1855                1860

Asp Lys Leu Gly Ser Ser Ile Leu Pro Pro Leu Thr His Glu Leu
    1865                1870                1875

Thr Ala Ser Glu Leu Leu Leu Lys Lys Met Phe His Asp Asp Glu
    1880                1885                1890

Leu Glu Glu Ser Glu Lys Phe Tyr Val Gly Gln Pro Arg Phe Leu
    1895                1900                1905

Leu Leu Phe Tyr Ala Met Tyr Asn Thr Leu Val Ala Arg Ser Glu
    1910                1915                1920

Met Val Cys Tyr Phe Val Ile Ile Leu Asn His Met Val Ser Ala
    1925                1930                1935

Ser Met Ile Thr Leu Leu Leu Pro Ile Leu Ile Phe Leu Trp Ala
    1940                1945                1950

Met Leu Ser Val Pro Arg Pro Ser Arg Arg Phe Trp Met Met Ala
    1955                1960                1965

Ile Val Tyr Thr Glu Val Ala Ile Val Val Lys Tyr Phe Phe Gln
    1970                1975                1980

Phe Gly Phe Phe Pro Trp Asn Lys Asn Val Glu Val Asn Lys Asp
    1985                1990                1995

Lys Pro Tyr His Pro Pro Asn Ile Ile Gly Val Glu Lys Lys Glu
    2000                2005                2010

Gly Tyr Val Leu Tyr Asp Leu Ile Gln Leu Leu Ala Leu Phe Phe
    2015                2020                2025

His Arg Ser Ile Leu Lys Cys His Gly Leu Trp Asp Glu Asp Asp
    2030                2035                2040

Met Thr Glu Ser Gly Met Ala Arg Glu Glu Ser Asp Asp Glu Leu
    2045                2050                2055

Ser Leu Gly His Gly Arg Arg Asp Ser Ser Asp Ser Leu Lys Ser
    2060                2065                2070
```

```
Ile Asn Leu Ala Ala Ser Val Glu Ser Val His Val Thr Phe Pro
2075                2080                2085

Glu Gln Gln Thr Ala Val Arg Arg Lys Arg Ser Gly Ser Ser Ser
2090                2095                2100

Glu Pro Ser Gln Arg Ser Ser Phe Ser Ser Asn Arg Ser Gln Arg
2105                2110                2115

Gly Ser Thr Ser Thr Arg Asn Ser Ser Gln Lys Gly Ser Ser Val
2120                2125                2130

Leu Ser Ile Lys Gln Lys Gly Lys Arg Glu Leu Tyr Met Glu Lys
2135                2140                2145

Leu Gln Glu His Leu Ile Lys Ala Lys Ala Phe Thr Ile Lys Lys
2150                2155                2160

Thr Leu Glu Ile Tyr Val Pro Ile Lys Gln Phe Phe Tyr Asn Leu
2165                2170                2175

Ile His Pro Glu Tyr Ser Ala Val Thr Asp Tyr Val Leu Met
2180                2185                2190

Phe Leu Ala Asp Thr Val Asp Phe Ile Ile Val Phe Gly Phe
2195                2200                2205

Trp Ala Phe Gly Lys His Ser Ala Ala Ala Asp Ile Thr Ser Ser
2210                2215                2220

Leu Ser Glu Asp Gln Val Pro Gly Pro Phe Leu Val Met Val Leu
2225                2230                2235

Ile Gln Phe Gly Thr Met Val Val Asp Arg Ala Leu Tyr Leu Arg
2240                2245                2250

Lys Thr Val Leu Gly Lys Val Ile Phe Gln Val Ile Leu Val Phe
2255                2260                2265

Gly Ile His Phe Trp Met Phe Phe Ile Leu Pro Gly Val Thr Glu
2270                2275                2280

Arg Lys Phe Ser Gln Asn Leu Val Ala Gln Leu Trp Tyr Phe Val
2285                2290                2295

Lys Cys Val Tyr Phe Gly Leu Ser Ala Tyr Gln Ile Arg Cys Gly
2300                2305                2310

Tyr Pro Thr Arg Val Leu Gly Asn Phe Leu Thr Lys Ser Tyr Asn
2315                2320                2325

Tyr Val Asn Leu Phe Leu Phe Gln Gly Phe Arg Leu Val Pro Phe
2330                2335                2340

Leu Thr Glu Leu Arg Ala Val Met Asp Trp Val Trp Thr Asp Thr
2345                2350                2355

Thr Leu Ser Leu Ser Ser Trp Ile Cys Val Glu Asp Ile Tyr Ala
2360                2365                2370

His Ile Phe Ile Leu Lys Cys Trp Arg Glu Ser Glu Lys Arg Tyr
2375                2380                2385

Pro Gln Pro Arg Gly Gln Lys Lys Lys Lys Val Val Lys Tyr Gly
2390                2395                2400

Met Gly Gly Met Ile Ile Val Leu Leu Ile Cys Ile Val Trp Phe
2405                2410                2415

Pro Leu Leu Phe Met Ser Leu Ile Lys Ser Val Ala Gly Val Ile
2420                2425                2430

Asn Gln Pro Leu Asp Val Ser Val Thr Ile Thr Leu Gly Gly Tyr
2435                2440                2445

Gln Pro Ile Phe Thr Met Ser Ala Gln Gln Ser Gln Leu Lys Val
2450                2455                2460
```

-continued

```
Met Asp Gln Gln Ser Phe Asn Lys Phe Ile Gln Ala Phe Ser Arg
    2465            2470            2475
Asp Thr Gly Ala Met Gln Phe Leu Glu Asn Tyr Glu Lys Glu Asp
    2480            2485            2490
Ile Thr Val Ala Glu Leu Glu Gly Asn Ser Asn Ser Leu Trp Thr
    2495            2500            2505
Ile Ser Pro Pro Ser Lys Gln Lys Met Ile His Glu Leu Leu Asp
    2510            2515            2520
Pro Asn Ser Ser Phe Ser Val Val Phe Ser Trp Ser Ile Gln Arg
    2525            2530            2535
Asn Leu Ser Leu Gly Ala Lys Ser Glu Ile Ala Thr Asp Lys Leu
    2540            2545            2550
Ser Phe Pro Leu Lys Asn Ile Thr Arg Lys Asn Ile Ala Lys Met
    2555            2560            2565
Ile Ala Gly Asn Ser Thr Glu Ser Ser Lys Thr Pro Val Thr Ile
    2570            2575            2580
Glu Lys Ile Tyr Pro Tyr Val Lys Ala Pro Ser Asp Ser Asn
    2585            2590            2595
Ser Lys Pro Ile Lys Gln Leu Leu Ser Glu Asn Asn Phe Met Asp
    2600            2605            2610
Ile Thr Ile Ile Leu Ser Arg Asp Asn Thr Thr Lys Tyr Asn Ser
    2615            2620            2625
Glu Trp Trp Val Leu Asn Leu Thr Gly Asn Arg Ile Tyr Asn Pro
    2630            2635            2640
Asn Ser Gln Ala Leu Glu Leu Val Val Phe Asn Asp Lys Val Ser
    2645            2650            2655
Pro Pro Ser Leu Gly Phe Leu Ala Gly Tyr Gly Ile Met Gly Leu
    2660            2665            2670
Tyr Ala Ser Val Val Leu Val Ile Gly Lys Phe Val Arg Glu Phe
    2675            2680            2685
Phe Ser Gly Ile Ser His Ser Ile Met Phe Glu Glu Leu Pro Asn
    2690            2695            2700
Val Asp Arg Ile Leu Lys Leu Cys Thr Asp Ile Phe Leu Val Arg
    2705            2710            2715
Glu Thr Gly Glu Leu Glu Leu Glu Glu Asp Leu Tyr Ala Lys Leu
    2720            2725            2730
Ile Phe Leu Tyr Arg Ser Pro Glu Thr Met Ile Lys Trp Thr Arg
    2735            2740            2745
Glu Lys Thr Asn
    2750
```

METHODS AND COMPOSITIONS FOR FLUID DRAINAGE BY PIEZO ION CHANNEL ACTIVATION

CROSS-REFERENCE TO RELATED APPLICATIONS

This application claims the benefit of U.S. provisional application Ser. No. 62/774,197 filed Jan. 12, 2020, the disclosure of which is hereby incorporated in its entirety by reference herein.

STATEMENT REGARDING FEDERALLY SPONSORED RESEARCH OR DEVELOPMENT

The invention was made with Government support under Contract Nos. EY026260, HL121036, HL141857, DE027891, and DK114645awarded by the National Institutes of Health. The Government has certain rights to the invention.

SEQUENCE LISTING

The text file Sequence listing Piezo_sequence_ST25.txt of size 65.8 KB created Jan. 11, 2021, filed herewith, is hereby incorporated by reference.

TECHNICAL FIELD

The disclosure generally relates to methods and compositions for treating various ailments or conditions through activating or expressing Piezo ion channels.

BACKGROUND

Piezo proteins, encoded by Piezo1 and Piezo2, were originally identified as pore-forming subunits of a mechanically activated ion channel. Piezo1 has subsequently been demonstrated to be a cell stretch sensor that integrates physiological force into vascular architecture, functioning as a critical molecular player for vascular development and function. Two pioneering patient-based studies have recently associated mutations in Piezo1 gene with generalized lymphatic dysplasia and dysfunction. Despite these strong clinical associations, it remains unknown how Piezo1 plays a role in mechanotransduction that controls lymphatic development, maintenance, and function.

SUMMARY

The disclosure generally relates to methods and compositions for treating various ailments or conditions through activating or expressing Piezo ion channels.

In various embodiments are disclosed methods of treating impaired lymphatic function in a subject including the step of inducing activation of Piezo1 ion channels in lymphatic tissues of a subject having impaired lymphatic function. In various embodiments are disclosed compositions for treating impaired lymphatic function in a subject.

In various embodiments are disclosed methods of treating ocular hypertension or glaucoma in a subject including the step of inducing activation of Piezo1 ion channels in an eye of a subject having an ocular pressure that is greater than 22 mm Hg. In various embodiments are disclosed compositions for treating ocular hypertension or glaucoma in a subject.

In various embodiments are disclosed methods of treating brain injury in a subject including the step of inducing activation of Piezo1 ion channels in a brain of a subject, where the brain is injured or damaged. In various embodiments are disclosed compositions for treating brain injury in a subject.

In various embodiments are disclosed methods of treating lymphedema in a subject or a disorder caused by lymphedema including the step of inducing in a subject activation of Piezo1 ion channels at a site of lymphedema, wherein the activation reduces a symptom of the lymphedema. In various embodiments are disclosed compositions for treating lymphedema in a subject or a disorder caused by lymphedema.

In a first aspect, a method of treating impaired lymphatic function in a subject is provided. The method includes a step of inducing activation of Piezo1 ion channels in lymphatic tissues of a subject having impaired lymphatic function.

In a refinement of the first aspect, the inducing step includes administering a pharmaceutical composition comprising an amount of a Piezo1 agonist effective for treating dysfunctional lymphatic valves in the lymphatic tissues.

In a further of the first aspect, the Piezo1 agonist includes a compound of formula (I)

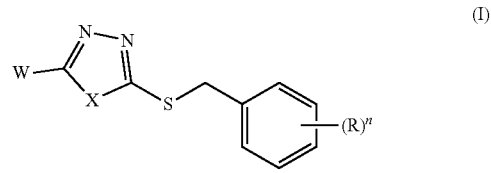

or a physiologically or pharmaceutically acceptable salt thereof, wherein:
n is 0, 1, or 2;
each R is chlorine;
X is S; and
W is aryl or heteroaryl.

In a further refinement, of the first aspect, the compound of formula (I) is 2-[(2,6-dichlorophenyl)methylsulfanyl]-5-pyrazin-2-yl-1,3,4-thiadiazole.

In a refinement of the first aspect, the inducing step includes applying oscillatory shear stress to the lymphatic tissues.

In a further refinement of the first aspect, the oscillatory shear stress does not activate Piezo2 ion channels in the lymphatic tissues.

In a further refinement of the first aspect, the applying step includes directing ultrasound pulses towards the lymphatic tissues.

In a further refinement of the first aspect, the ultrasound pulses have a frequency of 43 megahertz (MHz).

In a further refinement of the first aspect, the inducing step further includes administering a pharmaceutical composition comprising an amount of a Piezo1 agonist effective for treating dysfunctional lymphatic valves in the lymphatic tissues.

In a further refinement of the first aspect, the Piezo1 agonist includes a compound of formula (I)

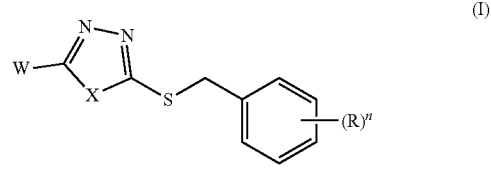

or a physiologically or pharmaceutically acceptable salt thereof, wherein:
n is 0, 1, or 2;
each R is chlorine;
X is S; and
W is aryl or heteroaryl.

In a further refinement of the first aspect, the compound of formula (I) is 2-[(2,6-dichlorophenyl)methylsulfanyl]-5-pyrazin-2-yl-1,3,4-thiadiazole.

In a second aspect, a method of treating ocular hypertension or glaucoma in a subject is provided. The method includes a step of inducing activation of Piezo1 ion channels in an eye of a subject having an ocular pressure that is greater than 22 mm Hg.

In a refinement of the second aspect, the inducing step includes administering a pharmaceutical composition comprising an amount of a Piezo1 agonist effective for reducing the ocular pressure.

In a further refinement of the second aspect, the Piezo1 agonist includes a compound of formula (I)

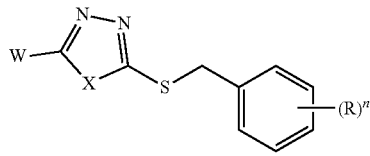

or a physiologically or pharmaceutically acceptable salt thereof, wherein:
n is 0, 1, or 2;
each R is chlorine;
X is S; and
W is aryl or heteroaryl.

In a further refinement of the second aspect, the compound of formula (I) is 2-[(2,6-dichlorophenyl)methylsulfanyl]-5-pyrazin-2-yl-1,3,4-thiadiazole.

In a refinement of the second aspect, the inducing step includes applying oscillatory shear stress to the eye.

In a further refinement of the second aspect, the oscillatory shear stress does not activate Piezo2 ion channels in the eye.

In a further refinement of the second aspect, the applying step includes directing ultrasound pulses towards the eye.

In a further refinement of the second aspect, the ultrasound pulses have a frequency of 43 megahertz (MHz).

In a further refinement of the second aspect, the inducing step further includes administering a pharmaceutical composition comprising an amount of a Piezo1 agonist effective for reducing the ocular pressure.

In a further refinement of the second aspect, the Piezo1 agonist includes a compound of formula (I)

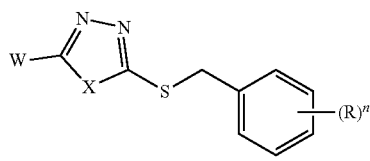

or a physiologically or pharmaceutically acceptable salt thereof, wherein:
n is 0, 1, or 2;
each R is chlorine;
X is S; and
W is aryl or heteroaryl.

In a further refinement of the second aspect, the compound of formula (I) is 2-[(2,6-dichlorophenyl)methylsulfanyl]-5-pyrazin-2-yl-1,3,4-thiadiazole.

In a third aspect, a method of treating brain injury in a subject is provided. The method includes a step of inducing activation of Piezo1 ion channels in a brain of a subject, where the brain is injured or damaged.

In a refinement of the third aspect, the inducing step includes administering a pharmaceutical composition comprising an amount of a Piezo1 agonist effective for remediating the injury of damage.

In a refinement of the third aspect, the Piezo1 agonist includes a compound of formula (I)

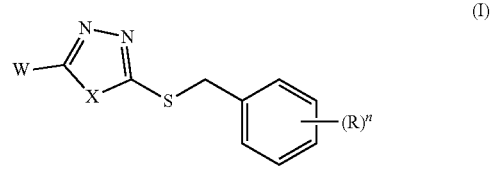

or a physiologically or pharmaceutically acceptable salt thereof, wherein:
n is 0, 1, or 2;
each R is chlorine;
X is S; and
W is aryl or heteroaryl.

In a further refinement of the third aspect, the compound of formula (I) is 2-[(2,6-dichlorophenyl)methylsulfanyl]-5-pyrazin-2-yl-1,3,4-thiadiazole.

In a refinement of the third aspect, the inducing step includes applying oscillatory shear stress to a site of the brain that is injured or damaged.

In a further refinement of the third aspect, oscillatory shear stress does not activate Piezo2 ion channels in the brain.

In a further refinement of the third aspect, the applying step includes directing ultrasound pulses towards the site.

In a further refinement of the third aspect, the ultrasound pulses have a frequency of 43 megahertz (MHz).

In a further refinement of the third aspect, the inducing step further includes administering a pharmaceutical composition comprising an amount of a Piezo1 agonist effective for remediating the injury of damage.

In a further refinement of the third aspect, the Piezo1 agonist includes a compound of formula (I)

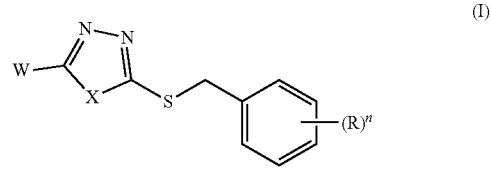

or a physiologically or pharmaceutically acceptable salt thereof, wherein:
n is 0, 1, or 2;
each R is chlorine;
X is S; and
W is aryl or heteroaryl.

In a fourth aspect, a method of treating lymphedema in a subject or a disorder caused by lymphedema is provided. The method comprising includes a step of inducing in a subject activation of Piezo1 ion channels at a site of lymphedema, wherein the activation reduces a symptom of the lymphedema.

In a further refinement of the third aspect, the compound of formula (I) is 2-[(2,6-dichlorophenyl)methylsulfanyl]-5-pyrazin-2-yl-1,3,4-thiadiazole.

In a refinement of the fourth aspect, the symptom is swelling at the site.

In a refinement of the fourth aspect, the inducing step includes administering a pharmaceutical composition comprising an amount of a Piezo1 agonist effective for reducing the symptom of the lymphedema.

In a refinement of the fourth aspect, the Piezo1 agonist includes a compound of formula (I)

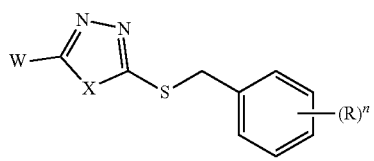

(I)

or a physiologically or pharmaceutically acceptable salt thereof, wherein:
n is 0, 1, or 2;
each R is chlorine;
X is S; and
W is aryl or heteroaryl.

In a further refinement of the fourth aspect, the compound of formula (I) is 2-[(2,6-dichlorophenyl)methylsulfanyl]-5-pyrazin-2-yl-1,3,4-thiadiazole.

In a further refinement of the fourth aspect, the inducing step includes applying oscillatory shear stress to the site.

In a further refinement of the fourth aspect, the oscillatory shear stress does not activate Piezo2 ion channels at the site.

In a further refinement of the fourth aspect, the applying step includes directing ultrasound pulses towards the site.

In a further refinement of the fourth aspect, the ultrasound pulses have a frequency of 43 megahertz (MHz).

In a further refinement of the fourth aspect, the inducing step further includes administering a pharmaceutical composition comprising an amount of a Piezo1 agonist effective for reducing the symptom of the lymphedema.

In a further refinement of the fourth aspect, the Piezo1 agonist includes a compound of formula (I)

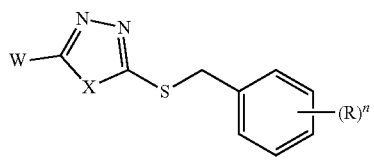

(I)

or a physiologically or pharmaceutically acceptable salt thereof, wherein:
n is 0, 1, or 2;
each R is chlorine;
X is S; and
W is aryl or heteroaryl.

In a further refinement of the fourth aspect, the compound of formula (I) is 2-[(2,6-dichlorophenyl)methylsulfanyl]-5-pyrazin-2-yl-1,3,4-thiadiazole.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 1A shows an experimental scheme of various embodiments.

FIGS. 1B, 1C, 1D, 1E, 1F, and 1G show visualizations of tdTomato signals in the mesenteric lymphatics of Piezo1 knockout (KO) mouse pups having Prox1 promoter-driven tdTomato signals.

FIG. 2A shows an experimental scheme of various embodiments.

FIGS. 2B, 2C, 2D, 2E, 2F, and 2G show images of collecting lymphatic vessels closely running next to the saphenous vein in the hind limb of control and lymphatic or Piezo1 KO mice.

FIG. 3A are Western immunoblot assays showing protein expression of FOXC2 and GATA2 from primary human lymphoid endothelial cells (LECs) subjected to oscillatory shear stress (OSS).

FIG. 3B is a graph showing mRNA levels of Cx37, LAMA5 and ITGA9 from LECs subjected to OSS.

FIG. 3C are Western immunoblot assays showing regulation of lymphatic valve-associated genes by Piezo1.

FIG. 3D shows images from immunofluorescence assays against genes of interest (FOXC2, GATA2, Cx37, LAMA5, and ITGA9).

FIG. 3E is graph of a qRT-PCR analysis showing the expression of the lymphatic valve-associated genes in LECs that were transfected with a control (CTR) or Piezo1/EGFP-expressing plasmid (Piezo1) for 24 hours.

FIG. 3F is a Western immunoblot assay showing the expression of the lymphatic valve-associated genes in LECs that were transfected with a control (CTR) or Piezo1/EGFP-expressing plasmid (Piezo1) for 48 hours.

FIG. 4A are Western immunoblot assays showing expression of lymphatic valve genes in primary LECs that were subjected to static culturing or cyclic cell stretching for 4, 8, and 24 hours.

DETAILED DESCRIPTION

Figure 1H:
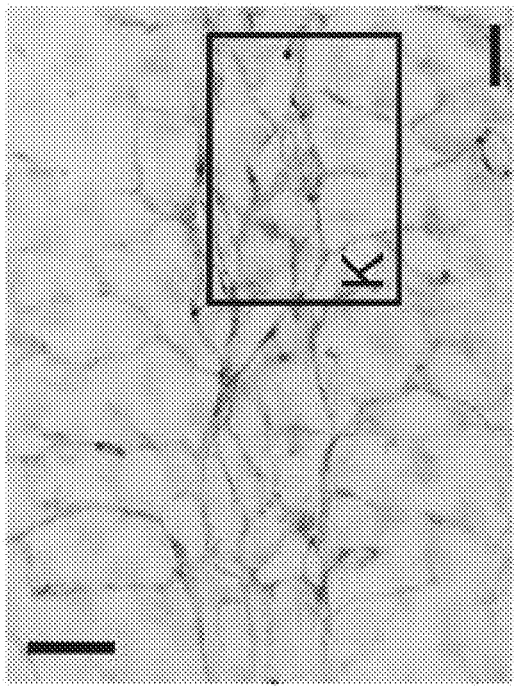
FIGS. 1H, 1I, 1J, and 1K show images of impaired dermal lymphatic valve development in the tail skin of lymphatic Piezo1 KO mouse pups.
Figure 1I:
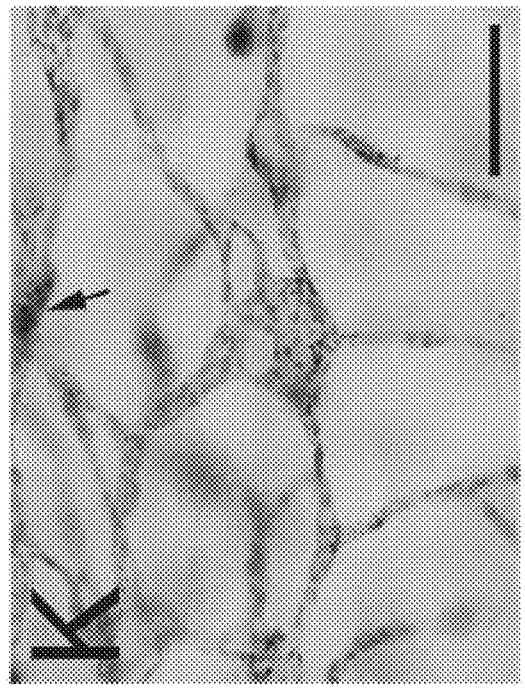
Figure 1J:
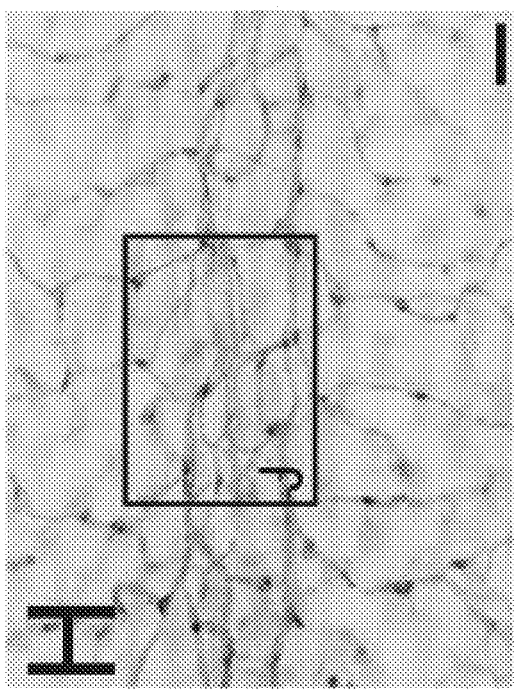
Figure 1K:
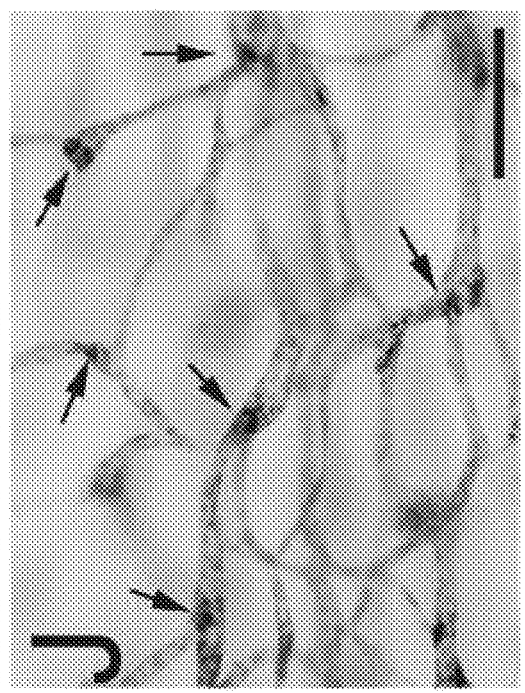

As required, detailed embodiments of the present disclosure are disclosed herein; however, it is to be understood that the disclosed embodiments are merely exemplary and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art.

Except in the examples, or where otherwise expressly indicated, all numerical quantities in this description indicating amounts of material or conditions of reaction and/or use are to be understood as modified by the word "about". The first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

Unless indicated otherwise, all technical and scientific terms used herein have the same meaning as commonly understood by one of ordinary skill in the art to which the present disclosure belongs.

It is also to be understood that this disclosure is not limited to the specific embodiments and methods described below, as specific components and/or conditions may, of course, vary. Furthermore, the terminology used herein is used only for describing particular embodiments and is not intended to be limiting in any way.

It is also noted that, as used in the specification and the appended claims, the singular form "a," "an," and "the" comprise plural referents unless the context clearly indicates otherwise. For example, reference to a component in the singular is intended to comprise a plurality of components.

The term "or" can be understood to mean "at least one of". The term "and" can also be understood to mean "at least one of" or "all".

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

The term "effective amount" of drug, compound, or pharmaceutical composition is an amount sufficient to effect beneficial or desired results.

The term "treating" refers to decreasing in one or more symptoms characteristic of a disease or disorder; a decrease in the rate of progression of the disease or disorder; recovery from the disease or disorder, cure from the disease or disorder, maintenance of remission and prophylaxis such as prevention of relapse.

The term "subject(s)" refers to subjects of any mammalian subject(s) of any mammalian species such as, but not limited to, humans, dogs, cats, horses, rodents, any domesticated animal, or any wild animal.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer) include hydrogen, alkyl, lower alkyl, $C_{1-6}$ alkyl, $C_{6-10}$ aryl, $C_{6-10}$ heteroaryl, alylaryl (e.g., $C_{1-8}$ alkyl $C_{6-10}$ aryl), —$NO_2$, —$NH_2$, —N(R'R"), —N(R'R"R''')$^+$L$^-$, Cl, F, Br, —$CF_3$, —$CCl_3$, —CN, —$SO_3$H, —$PO_3H_2$, —COOH, —$CO_2$R', —COR', —CHO, —OH, —OR', —O$^-$M$^+$, —$SO_3^-$M$^+$, —$PO_3^-$M$^+$, —COO$^-$M$^+$, —$CF_2$H, —$CF_2$R', —$CFH_2$, and —CFR'R" where R', R" and R''' are $C_{1-10}$ alkyl or $C_{6-8}$ aryl groups, M$^+$ is a metal ion, and L$^-$ is a negatively charged counter ion; R groups on adjacent carbon atoms can be combined as —$OCH_2O$—; single letters (e.g., "n" or "o") are 1, 2, 3, 4, or 5; in the compounds disclosed herein a CH bond can be substituted with alkyl, lower alkyl, $C_{1-6}$ alkyl, $C_{6-10}$ aryl, $C_{6-10}$ heteroaryl, —$NO_2$, —$NH_2$, —N(R'R"), —N(R'R"R''')$^+$L$^+$, Cl, F, Br, —$CF_3$, —$CCl_3$, —CN, —$SO_3$H, —$PO_3H_2$, —COOH, —$CO_2$R', —COR', —CHO, —OH, —OR', —O$^-$M$^+$, —$SO_3$M$^+$, —$PO_3$-M$^+$, —COO$^-$M$^+$, —$CF_2$H, —$CF_2$R', —$CFH_2$, and —CFR'R" where R', R" and R''' are $C_{1-10}$ alkyl or $C_{6-18}$ aryl groups, M$^+$ is a metal ion, and L$^-$ is a negatively charged counter ion; hydrogen atoms on adjacent carbon atoms can be substituted as —$OCH_2O$—; when a given chemical structure includes a substituent on a chemical moiety (e.g., on an aryl, alkyl, etc.) that substituent is imputed to a more general chemical structure encompassing the given structure; percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

As used herein, the term "about" means that the amount or value in question may be the specific value designated or some other value in its neighborhood. Generally, the term "about" denoting a certain value is intended to denote a range within +/−5% of the value. As one example, the phrase "about 100" denotes a range of 100+/−5, i.e. the range from 95 to 105. Generally, when the term "about" is used, it can be expected that similar results or effects according to the invention can be obtained within a range of +/−5% of the indicated value.

As used herein, the term "and/or" means that either all or only one of the elements of said group may be present. For example, "A and/or B" shall mean "only A, or only B, or both A and B". In the case of "only A", the term also covers the possibility that B is absent, i.e. "only A, but not B".

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

The term "alkyl" as used herein means $C_{1-20}$, linear, branched, rings, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. Lower alkyl can also refer to a range between any two numbers of carbon atoms listed above. "Higher alkyl" refers to an alkyl group having about 10 to about 20 carbon atoms, e.g., 10, 11, 12, 13, 14, 15, 16, 17, 18, 19, or 20 carbon atoms. Higher alkyl can also refer to a range between any two number of carbon atoms listed above.

The term "aryl" as used herein means an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Examples of aryl include, but are not limited to, phenyl, naphthyl, biphenyl, and diphenylether, and the like. Aryl groups include heteroaryl groups, wherein the aromatic ring or rings include a heteroatom (e.g., N, O, S, or Se). Exemplary heteroaryl groups include, but are not limited to, furanyl, pyridyl, pyrimidinyl, imidazoyl, benzimidazolyl, benzofuranyl, benzothiophenyl, quinolinyl, isoquinolinyl, thiophenyl, and the like. The aryl group can be optionally substituted (a "substituted aryl") with one or more aryl group substituents, which can be the same or different, wherein "aryl group substituent" includes alkyl (saturated or unsaturated), substituted alkyl (e.g., haloalkyl and perhaloalkyl, such as but not limited to $-CF_3$), cycloalkyl, aryl, substituted aryl, aralkyl, halo, nitro, hydroxyl, acyl, carboxyl, alkoxyl (e.g., methoxy), aryloxyl, aralkyloxyl, thioalkyl, thioaryl, thioaralkyl, amino (e.g., aminoalkyl, aminodialkyl, aminoaryl, etc.), sulfonyl, and sulfinyl.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within +0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

For all compounds expressed as an empirical chemical formula with a plurality of letters and numeric subscripts (e.g., $CH_2O$), values of the subscripts can be plus or minus 50 percent of the values indicated rounded to or truncated to two significant figures. For example, if $CH_2O$ is indicated, a compound of formula $C_{(0.8-1.2)}H_{(1.6-2.4)}O_{(0.8-1.2)}$. In a refinement, values of the subscripts can be plus or minus 30 percent of the values indicated rounded to or truncated to two significant figures. In still another refinement, values of the subscripts can be plus or minus 20 percent of the values indicated rounded to or truncated to two significant figures.

The terms "polynucleotide", "nucleotide", "nucleotide sequence", "nucleic acid" and "oligonucleotide" are used interchangeably in this disclosure. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "heterologous" nucleic acid can refer to a nucleic acid that is not normally or naturally found in or produced by a given bacterium, organism, or cell in nature. The term "homologous" nucleic acid can refer to a nucleic acid that is normally found in or produced by a given bacterium, organism, or cell in nature.

The term "recombinant" is understood to mean that a particular nucleic acid (DNA or RNA) or protein is the product of various combinations of cloning, restriction, or ligation steps resulting in a construct having a structural coding or non-coding sequence distinguishable from endogenous nucleic acids found in natural systems.

The terms "amino acid sequence" or "amino acid" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine.

The terms "peptide" or "protein" as used herein refers to any peptide, oligopeptide, polypeptide, gene product, expression product, or protein. A peptide is comprised of consecutive amino acids. The term "peptide" encompasses naturally occurring or synthetic molecules.

The terms "construct", "cassette", "expression cassette", "plasmid", "vector", or "expression vector" is understood to mean a recombinant nucleic acid, generally recombinant DNA, which has been generated for the purpose of the expression or propagation of a nucleotide sequence(s) of interest, or is to be used in the construction of other recombinant nucleotide sequences.

The term "promoter" or "promoter polynucleotide" is understood to mean a regulatory sequence/element or control sequence/element that is capable of binding/recruiting a RNA polymerase and initiating transcription of sequence downstream or in a 3' direction from the promoter. A promoter can be, for example, constitutively active or always on or inducible in which the promoter is active or inactive in the presence of an external stimulus. Example of promoters include cytomegalovirus (CMV) or elongation factor 1a (EF1a) promoters.

The term "operably linked" can mean the positioning of components in a relationship which permits them to function in their intended manner. For example, a promoter can be linked to a polynucleotide sequence to induce transcription of the polynucleotide sequence.

The terms "sequence identity" or "identity" refers to a specified percentage of residues in two nucleic acid or amino acid sequences that are identical when aligned for maximum correspondence over a specified comparison window, as measured by sequence comparison algorithms or by visual inspection, wherein the portion of the sequence in the comparison window may include additions or deletions (i.e., gaps) as compared to the reference sequence (which does not comprise additions or deletions) for optimal alignment of the two sequences. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity.

The term "comparison window" refers to a segment of at least about 20 contiguous positions in which a sequence may be compared to a reference sequence of the same number of contiguous positions after the two sequences are aligned optimally. In a refinement, the comparison window is from 15 to 30 contiguous positions in which a sequence may be compared to a reference sequence of the same number of contiguous positions after the two sequences are aligned optimally. In another refinement, the comparison window is usually from about 50 to about 200 contiguous positions in which a sequence may be compared to a reference sequence of the same number of contiguous positions after the two sequences are aligned optimally.

The terms "complementarity" or "complement" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 4, 5, and 6 out of 6 being 66.67%, 83.33%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 80%, 85%, 90%, 95%, 97%, 98%, 99%, or 100%, or percentages in between over a region of 4, 5, 6, 7, 8, 9, 10, 15, or 20 nucleotides, or refers to two nucleic acids that hybridize under stringent conditions.

The term "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion (such as domain antibodies), and any other modified configuration of the immunoglobulin molecule that comprises an antigen recognition site. An antibody includes an antibody of any class, such as IgG, IgA, or IgM (or sub-class thereof), and the antibody need not be of any particular class.

The terms "siRNA oligonucleotides", "RNAi oligonucleotides", "short interfering RNA", or "siRNA" are used interchangeably and refer to oligonucleotides that work through post-transcriptional gene silencing, also known as RNA interference (RNAi). The terms refer to a double stranded nucleic acid molecule capable of RNA interference "RNAi", (PCT Publication No. WO 00/44895; WO 01/36646; WO 99/32619; WO 01/29058 that are all incorporated in their entirety by reference). SiRNA molecules are generally RNA molecules but further encompass chemically modified nucleotides and non-nucleotides. SiRNA gene-targeting experiments have been carried out by transient siRNA transfer into cells (achieved by such classic methods as liposome-mediated transfection, electroporation, or microinjection). Molecules of siRNA are 21- to 23-nucleotide RNAs, with characteristic 2- to 3-nucleotide 3'-overhanging ends resembling the RNase III processing products of long double-stranded RNAs (dsRNAs) that normally initiate RNAi. One method for efficient intracellular delivery of siRNA is the use of short hairpin RNAs, or "shRNAs". shRNAs are single stranded RNA molecules that include two complementary sequences joined by a non-complementary region. In vivo, the complementary sequences anneal to create a double-stranded helix with an unpaired loop at one end. The resulting lollypop-shaped shaped structure is called a stem loop and can be recognized by the RNAi machinery and processed intracellularly into short duplex RNAs having siRNA-like properties.

Other references that are all incorporated in its entirety by reference herein include the following patents, patent application publications, and publications: U.S. Pat. Nos. 6,894, 054, 7,514,566, 7,951,821, 8,084,479; U.S. Patent Application Publication No. 2003/0073726, 2008/0305520, 2013/0156762; PCT Application Publication No. WO 2002/

064135, WO 2005/070122, WO 2007/098252, WO 2012/027389; Prieto, Martin Loynaz, et al. "Activation of Piezo1 but Not NaV1. 2 Channels by Ultrasound at 43 M-Hz." *Ultrasound in medicine & biology* 44.6 (2018): 1217-1232; Syeda, Ruhma, et al. "Chemical activation of the mechanotransduction channel Piezo1." *Elife* 4 (2015): e07369; and Evans, Elizabeth L., et al. "Yoda1 analogue (Dooku1) which antagonizes Yoda1-evoked activation of Piezo1 and aortic relaxation." *British journal of pharmacology* 175 10 (2018): 1744-1759.

The disclosure generally relates to methods and compositions for treating various ailments or conditions through activating or expressing Piezo1 ion channels. For example, the treating of various ailments or conditions can include draining fluid through activating Piezo1 ion channels.

In various embodiments are disclosed methods of treating impaired lymphatic function in a subject including the step of inducing activation of Piezo1 ion channels in lymphatic tissues of a subject having impaired lymphatic function. In various embodiments are disclosed compositions for treating impaired lymphatic function in a subject.

In various embodiments are disclosed methods of treating ocular hypertension or glaucoma in a subject including the step of inducing activation of Piezo1 ion channels in an eye of a subject having an ocular pressure that is greater than 22 mm Hg. In various embodiments are disclosed compositions for treating ocular hypertension or glaucoma in a subject.

In various embodiments are disclosed methods of treating brain injury in a subject including the step of inducing activation of Piezo1 ion channels in a brain of a subject, where the brain is injured or damaged. In various embodiments are disclosed compositions for treating brain injury in a subject.

In various embodiments are disclosed methods of treating lymphedema in a subject or a disorder caused by lymphedema including the step of inducing in a subject activation of Piezo1 ion channels at a site of lymphedema, wherein the activation reduces a symptom of the lymphedema. In various embodiments are disclosed compositions for treating lymphedema in a subject or a disorder caused by lymphedema.

Activation of Piezo1 ion channels of various embodiments includes opening of the Piezo1 ion channels such that fluids or other matter can flow through the channel.

The inducing step of various embodiments further includes administering a pharmaceutical composition comprising an amount of a Piezo1 agonist. The amount of the Piezo1 agonist of various embodiments is effective for treating dysfunctional lymphatic valves in the lymphatic tissues, for reducing ocular pressure, remediating brain trauma or injury, or reducing a symptom of lymphedemia such as swelling or the lymphedema.

The Piezo1 agonist of various embodiments includes a compound of formula (I)

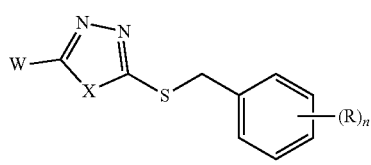

(I)

or a physiologically or pharmaceutically acceptable salt thereof, wherein:
n is 0, 1, or 2;
each R is chlorine; and
W is aryl or heteroaryl.

In various embodiments, the Piezo1 agonist includes 2-[(2,6-dichlorophenyl)methylsulfanyl]-5-pyrazin-2-yl-1,3,4-thiadiazole, Yoda1, or a compound of formula

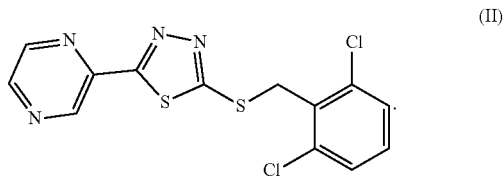 [SMILES: Clc1cccc(Cl)c1CSc1nnc(-c2cnccn2)s1]

(II)

The inducing step of various embodiments further includes applying oscillatory shear stress to a site for inducing activation of Piezo1 ion channels. The oscillatory shear stress can be effective for specifically activating Piezo1 ion channels. For example, oscillatory shear stress may specifically activate Piezo1 ion channels and not Piezo2 ion channels. The site of various embodiments includes sites on a subject such as lymph, lymph nodes lymphatic tissues, eyes, ocular regions, head, brain or regions of the brain such as where injuries are located, or sites where lymphedema can occur including appendages (legs, arms, fingers, or toes). The applying of oscillatory shear stress to a site of various embodiments can include directing ultrasound pulses to the site. In one refinement, the ultrasound pulses have a frequency of 43 megahertz (MHz).

In various embodiments, the inducing step includes administering a pharmaceutical composition comprising an amount of a Piezo1 agonist and applying oscillatory shear stress to a site for inducing activation of Piezo1 ion channels.

The methods of various embodiments can further include the step of increasing expression of Piezo1 ion channels. Examples of methods of increasing expression of Piezo1 ion channels can include administering a compound effective for stimulating expression of Piezo1 ion channels or using recombinant techniques using recombinant vectors with expression cassettes including polynucleotide encoding a Piezo1 ion channel operably linked to a promoter polynucleotide. For example, the polynucleotide has encoding a Piezo1 ion channel has at least 80%, 85%, 90%, 99%, or 100% sequence identity with SEQ ID NO: 1 which is a polynucleotide sequence encoding Piezo1 (*Homo Sapiens*) and the Piezo1 ion channel has at least 80%, 85%, 90%, 99%, or 100% sequence identity with SEQ ID NO: 2 which is an amino acid sequence for Piezo1 (*Homo Sapiens*).

The methods of various embodiments can further include the step inducing activation of Piezo2 ion channels. The step of inducing activation of Piezo2 ion channels can include administering a pharmaceutical composition comprising an amount of a Piezo2 agonist or applying oscillatory shear stress to a site for inducing activation of Piezo2 ion channels. Activation of Piezo2 ion channels of various embodiments includes opening of the Piezo2 ion channels such that fluids or other matter can flow through the channel. The activation of Piezo2 ion channels can, for example, drain fluid. The methods of various embodiments can further include the step of increasing expression of Piezo2 ion channels. Examples of methods of increasing expression of Piezo2 ion channels can include administering a compound effective for stimulating expression of Piezo2 ion channels or using recombinant techniques using recombinant vectors with expression cassettes including polynucleotide encoding a Piezo1 ion channel operably linked to a promoter polynucleotide. For example, the polynucleotide has encoding a Piezo2 ion channel has at least 80%, 85%, 90%, 99%, or 100% sequence identity with SEQ ID NO: 3 which is a polynucleotide sequence encoding Piezo2 (*Homo Sapiens*) and the Piezo1 ion channel has at least 80%, 85%, 90%, 99%, or 100% sequence identity with SEQ ID NO: 4 which is an amino acid sequence for Piezo2 (*Homo Sapiens*).

Alternatively, the methods of various embodiments can further include the step of inhibiting activation of Piezo2 ion channels or inhibiting flow through the Piezo2 ion channels. The inhibition can be carried out, for example, by expressing or administering an siRNA as disclosed in U.S. Patent Application Publication No. 2013/0156762 or administering an antagonist such as antibody specific to the Piezo2 ion channels. In one example, the D-GsMTx4 antibody as disclosed in Alcaino, Constanza, et al. "Mechanosensitive ion channel Piezo2 is inhibited by D-GsMTx4." *Channels* 11.3 (2017): 245-253, which is incorporated in its entirety by reference.

The following examples illustrate the various embodiments of the present disclosure. Those skilled in the art will recognize many variations that are within the spirit of the present disclosure and scope of the claims.

Example 1

PIEZO1 Incorporates Mechanical Force Signals to the Genetic Program that Governs Lymphatic Valve Development and Maintenance The lymphatic system plays crucial roles in tissue homeostasis, lipid absorption and immune cell trafficking. While lymphatic valves direct unidirectional lymph flows, the flow itself controls lymphatic valve formation. In this reciprocal crosstalk, a mechanotransduction senses the fluid-derived physical force, and incorporates the signal into the lymphatic valve-forming genetic program. Here, we demonstrate that the mechanically activated ion channel Piezo1 senses oscillating shear stress (OSS), and directs development and maintenance of lymphatic valves. Targeted deletion of Piezo1 in lymphatic vessels inhibited the initial formation and postnatal maintenance of the mesenteric and dermal lymphatic valves. Piezo1 knockdown in lymphatic endothelial cells (LECs) largely abrogated the OSS-induced upregulation of the lymphatic valve-signature genes. On the contrary, Piezo1 overexpression upregulates lymphatic valve genes in LECs in the absence of OSS. Strikingly, cyclic cell stretching of LECs could recapitulate the molecular phenotypes of lymphatic valves in a Piezo1-dependent manner. Moreover, chemical activation of Piezo1 in vivo led to an accelerated lymphatic valve formation.

The lymphatic system controls tissue fluid homeostasis, immune cell trafficking and lipid absorption. Lymphatic valves ensure a unidirectional flow of lymph fluid in lymphatic vessels. Dysfunctional or malformed lymphatic valves may significantly impair fluid drainage, immune cell trafficking, and lipid absorption (1-4). Fluid flow-generated mechanical force regulates various mechanotransduction pathways that incorporate the flow-induced shear stress signals into genetic programs that govern development and function of the vascular systems (5, 6). Together, our study identified the major role of Piezo1 as the force sensor in lymphatic valve formation and maintenance, providing a significant therapeutic implication of activating Piezo1 in treatment of congenital and surgery-associated lymphedema.

Previous studies have dissected mechanotransduction pathways that control different aspects of vascular pathophysiology (7-12). In particular, recent work has elegantly identified and characterized important molecular constituents in lymphatic valve formation. Notably, these molecular players, which are intricately controlled by fluid flow-generated oscillatory shear stress (OSS), cooperate with one another to orchestrate the genetic and epigenetic programs responsible for lymphatic valve formation, function and maintenance (13-20).

Piezo proteins, encoded by Piezo1 and Piezo2, were originally identified as pore-forming subunits of a mechanically activated ion channel (21, 22). Piezo1 has subsequently been demonstrated to be a cell stretch sensor that integrates physiological force into vascular architecture, functioning as a critical molecular player for vascular development and function (21-25). Two pioneering patient-based studies have recently associated mutations in Piezo1 gene with generalized lymphatic dysplasia and dysfunction (26, 27). Despite these strong clinical associations, it remains unknown how Piezo1 plays a role in mechanotransduction that controls lymphatic development, maintenance and function. In this paper, we aimed to elucidate the function of Piezo1 in embryonic and postnatal lymphatic growth and valve development.

Based on the data presented here, we propose that Piezo1 functions as a mechanotransduction sensor that senses cellular stretch caused by oscillating fluid flow, and subsequently regulates lymphatic valve formation and maintenance.

Methods

Animal-Related Works

All mouse works have been approved by the Institutional Animal Care and Use Committee, University of Southern California (PI: YK Hong). Sources of the mice are: Prox1-EGFP (Tg(Prox1-EGFP)KY221Gsat, Mutant Mouse Resource and Research Centers) (35), Prox1-tdTomato (Tg(Prox1-tdTomato)TA76Gsat/Mmucd, Mutant Mouse Resource and Research Centers) (28), Prox1-CreER$^{T2}$ (a kind gift from Dr. Taija Makinen, Uppsala University, Sweden) (17), Piezo1$^{fl/fl}$ (Piezo1$^{tm2.1Apat}$/J. Jackson Laboratory) (29). Mice were maintained in mixed outbred backgrounds. Tamoxifen (MP Biomedicals, Santa Ana, California) was dissolved in Dimethyl sulfoxide (DMSO), mixed with Sunflower Seed Oil (1 vol. DMSO: 2 vol. Oil), and injected at 50 mg/kg once for pups and three times for young adults. Yoda1 (Sigma-Aldrich) was dissolved in DMSO, and then mixed with Phosphate Buffered Saline (1.5 vol. DMSO: 40 vol. PBS) before injection at 70 μg/kg.

Statistical Analysis

Unpaired, two-tailed, Student t-test was used to determine if the differences between the experimental and control groups were statistically significant. P-value less than 0.05 was considered to significant. Analyses were performed using Microsoft Excel (Microsoft Office) and GraphPad PRISM6 (GraphPad Software, Inc).

Figure Legends

FIG. 1A shows an experimental scheme, wherein: Tamoxifen (70 mg/kg) or vehicle (DMSO/Sunflower oil) was subcutaneously injected into neonatal mouse pups (P1). Tissue samples were harvested at P7 to analyze their genotypes and lymphatic valve development. Pups harboring Prox1-tdTomato, but lacking floxed Piezo1 alleles were considered as the control pups (CTR), while pups having Prox1-tdTomato, Prox1-CreER$^{T2}$, and Piezo1$^{fl/fl}$ were defined as lymphatic Piezo1 KO (Piezo1$^{\Delta LEC}$).

FIGS. 1B, 1C, 1D, 1E, 1F, and 1G show visualizations of tdTomato signals in the mesenteric lymphatics of Piezo1 knockout (KO) mouse pups having Prox1 promoter-driven tdTomato signals. Lymphatic Piezo1 KO inhibited proper formation of lymphatic valves and networks in the mesentery. Boxed areas in (B) and (C) are enlarged in (D) and (E), respectively. High magnification images of mesenteric lymphatic valves of wild type (F) or Piezo1 KO (G) pups revealed immature or incomplete valve formation in the Piezo1 KO pups.

FIGS. 1H, 1I, 1J, and 1K show images of impaired dermal lymphatic valve development in the tail skin of lymphatic Piezo1 KO mouse pups. Boxed areas in (H) and (I) are enlarged in (J) and (K), respectively.

Figures 1L, 1M:
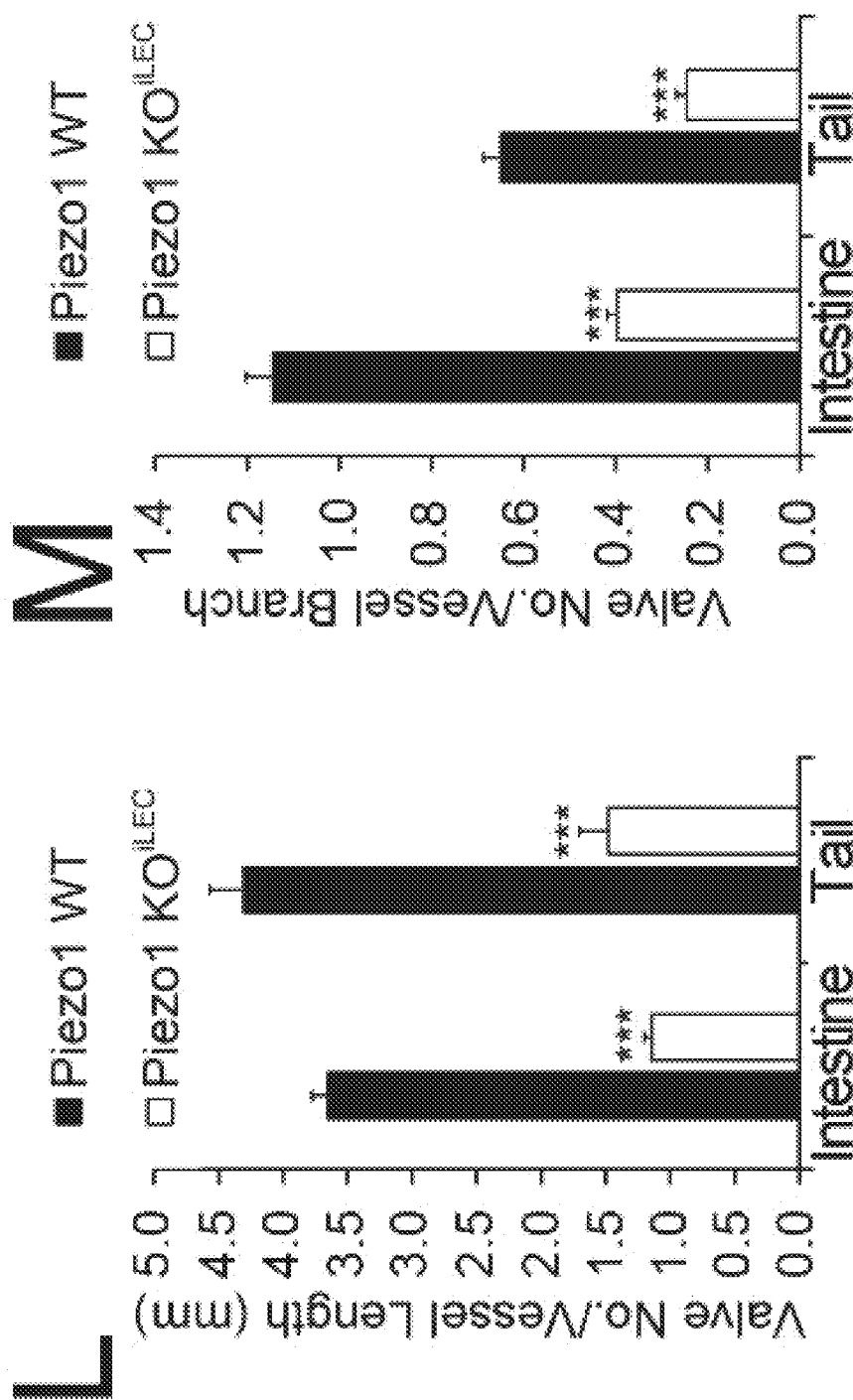
FIGS. 1L and 1M are graphs showing valve number per vessel length (L) or per vessel branch (M) in the intestine and tail of the Piezo1 KO mouse pups.

FIGS. 1L and 1M are graphs showing valve number per vessel length (L) or per vessel branch (M) in the intestine and tail of the Piezo1 KO mouse pups. Arrows mark Prox1-high lymphatic valves. Scale bars, 1 mm (B-E), 200 µm (H-K), 50 µm (F,G). Error bars denote standard error of mean (SEM). Statistics: ***, p<0.001, unpaired, two-tailed, t-test compared to the valve of wild type controls. Images shown represent >10 images of each condition. n>5 pups each group.

FIG. 2A shows an experimental scheme, wherein Tamoxifen was intraperitoneally injected into young adult mice every other day for total three times starting from day 21, and lymphatic valve maintenance was analyzed at day 49. Control mice (CTR) had Prox1-tdTomato and Prox1-CreER$^{T2}$ alleles, while lymphatic Piezo1 KO mice (Piezo1$^{\Delta LEC}$) harbored all Prox1-tdTomato, Prox1-CreER$^{T2}$, and Piezo1.

Figure 2E:
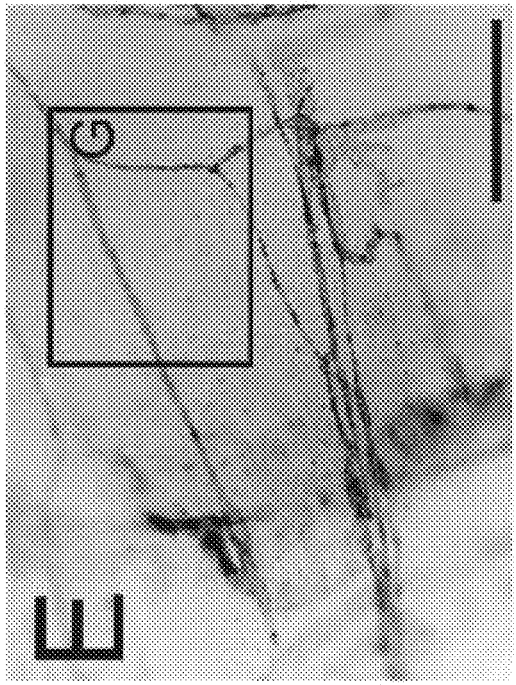
Figure 2G:
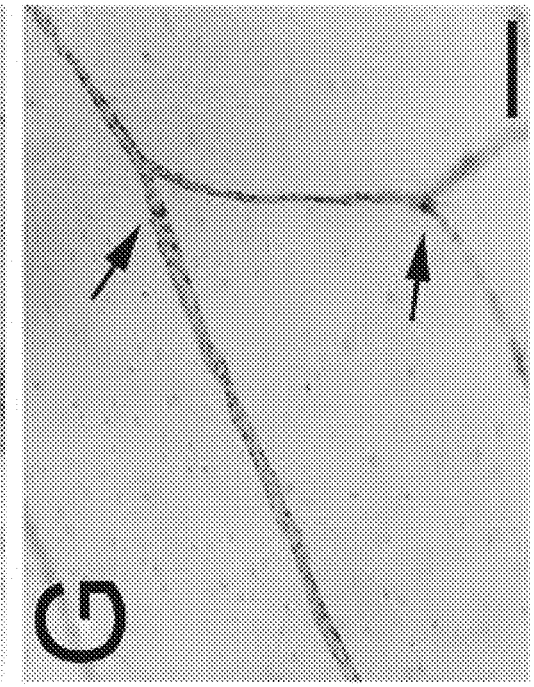
Figure 2D:
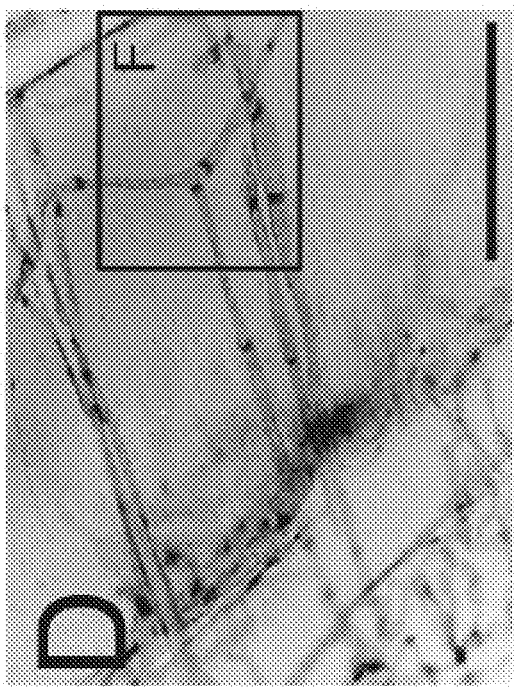
Figure 2F:
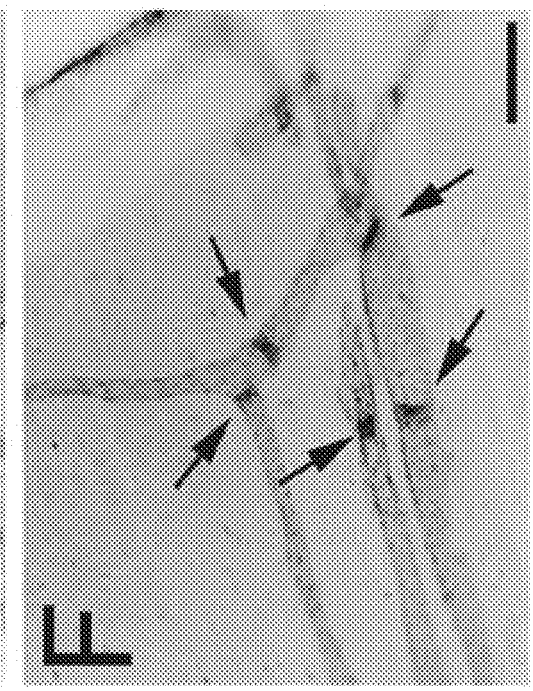

FIGS. 2B, 2C, 2D, 2E, 2F, and 2G show gross images of collecting lymphatic vessels closely running next to the saphenous vein in the hind limb of control and lymphatic or Piezo1 KO mice. Note healthy valves in the control mice as shown in FIGS. 2B, 2D, and 2F, but degenerated valve remnants in Piezo1 KO mice as shown in FIGS. 2C, 2E, and 2G.

Figure 2H:
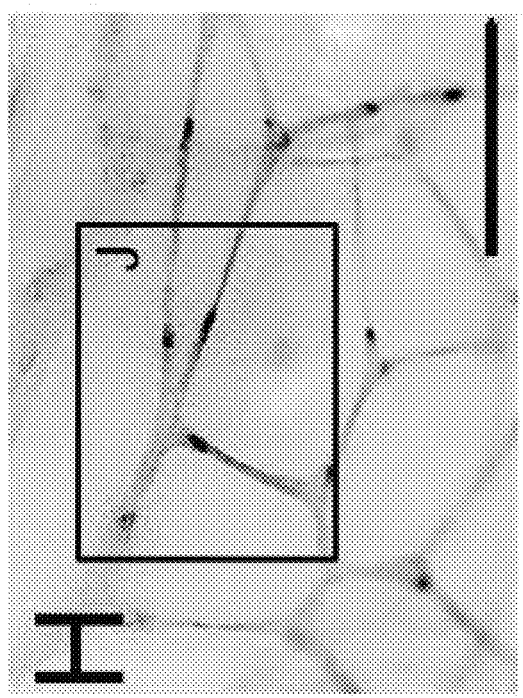
FIGS. 2H and 2J show images of mesenteric lymphatic vessels and valves in control mice.
Figure 2I:
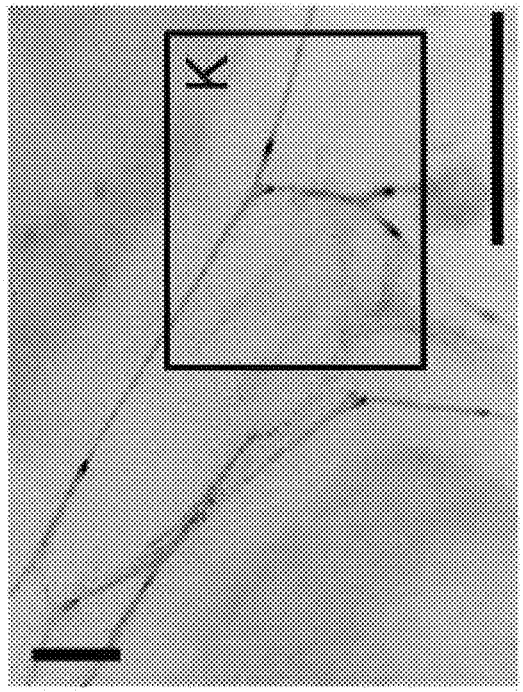
FIGS. 2I and 2K show images of mesenteric lymphatic vessels and valves in Piezo1 KO mice.
Figure 2J:
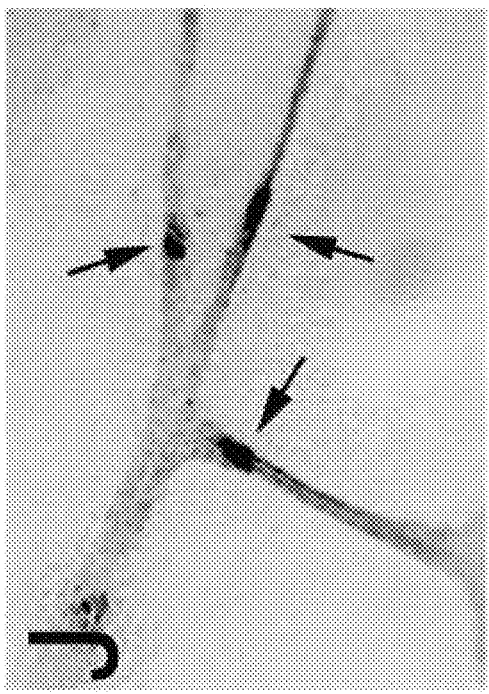

FIGS. 2H and 2J show images of mesenteric lymphatic vessels and valves in control mice.

Figure 2K:
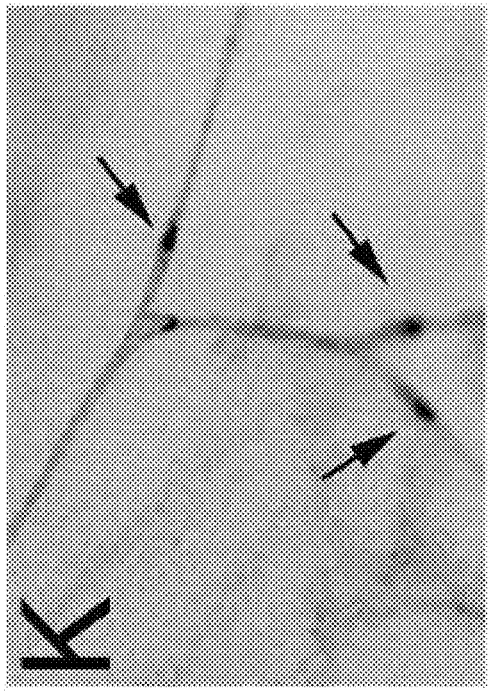

FIGS. 2I and 2K show images of mesenteric lymphatic vessels and valves in Piezo1 KO mice.

Figures 2L, 2M:
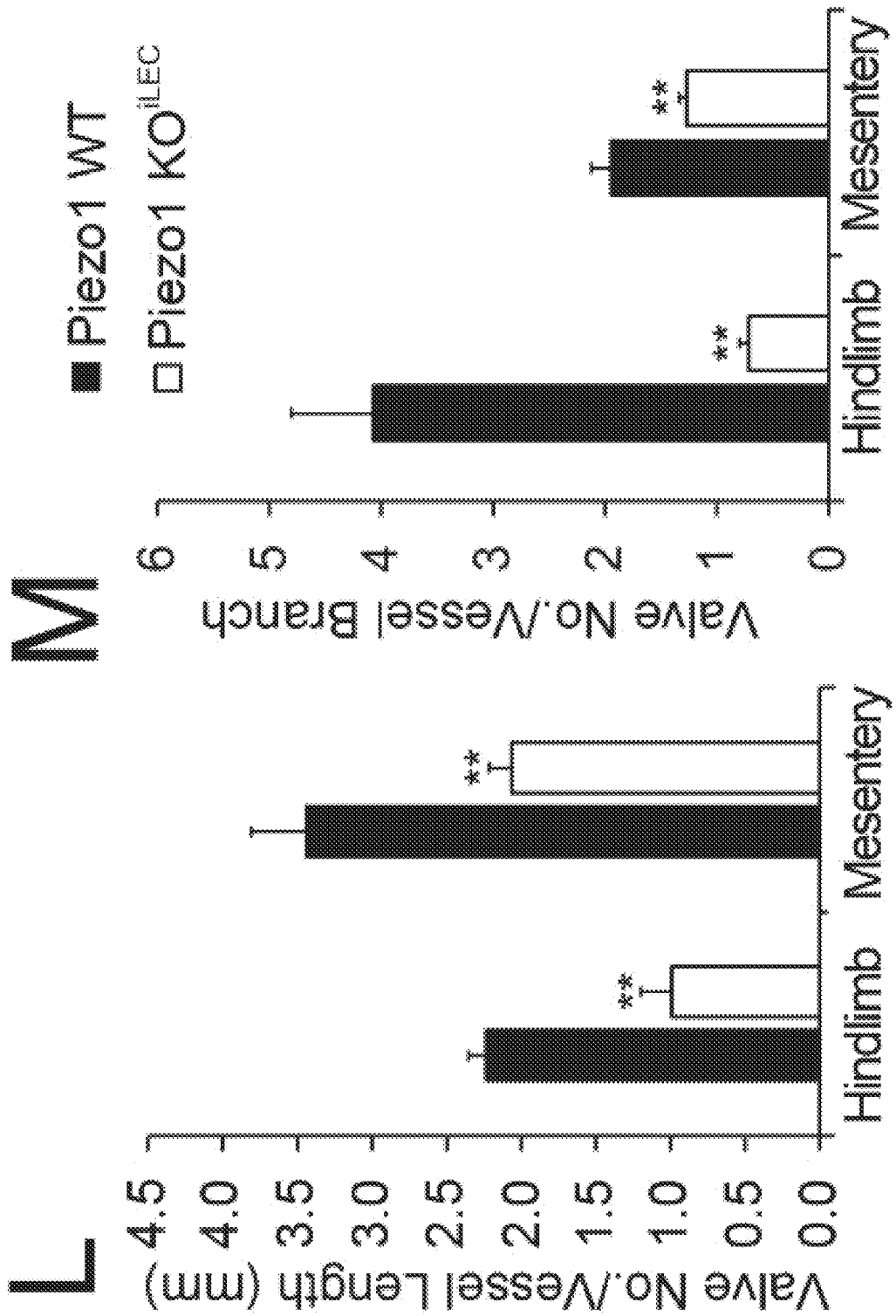
FIGS. 2L and 2M are graphs showing valve number per vessel length (L) and valve number per vessel branch (M) in the hind limb and mesentery of control and lymphatic Piezo1 KO mice.

FIGS. 2L and 2M are graphs showing valve number per vessel length (L) and valve number per vessel branch (M) in the hind limb and mesentery of control and lymphatic Piezo1 KO mice. Scale bars, 1 mm (B-E, H,I), 200 µm (F,G). Errorbars denote SEM. Statistics: , p<0.01; *, p<0.001, unpaired, two-tailed, t-test compared to the valve of wild type controls. Images shown represent >10 images of each condition. n>5 mice each group FIG. 3A are Western immunoblot assays showing protein expression of FOXC2 and GATA2 from primary human lymphoid endothelial cells (LECs) subjected to oscillatory shear stress (OSS) for the indicated time. FIG. 3B is a graph showing mRNA levels of Cx37, LAMA5 and ITGA9 from LECs subjected to OSS for the indicated time. As expected, protein expression of FOXC2 and GATA2 as shown in FIG. 3A or mRNA level of Cx37, LAMA5 and ITGA9 as shown in FIG. 3B were determined by western or qRT-PCR, respectively. Error bars denote Standard Deviation (SD). Statistics: , p<0.01; *, p<0.001, unpaired, two-tailed, t-test compared to the valve of static culture shown in FIG. 3B.

FIG. 3C are Western immunoblot assays showing regulation of lymphatic valve-associated genes by Piezo1. LECs were transfected with scrambled siRNA (siCTR) or Piezo1 siRNA (siPiezo1) for 24 hours and subjected to static culturing or OSS for 24 hours. OSS was applied approximately at 6 dyne/cm$^2$, ½ Hz, as described in Supplemental Method.

FIG. 3D shows images from immunofluorescence assays against genes of interest (FOXC2, GATA2, Cx37, LAMA5, and ITGA9). As shown in FIG. 3D, Piezo1 upregulates the lymphatic valve-associated genes. LECs were transfected with a Piezo1/EGFP-expressing plasmid, and then cultured statically for 48 hours before immunofluorescence assays against Genes of Interest (FOXC2, GATA2, Cx37, LAMA5, and ITGA9). Arrowheads indicate transfected EGFP-positive (thus Piezo1-overexpressing) cells, whereas arrows point EGFP-negative, untransfected cells. Scale bars, 50 µm.

FIG. 3E is graph of a qRT-PCR analysis showing the expression of the lymphatic valve-associated genes in LECs that were transfected with a control (CTR) or Piezo1/EGFP-expressing plasmid (Piezo1) for 24 hours. FIG. 3F is a Western immunoblot assay showing the expression of the lymphatic valve-associated genes in LECs that were transfected with a control (CTR) or Piezo1/EGFP-expressing plasmid (Piezo1) for 48 hours. The qRT-PCR highlighted in FIG. 3E and the Western blot assays highlighted in FIG. 3F show the expression of the lymphatic valve-associated genes in LECs that were transfected with a control (CTR) or Piezo1/EGFP-expressing plasmid (Piezo1) for 24 (FIG. 3E), or 48 hours (FIG. 3F) in the absence of OSS. Error bars denote Standard Deviation (SD). Statistics: , p<0.01; *, p<0.001, unpaired, two-tailed, t-test compared to the control plasmid shown in FIG. 3E.

FIG. 4A are Western immunoblot assays showing expression of lymphatic valve genes in primary LECs that were subjected to static culturing or cyclic cell stretching for 4, 8, and 24 hours. The Western blot assays show upregulation of the lymphatic valve genes in primary LECs that were subjected to static culturing or cyclic cell stretching for 4, 8, and 24 hours.

Figure 4B:
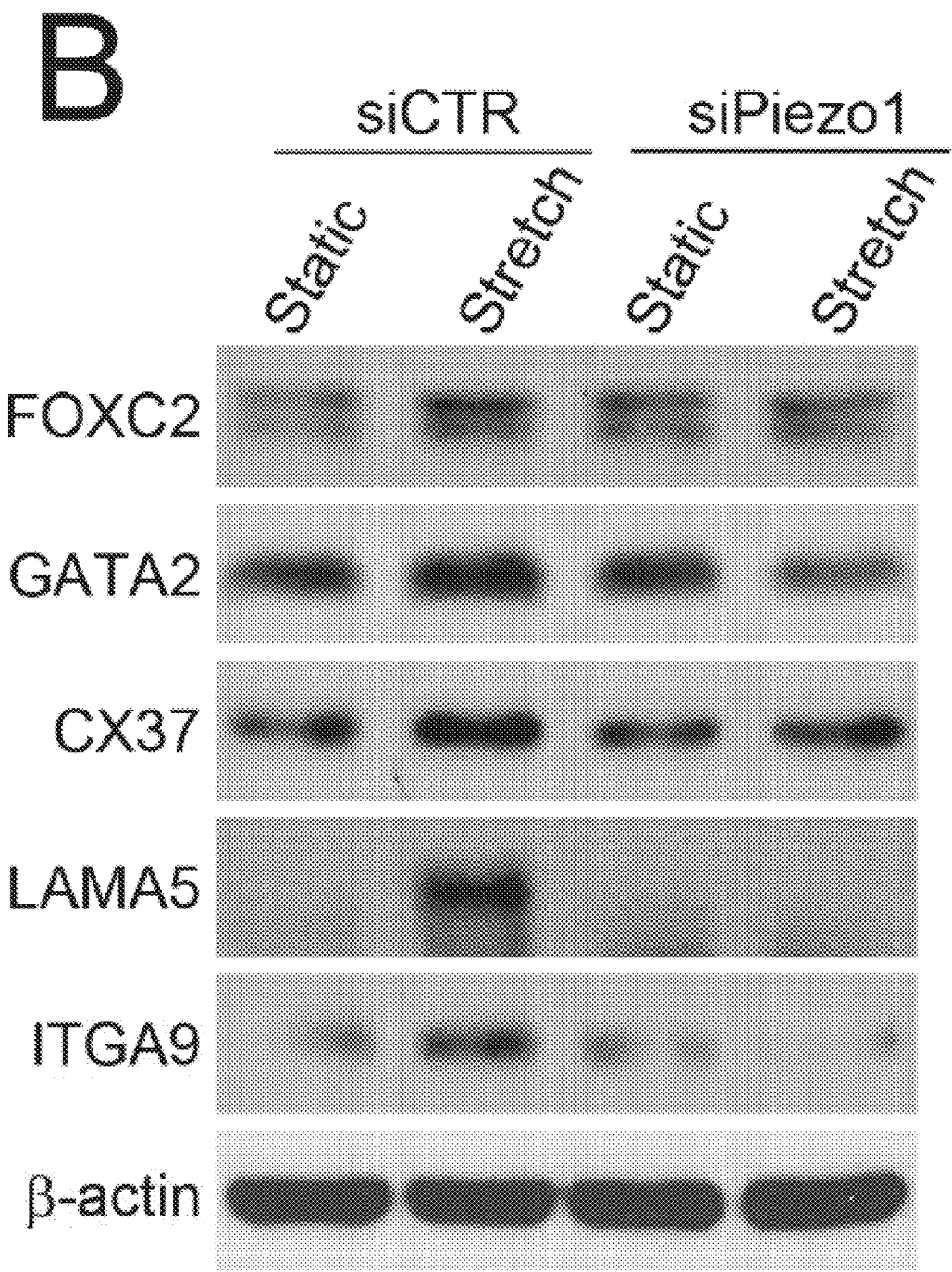
FIG. 4B are Western immunoblot assays showing expression of FOXC2, GATA2, Cx37, LAMA5, and ITGA9 in LECs expressing scrambled siRNA (siCTR) or Piezo1 siRNA (siPiezo1) for 24 hours and then subjected to static culturing or cyclic stretching for 12 hours prior to western blot assays.

FIG. 4B are Western immunoblot assays showing expression of FOXC2, GATA2, Cx37, LAMA5, and ITGA9 in LECs expressing scrambled siRNA (siCTR) or Piezo1 siRNA (siPiezo1) for 24 hours and then subjected to static culturing or cyclic stretching for 12 hours prior to western blot assays. Piezo1 was knocked-down or not in LECs using scrambled siRNA (siCTR) or Piezo1 siRNA (siPiezo1) for 24 hours and the cells were then subjected to static culturing or cyclic stretching for 12 hours prior to western blot assays. Cyclic stretching was applied onto the cells at ½ Hz for 12 hours to stretch the cell length to 112% as described in Supplemental Method.

Figure 4C:
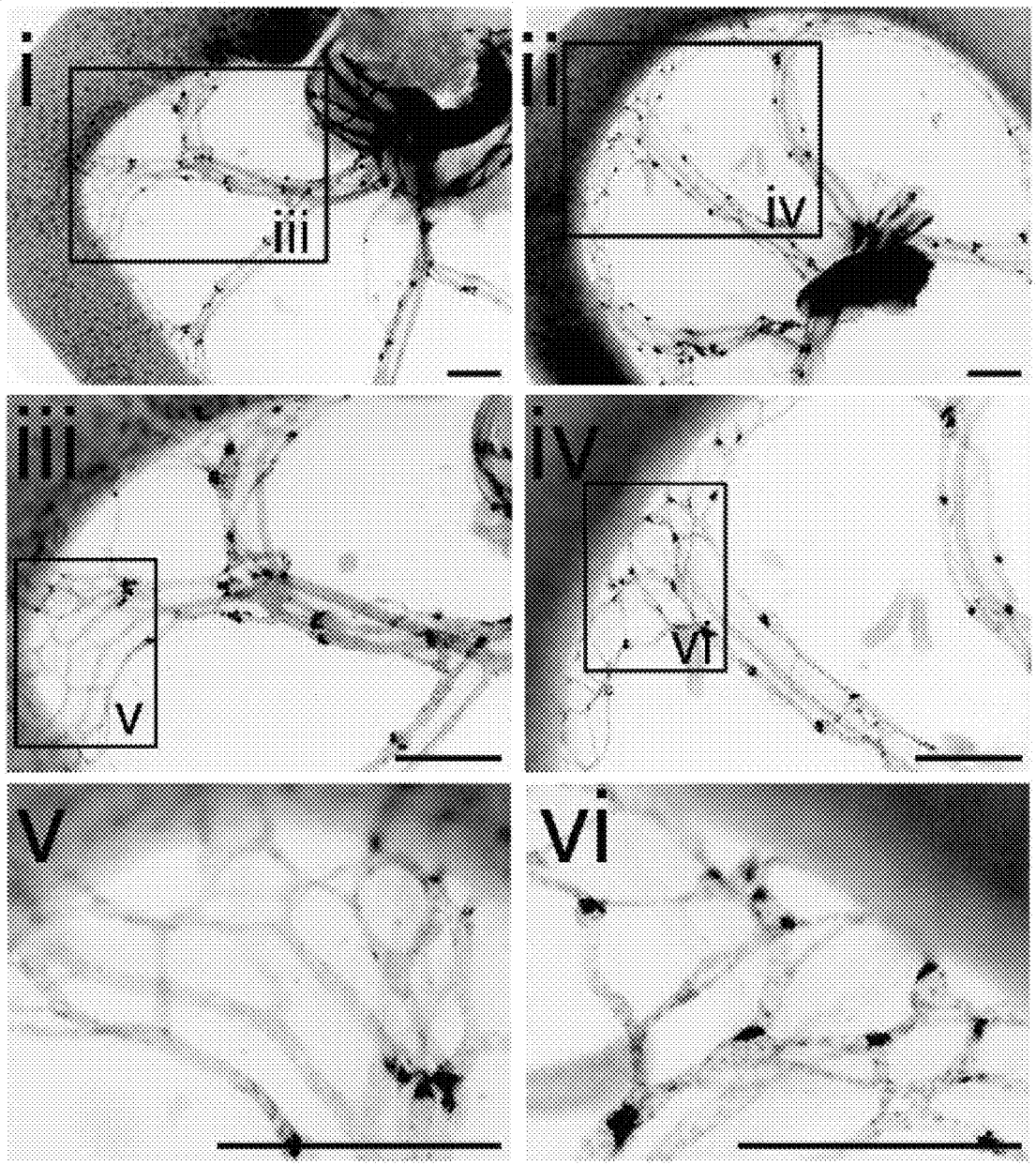
FIG. 4C shows images of developing mesenteric lymphatic valves in the jejunum of pups treated with Yoda1.
Figure 4D:
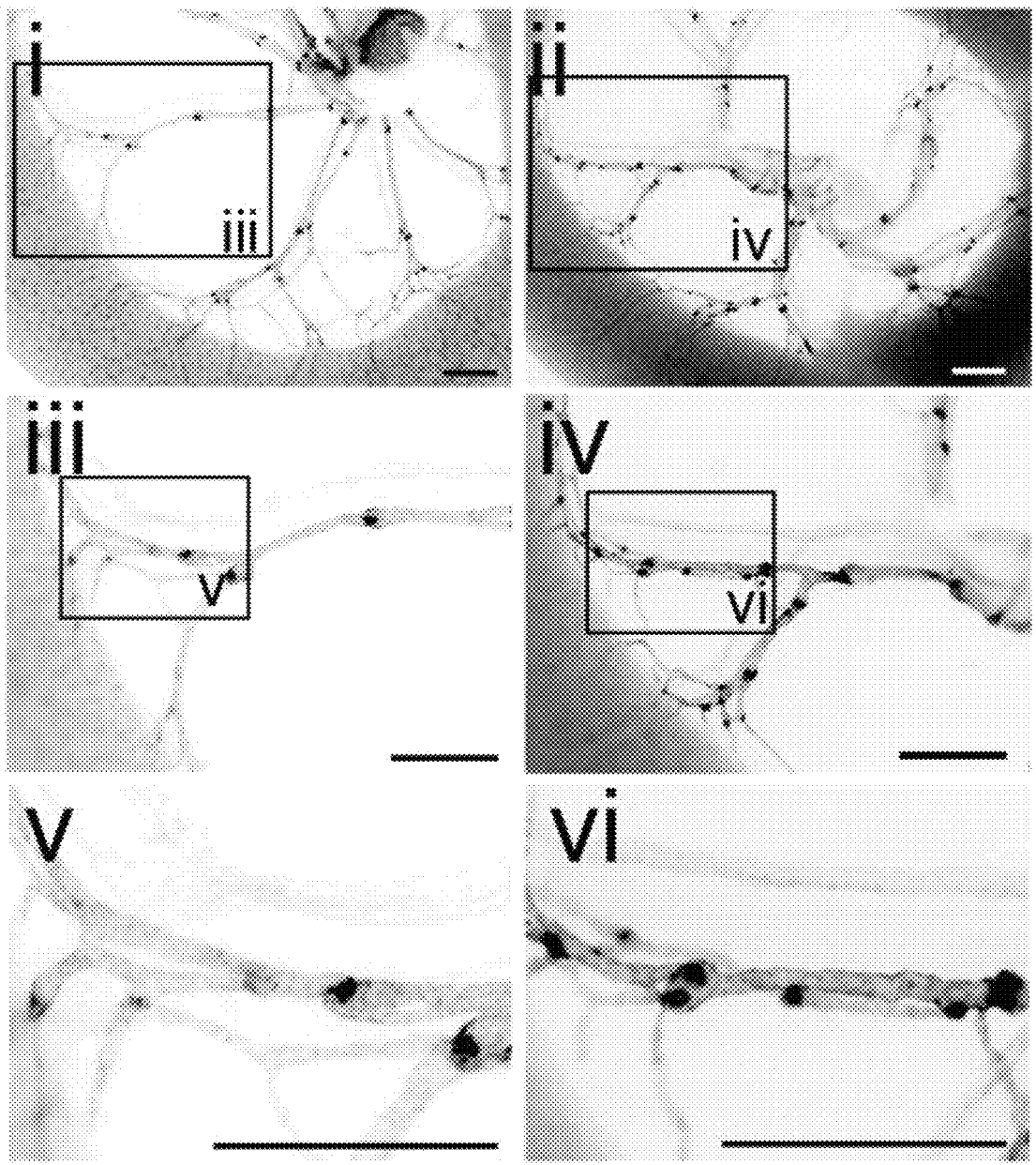
FIG. 4D shows images of developing mesenteric lymphatic valves in the colon of pups treated with Yoda1.

FIG. 4C shows images of developing mesenteric lymphatic valves in the jejunum of pups treated with Yoda1. FIG. 4D shows images of developing mesenteric lymphatic valves in the colon of pups treated with Yoda1. Pregnant Prox1-EGFP females at E18.5 were intraperitoneal injected with vehicle or Yoda1 (70 µg/kg). After birth, individual pups were once again injected with vehicle or Yoda1 (70<g/kg) at P0, and then euthanized for lymphatic valve analyses at P1. Equivalent anatomic locations were selected for capturing images in the vehicle and Yoda1-treated groups, and their lymphatic valve formation was investigated and quantified (Supplemental FIG. 5).

Results and Discussion

Piezo1 is Important for Lymphatic Valves Development

We aimed to study the impact of Piezo1 deletion to lymphatic valve formation by inducing conditional deletion of Piezo1 in lymphatic endothelial cells (LECs). We produced pups harboring Prox-CreER$^{T2}$ (17), Prox1-tdTomato (28), and/or Piezo1$^{fl/fl}$ (29) alleles. As shown in FIG. 1A, lymphatic Piezo1 deletion (Piezo1$^{\Delta LEC}$) was then induced in the pups at postnatal day 1 (P1) by tamoxifen injection, and lymphatic valve formation in the mesentery and tail skin were analyzed at P7. Mesenteric lymphatic valves, clearly marked with a strong tdTomato expression (thus Prox1), were found in most vascular branch points of the control animals. In the lymphatic Piezo1 KO pups, however, not only mesenteric lymphatics were significantly under-developed, but also they lack lymphatic valves in the branching points as shown in FIGS. 1B-1E, 1Lm and 1M. High power images as shown in FIGS. 1F and 1G revealed that Piezo1 deletion may arrest valve development at various stages, such as initiation and maturation, depending on developmental status of individual valves at P1 (14). As shown in FIGS. 1H-1K, 1L, and 1M, lymphatic valve defects were also detected in the tail skin of lymphatic Piezo1 KO pups. Strikingly, the majority of lymphatic branching points in Piezo1-deficient pups were devoid of the valves. Together, these data demonstrate that Piezo1 is required for mesenteric and dermal lymphatic valve formation.

Piezo1 Deletion Leads to Degeneration of Lymphatic Valves in Adults

We next asked whether Piezo1 is continuously needed to maintain lymphatic valves in adults. Lymphatic Piezo1 deletion was induced in mice at day 21 and the integrity of lymphatic valves in the skin and mesentery were investigated at day 49 as shown in FIG. 2A. We examined collecting lymphatic vessels that run along with the saphenous vein in the hind limb in the control and mutant mice. Notably as shown in FIGS. 2B-2G, 2L, and 2M, lymphatic Piezo1 deletion not only reduced lymphatic vessel density, but also led to significant degeneration of lymphatic valves. These lymphatic atrophies were also detected in the mesentery, where Piezo1-deficient lymphatics were much thinner and scarce with fewer valves, compared to those of the control lymphatics as shown in FIGS. 2H-2M. Together, these data suggest that Piezo1 function is necessary to maintain the integrity of lymphatic vessels and valves in adults.

Piezo1 Plays a Role in Inducing the Molecular Signatures of Lymphatic Valves

Fluid flow delivers a significant impact to various aspects of vascular development (5). In particular, shear stress (OSS) imposed by oscillatory flow plays an essential role in lymphatic valve development by upregulating the lymphatic valve-associated genes, such as FOXC2, GATA2, CX37, LAMA5 and ITGA9, and also by inducing cellular morphological transition (13-20). We thus interrogated how the mechanosensor Piezo1 affects this mechanotransduction process by in vitro loss-of-function (LOF) studies. Consistent with the previous studies (13-18), when cultured primary human LECs were exposed to OSS, we could detect their cell morphology changes to cuboidal shapes as shown in Supplemental FIG. 1 and upregulation of mRNA and protein of the lymphatic valve-associated genes listed above and as shown in FIGS. 3A, 3B, and Supplemental FIG. 2. Importantly, the OSS-induced upregulation of the lymphatic valve genes were largely abrogated by Piezo1 knockdown as shown in FIG. 3C and Supplemental FIG. 3. Notably, upregulation of ITGA9 by OSS was not affected by Piezo1 knockdown. Together, these data suggest that Piezo1 may play a key role in the OSS-activated mechanotransduction that regulates the gene expression profiles of lymphatic valves.

We next asked whether ectopic Piezo1 expression recapitulates the molecular phenotypes caused by OSS as a gain-of-function (GOF) study. We transfected primary LECs with a plasmid bicistronically encoding Piezo1 and EGFP, and studied the effect of Piezo1 expression on the regulation of the lymphatic valve-associated genes. While EGFP-positive, transfected LECs, (thus overexpressing Piezo1), indeed upregulated FOXC2, GATA2, CX37, and LAMA5 by 3-4 fold (See arrowheads of FIG. 3D and Supplemental FIG. 4A), neighboring EGFP-negative, untransfected LECs did not upregulate these genes (See arrows of FIG. 3D), Notably, ITGA9 was not upregulated by Piezo1 overexpression, suggesting that an independent mechanism may upregulate the OSS-induced ITGA9 expression. To confirm these data, LECs were transfected with a control or Piezo1-expressing vector and cultured for 48 hours in the absence of OSS. Indeed, overexpression of Piezo1 was sufficient to induce the lymphatic valve-associated genes, except ITGA9 as shown in FIGS. 3E and 3F. Together, these loss/gain-of-function studies demonstrate an essential role of Piezo1 in the OSS-activated mechanotransduction that controls lymphatic valve development.

Activation of Piezo1 Promotes Lymphatic Valve Formation

As Piezo1 was originally identified as a mechanically activated cation channel (21-25), we next asked whether another physical force, such as cell stretching, could stimulate Piezo1 and induce the molecular signature of lymphatic valves. To address this question, primary LECs were subjected to cyclic cell stretching (112%, 12 Hz) for 4, 8, and 24 hours in the absence of OSS, and the expression of the lymphatic valve genes were investigated. Indeed, cyclic cell stretching alone led to significant upregulation of FOXC2, GATA2, CX37, LAMA5 and ITGA9, and these upregulations required the function of Piezo1 as shown in FIGS. 4A, 4B, and Supplemental FIG. 4B. In addition, we investigated whether chemical activation of Piezo1 promotes lymphatic valve formation in animals. Prox1-EGFP mice were perinatally administrated at E18.5 and P0 with a chemical agonist of Piezo1, Yoda1 (30), and lymphatic valve formation in the small intestine, colon, and skin was evaluated at P1. Indeed, chemical activation of Piezo1 by Yoda1 significantly expedited the lymphatic valve formation in the mesenteries of the jejunum and the colon, as well as in the tail skin as shown in FIGS. 4C, 4D, and Supplemental FIG. 5. We then asked whether Yoda1 could activate cultured LECs to upregulate lymphatic valve genes in the absence of OSS. Interestingly, Yoda1-treated LECs upregulates GATA2, CX37, LAMA5 and ITGA9 in a Piezo1-depenent manner, butFOXC2 was rather downregulated as shown in Supplemental FIG. 6. Taken together, our studies demonstrate that physical or chemical activation of Piezo1 could trigger the mechanotransduction that controls the lymphatic valve development program.

Lymphatic valves are essential for unidirectional flow of the interstitial fluid. Diseased lymphatic valves due to developmental malformations or post-developmental injuries often lead to severe lymphatic pathologies. Several recent studies demonstrated that fluid flow-derived physical signal significantly controls lymphatic valve development through various mechanotransduction pathways, and identified several molecular constituents essential for the pathways (13-20). In this study, we defined the crucial role of Piezo1 in incorporating the flow-mediated physical signal into the genetic program controlling lymphatic valve development. One striking finding from our study is that cyclic cell stretching of cultured LECs in the absence of the OSS-mediated shear stress could also recapitulate the molecular signatures of lymphatic valves, which were induced by OSS. Previous studies suggested that vascular endothelial cells in vivo would be subjected to both fluid shear stress and cyclic cell stretch, and, when combined in vitro, these two physical stimuli appeared to be synergistic in conferring vascular phenotypes such as actin filament alignment and differentiation (31-34). Accordingly, we hypothesize that the OSS-induced shear stress and cyclic cell stretching may be independently and/or cooperatively sensed by Piezo1, which then triggers the molecular phenotypes of lymphatic valves. It is plausable that OSS itself may induce a similar pattern of plasma membrane spreading and cytoskeletal rearrangement, which are created by cyclic cell stretching. Therefore, it would be interesting to study how similarly or differentially these two physical forces activate Piezo1 and trigger the lymphatic valve-forming genetic program. Another key finding of this study is that, compared to these two physical stimuli, ectopic upregulation or chemical activation of Piezo1 only partially recapitulated the lymphatic valve gene expression phenotypes. Nevertheless, in vivo chemical activation of Piezo1 using Yoda1 showed an accelerated lymphatic valve formation. Among other possibilities, we favor to interpret this data that the OSS and cyclic cell stretching may deliver additional signals that may activate other mechanotransduction pathway important for lymphatic valve development. In summary, our study defined the essential role of the cell stretch sensor Piezo1 in the OSS-induced lymphatic valve development and maintenance.

Cited References for Example 1

1. Breslin J W. Mechanical forces and lymphatic transport. *Microvascular Research*. 2014; 96(46-54).
2. Bazigou E, Wilson J T, and Moore J E, Jr. Primary and secondary lymphatic valve development: molecular, functional and mechanical insights. *Microvascular Research*. 2014; 96(38-45).
3. Bazigou E, and Makinen T. Flow control in our vessels: vascular valves make sure there is no way back. Cellular and molecular life sciences: CMLS. 2013; 70(6):1055-66.
4. Schmid-Schonbein G W. The second valve system in lymphatics. *Lymphatic Research and Biology*. 2003; 1(1):25-9; discussion 9-31.
5. Chiu J J, and Chien S. Effects of disturbed flow on vascular endothelium: pathophysiological basis and clinical perspectives. *Physiol Rev*. 2011; 91(1):327-87.
6. Schwartz M A, and Simons M. Lymphatics thrive on stress: mechanical force in lymphatic development. *Embo J*. 2012; 31(4):781-2.
7. Sessa W C. Molecular control of blood flow and angiogenesis: role of nitric oxide. *J Thromb Haemost*. 2009; 7 Suppl 1(35-7).
8. Boldock L, Wittkowske C, and Perrault C M. Microfluidic traction force microscopy to study mechanotransduction in angiogenesis. *Microcirculation*. 2017; 24(5).
9. Sabine A, Saygili Demir C, and Petrova T V. Endothelial Cell Responses to Biomechanical Forces in Lymphatic Vessels. Antioxid Redox *Signal*. 2016; 25(7):451-65.
10. Baeyens N, Bandyopadhyay C, Coon B G, Yun S, and Schwartz M A. Endothelial fluid shear stress sensing in vascular health and disease. *J Clin Invest*. 2016; 126(3):821-8.
11. Baeyens N, and Schwartz M A. Biomechanics of vascular mechanosensation and remodeling. *Mol Biol Cell*. 2016; 27(1):7-11.
12. Chatterjee S, Fujiwara K, Perez N G, Ushio-Fukai M, and Fisher A B. Mechanosignaling in the vasculature: emerging concepts in sensing, transduction and physiological responses. *Am J Physiol Heart Circ Physiol*. 2015; 308(12):H1451-62.
13. Kazenwadel J, Betterman K L, Chong C E, Stokes P H, Lee Y K, Secker G A, Agalarov Y, Demir C S, Lawrence D M, Sutton D L, et al. GATA2 is required for lymphatic vessel valve development and maintenance. *The Journal of clinical investigation*. 2015; 125(8):2979-94.
14. Sabine A, Agalarov Y, Maby-El Hajjami H, Jaquet M, Hagerling R, Pollmann C, Bebber D, Pfenniger A, Miura N, Dormond O, et al. Mechanotransduction, PROX1, and FOXC2 cooperate to control connexin37 and calcineurin during lymphatic-valve formation. *Dev Cell*. 2012; 22(2):430-45.
15. Sabine A, Bovay E, Demir C S, Kimura W, Jaquet M, Agalarov Y, Zangger N, Scallan J P, Graber W, Gulpinar E, et al. FOXC2 and fluid shear stress stabilize postnatal lymphatic vasculature. *J Clin Invest*. 2015; 125(10):3861-77.
16. Cha B, Geng X, Mahamud M R, Fu J, Mukherjee A, Kim Y, Jho E H, Kim T H, Kahn M L, Xia L, et al. Mechanotransduction activates canonical Wnt/beta-catenin signaling to promote lymphatic vascular patterning and the development of lymphatic and lymphovenous valves. *Genes Dev*. 2016; 30(12):1454-69.
17. Bazigou E, Lyons O T, Smith A, Venn G E, Cope C, Brown N A, and Makinen T. Genes regulating lymphangiogenesis control venous valve formation and maintenance in mice. *J Clin Invest*. 2011; 121(8):2984-92.
18. Bazigou E, Xie S, Chen C, Weston A, Miura N, Sorokin L, Adams R, Muro A F, Sheppard D, and Makinen T. Integrin-alpha9 is required for fibronectin matrix assembly during lymphatic valve morphogenesis. *Dev Cell*. 2009; 17(2):175-86.
19. Udan R S, and Dickinson M E. The ebb and flow of lymphatic valve formation. *Dev Cell*. 2012; 22(2):242-3.
20. Janardhan H P, Milstone Z J, Shin M, Lawson N D, Keaney J F, Jr., and Trivedi C M. Hdac3 regulates lymphovenous and lymphatic valve formation. *J Clin Invest*. 2017; 127(11):4193-206.
21. Coste B, Xiao B, Santos J S, Syeda R, Grandl J, Spencer K S, Kim S E, Schmidt M, Mathur J, Dubin A E, et al. Piezo proteins are pore-forming subunits of mechanically activated channels. *Nature*. 2012; 483(7388):176-81.
22. Kim S E, Coste B, Chadha A, Cook B, and Patapoutian A. The role of *Drosophila* Piezo in mechanical nociception. *Nature*. 2012; 483(7388):209-12.
23. Coste B, Mathur J, Schmidt M, Earley T J, Ranade S, Petrus M J, Dubin A E, and Patapoutian A. Piezo1 and Piezo2 are essential components of distinct mechanically activated cation channels. *Science*. 2010; 330(6000):55-60.
24. Ranade S S, Qiu Z, Woo S H, Hur S S, Murthy S E, Cahalan S M, Xu J, Mathur J, Bandell M, Coste B, et al. Piezo1, a mechanically activated ion channel, is required for vascular development in mice. *Proc Natl Acad Sci USA*. 2014; 111(28):10347-52.
25. Li J, Hou B, Tumova S, Muraki K, Bruns A, Ludlow M J, Sedo A, Hyman A J, McKeown L, Young R S, et al. Piezo1 integration of vascular architecture with physiological force. *Nature*. 2014; 515(7526):279-82.
26. Lukacs V, Mathur J, Mao R, Bayrak-Toydemir P, Procter M, Cahalan S M, Kim H J, Bandell M, Longo N, Day R W, et al. Impaired PIEZO1 function in patients with a novel autosomal recessive congenital lymphatic dysplasia. *Nat Commun*. 2015; 6(8329).
27. Fotiou E, Martin-Almedina S, Simpson M A, Lin S, Gordon K, Brice G, Atton G, Jeffery I, Rees D C, Mignot C, et al. Novel mutations in PIEZO1 cause an autosomal recessive generalized lymphatic dysplasia with non-immune hydrops fetalis. *Nat Commun*. 2015; 6(8085).
28. Hong M, Jung E, Yang S, Jung W, Seong Y J, Park E, Bramos A, Kim K E, Lee S, Daghlian G, et al. Efficient Assessment of Developmental, Surgical and Pathological Lymphangiogenesis Using a Lymphatic Reporter Mouse and Its Embryonic Stem Cells. *PLoS ONE*. 2016; 11(6): e0157126.
29. Cahalan S M, Lukacs V, Ranade S S, Chien S, Bandell M, and Patapoutian A. Piezo1 links mechanical forces to red blood cell volume. Elife. 2015; 4.
30. Syeda R, Xu J, Dubin A E, Coste B, Mathur J, Huynh T, Matzen J, Lao J, Tully D C, Engels I H, et al. Chemical activation of the mechanotransduction channel Piezo1. *Elife*. 2015; 4.
31. Zhao S, Suciu A, Ziegler T, Moore J E, Jr., Burki E, Meister J J, and Brunner H R. Synergistic effects of fluid shear stress and cyclic circumferential stretch on vascular endothelial cell morphology and cytoskeleton. *Arterioscler Thromb Vasc Biol*. 1995; 15(10):1781-6.
32. Kim D H, Heo S J, Kang Y G, Shin J W, Park S H, and Shin J W. Shear stress and circumferential stretch by pulsatile flow direct vascular endothelial lineage commitment of mesenchymal stem cells in engineered blood vessels. JMater Sci Mater Med. 2016; 27(3):60.
33. Moore J E, Jr., Burki E, Suciu A, Zhao S, Burnier M, Brunner H R, and Meister J J. A device for subjecting vascular endothelial cells to both fluid shear stress and circumferential cyclic stretch. *Ann Biomed Eng*. 1994; 22(4):416-22.
34. Owatverot T B, Oswald S J, Chen Y, Wille J J, and Yin F C. Effect of combined cyclic stretch and fluid shear stress on endothelial cell morphological responses. *J Biomech Eng*. 2005; 127(3):374-82.
35. Choi I, Chung H K, Ramu S, Lee H N, Kim K E, Lee S, Yoo J, Choi D, Lee Y S, Aguilar B, et al. Visualization of lymphatic vessels by Prox1-promoter directed GFP reporter in a bacterial artificial chromosome-based transgenic mouse. *Blood*. 2011; 117(1):362-5.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of treating impaired lymphatic function in a subject, the method comprising the step of:
administering a pharmaceutical composition to the subject having dysfunctional lymphatic valves in lymphatic tissues to treat the dysfunctional lymphatic valves in the lymphatic tissues, wherein the pharmaceutical composition includes a Piezo1 agonist that is 2-[(2,6-dichlorophenyl)methylsulfanyl]-5-pyrazin-2-yl-1,3,4-thiadiazole, wherein administration of the pharmaceutical composition is in a sufficient amount to enhance expression of lymphatic valve-associated genes FOXC2, GATA2, CX37, and LAMA5 through Piezo1-dependent pathways, and to promote expression of ITGA9 through Piezo1-independent pathways, thereby promoting formation and function of lymphatic valves.

2. The method of claim 1 further comprising applying oscillatory shear stress to the lymphatic tissues.

3. The method of claim 2, wherein the oscillatory shear stress does not activate Piezo2 ion channels in the lymphatic tissues.

4. The method of claim 2, wherein the applying step includes directing ultrasound pulses towards the lymphatic tissues.

5. The method of claim 4, wherein the ultrasound pulses have a frequency of 43 megahertz (MHz).

6. A method of treating ocular hypertension or glaucoma in a subject, the method comprising the step of:

administering a pharmaceutical composition to the subject having an ocular pressure that is greater than 22 mm Hg, wherein the pharmaceutical composition includes a Piezo1 agonist that is 2-[(2,6-dichlorophenyl)methylsulfanyl]-5-pyrazin-2-yl-1,3,4-thiadiazole, wherein the subject has ocular hypertension or glaucoma, wherein administration of the pharmaceutical composition is in a sufficient amount to enhance expression of lymphatic valve-associated genes FOXC2, GATA2, CX37, and LAMA5 through Piezo1-dependent pathways, and to promote expression of ITGA9 through Piezo1-independent pathways.

7. The method of claim 6 further comprising applying oscillatory shear stress to the eye.

8. The method of claim 7, wherein the oscillatory shear stress does not activate Piezo2 ion channels in the eye.

9. The method of claim 7, wherein the applying step includes directing ultrasound pulses towards the eye.

10. The method of claim 9, wherein the ultrasound pulses have a frequency of 43 megahertz (MHz).

11. The method of claim 7, wherein the pharmaceutical composition is administered in an amount effective for reducing the ocular pressure.

12. The method of claim 6, wherein the subject has glaucoma.

* * * * *